United States Patent [19]

Singer et al.

[11] Patent Number: 5,985,549
[45] Date of Patent: Nov. 16, 1999

[54] NON-ISOTOPIC IN-SITU HYBRIDIZATION METHOD FOR DETECTION OF NUCLEIC ACIDS

[75] Inventors: Robert H. Singer, Shrewsbury, Mass.; Jeanne B. Lawrence, Mapleville, R.I.

[73] Assignee: University of Massachusetts, Boston, Mass.

[21] Appl. No.: 08/316,809

[22] Filed: Oct. 3, 1994

Related U.S. Application Data

[63] Continuation of application No. 08/150,767, Nov. 12, 1993, abandoned, which is a continuation of application No. 07/832,667, Feb. 6, 1992, abandoned, which is a continuation of application No. 07/257,066, Oct. 13, 1988, abandoned, which is a continuation-in-part of application No. 06/790,107, Oct. 22, 1985, abandoned.

[51] Int. Cl.$^6$ ......................................... C12Q 1/68
[52] U.S. Cl. ............................. 435/6; 435/91.1; 436/501; 536/25.3
[58] Field of Search ............................. 435/6, 91.1, 91.2, 435/810; 436/501; 536/22.1, 23.1, 24.1, 24.3–33, 25.3; 935/77, 78

[56] References Cited

U.S. PATENT DOCUMENTS

| | | | |
|---|---|---|---|
| 4,419,446 | 12/1983 | Howley et al. | 435/6 |
| 4,652,517 | 3/1987 | Scholl et al. | 435/5 |
| 4,711,955 | 12/1987 | Ward et al. | 536/29 |
| 4,770,992 | 9/1988 | Van den Engh | 436/800 |
| 4,886,741 | 12/1989 | Schwartz | 435/5 |
| 4,888,278 | 12/1989 | Singer et al. | 435/6 |
| 5,028,525 | 7/1991 | Gray et al. | 435/6 |
| 5,447,841 | 9/1995 | Gray et al. | 435/6 |
| 5,597,692 | 1/1997 | Coghlan et al. | 435/6 |

FOREIGN PATENT DOCUMENTS

| | | |
|---|---|---|
| WO 90/05789 | 5/1990 | European Pat. Off. . |
| WO 90/02173 | 3/1990 | WIPO . |
| WO 90/02204 | 3/1990 | WIPO . |

OTHER PUBLICATIONS

Lawrence, J.B. et al., *J. Cell Biol 105*:Abstract No. 830 (Oct. 1987).
Bauman, J.G.J. and P.Bentvelzen, *Cytometry* 9:517–524 (1988).
Manuelidis (1984) Proc. Natl Acad Sci (USA) vol. 81, pp. 3123–3127.
*Molecular Cloning, A Laboratory Manual* (publ. Cold Spring Harbor Laboratory, New York, USA; Maniatis et al., (1982), pp. 188–189.
Landegent et al. (1984) Experimental Cell Res., vol. 153, pp. 61–72.
Rappold et al. (1984) Human Genet., vol. 67, pp. 317–325.
Lichter, P. et al., "Delineation of Individual Human Chromosomes in Metaphase and Interphase Cells by In Situ Suppression Hybridization . . . " *Hum. Genet.*, 51 (1988).
Pinkel, D. et al., "Detection of Structural Chromosome abberations in Metaphase . . . " *American Journal of Human Genetica*, 43, Supl. No. 3, Abstracts (1988).

(List continued on next page.)

*Primary Examiner*—Ardin H. Marschel
*Attorney, Agent, or Firm*—Fish & Richardson P.C.

[57] ABSTRACT

Improved methodologies for in-situ hybridization and non-isotopic detection of nucleic acid sequences are provided which offer major increases of resolution, sensitivity, and simplicity unavailable in previously known techniques. The methodology is able to detect even a single-copy of a specific nucleic acid of interest under controlled conditions regardless of whether these are DNA or RNA sequences; or whether the nucleic acid sequence of interest is localized in the chromosomes, nucleus, or cytoplasm of a cell. The methods employ a variety of non-isotopic labels and detection means for rapid and reliable assays. The invention is also provided in kit form for use in the clinical/diagnostic laboratory such that a relatively unskilled person can accurately and reproducibly detect even a single-copy of a specific nucleic acid of interest.

28 Claims, 18 Drawing Sheets

OTHER PUBLICATIONS

Gray, J.V. et al., "Fluorescence Hybridization to Human Chromosome 21 Using Probes From a Charon 21 A Library" *Cytometry*, Supplement 1, Abstracts (1987).

Langegent, J.E. et al., "Use of Whole Cosmid Clones Genomic Sequences for Chromosomal Localization by Non–Radioactive In Situ Hybridization" *Hum. Genet*, 77:366–370 (1987).

Sealey, Paul G. et al., "Removal of Repeated Sequences From Hybridisation Probes" *Nucleic Acids Research*, 13:1905–1922 (1985).

Harper, Mary E. et al., "Localization of Single Copy DNA Sequences on G–Banded Human Chromosomes by in situ Hybridization" *Chromosoma*, (Berl.) 83:431–439 (1981).

Lawrence, J.B. et al., "Sensitive, High–Resolution Chromatin and Chromosome Mapping In Situ: Presence and Orientation of Two Closely Integrated Copies of EBV in a Lymphoma Line" *Cell*, 52:51–61 (1988).

Singer, R.H. et al., "Optimization of in situ Hybridization Using Isotopic and Non–Isotopic Detection Methods" *BioTechniques*, 4(3):230–250 (1986).

Pinkel, D. et al., "Cytogenic Analysis Using Quantitative, High–Sensitivity, Fluorescence Hybridization" *Proc. Natl. Acad. Sci. USA*, 83:2934–2938 (1986).

Langer–Safer, P.R. et al. "Immunological Method for Mapping Genes on Drosophila Polytene Chromosomes" *Proc. Natl. Acad. Sci. USA*, 79:4381–4385 (1982).

Manuelidis, L. et al., "Chromosomal and Nuclear Distribution of the HindIII 1.9–kb Human DNA Repeat Segment" *Chromosoma*, (Berl.) 91:28–38 (1984).

Manuelidis, L., "In Situ Detection of DNA Sequences Using Biotinylated Probes" *Focus* 7:4 4–8.

Narayanswami, S. et al., "Electron Microscopic In Situ Hybridization Using Biotinylated Probes" *Focus* 8:1 3–6.

Brigati, D.J. et al., "Detection of Viral Genomes In Cultured Cells and Paraffin–Embedded Tissue Sections Using Biotin–Labeled Hybridization Probes" *Virology*, 126:32–50 (1983).

Lawrence et al., *J. Cell. Biology*, 99 (Oct. 1984) Abstract #519.

Singer, et al., *Proc. Natl. Acad. Sci. USA*, 79:7331–7335 (1982).

Gee et al., *DNA*, 2:157–163 (1983).

Capco et al., *Developmental Biology*, 67:137–151 (1978).

Angerer et al., *Nucleic Acids Research*, 9(12):2819–2839 (1981).

Leary, J.J. et al., *Proc. Natl. Acad. Sci. U.S.A.*, 80:4045–4049 (Jul. 1983).

Kuo, M.T. et al., *Chem. Abstract*, 88(1):3872p (1978).

Brandsma, J. and G. Miller, *Proc. Natl. Acad. Sci. U.S.A.*, 11:6851–6855 (Nov. 1980).

Godard, C.M. and K.W. Jones, *Histochem.*, 65:291–300 (1980).

Lawrence, J.B. and R.H. Singer, *Nucleic Acids Research*, 13:1777–1799 (1985).

Trask, B. et al., *Science*, vol. 230 1401–1403 (Dec. 20, 1985).

NON-ISOTOPIC IN-SITU HYBRIDIZATION METHOD FOR DETECTION OF NUCLEIC ACIDS

RELATED APPLICATION

This application is a file wrapper continuing application of U.S. application Ser. No. 07/257,066, filed Oct. 13, 1988 (now abandoned), which is a continuation-in-part of U.S. Ser. No. 06/790,107, filed Oct. 22, 1985, now issued as U.S. Pat. No. 4,888,278, issued Dec. 19, 1989.

GOVERNMENT SUPPORT

Work described herein was supported by grants from the National Institutes of Health and Muscular Dystrophy Association.

BACKGROUND OF THE INVENTION

Hybridization is a general technique in which the complementary strands of deoxyribonucleic acid (hereinafter "DNA") molecules, ribonucleic acid (hereinafter "RNA") molecules, and combinations of DNA and RNA are separated into single strands and then allowed to renature or reanneal into base-paired double helices. At least three major classes of hybridization are conventionally known and used: solution hybridization which disrupts the individual cells and extracts the internal nucleic acids into solution prior to hybridization; filter or blot hybridization which transfers extracted DNA (or RNA) fragments from agarose gels to filters or blotters such as cellulose nitrate or nylon for subsequent hybridization with radioactive DNA or (RNA) and then detection of hybridization by radioautography or fluorography; and in-situ hybridization which makes possible the detection and localization of specific nucleic acid sequences directly within a structurally intact cell or cellular component where extraction of nucleic acids from the cell is undesirable. Although each of these respective hybridization techniques often employ cells, tissues, and certain reagents in common, each technique is generally viewed and accepted within this art as different and completely distinguishable from any other.

In-situ hybridization is a technique which yields both molecular and morphological information about intact individual cells and cellular parts. Rather than requiring the investigator to laboriously extract DNA and/or RNA from a heterogeneous cell population, the technique permits detection of DNA and RNA in-situ within the cellular morphology and allows the investigator to identify those particular cells or cell parts which contain specific DNA or RNA sequences of interest. This technique also allows one to determine simultaneously the biochemical and/or morphological characteristics of these cells. For this reason, the in-situ hybridization methodology has direct application for many areas of biomedical and clinical research including developmental biology, cell biology, genetics, clinical diagnosis, and pathological evaluation.

Despite the potential of in-situ hybridization as a molecular analytical technique, the development of effective protocols and procedures has been largely haphazard and disjointed. Since first described in 1969 by Gall et al., *P.N.A.S. U.S.A.,* 63:378–383 (1969); *Methods in Enzymol.,* 38:370–380 (1971), the in-situ hybridization approach has been directed towards two different morphological situations: the localization of specific nucleic acid sequences of interest in the cytoplasm of a cell; and the identification of specific nucleic acids within the nucleus and/or chromosomes of a cell.

The other major application of in-situ hybridization has been for the detection of specific nucleic acid sequences within individual chromosomes and genes; and for detection of extrachromosomal nucleic acids within the cellular nucleus or cytoplasm. These investigations have been widely applied for the detection of DNA sequences in polytene chromosomes and to the identification of highly reiterated DNA sequences in metaphase chromosomes. In recent years, some investigators have also been able to localize single-copy DNA sequences in relatively large chromosomal segments using radiolabeled probes and a statistical analysis of autoradiographic grain distributions. However, due to the scatter of radioactive disintegrations, the resolution of this approach is limited and localization of DNA is possible only within relatively large chromosomal segments in the metaphase nucleus. Futhermore, because localization of the sequence is not determined directly within a single cell, identification requires statistical analysis of the autoradiographic grain distribution in an many as 50 to 100 metaphase figures. Garson et al. (*Nucleic Acids Research,* Volume 15, Number 12, (1987), pp 4761–4771) and Landegent et al. (*Nature,* Volume 317, 12, (September 1985)) teach hybridization methods for detecting unique sequences using non-isotopic detection systems. Neither method demonstrated detection of a single copy sequence or unique sequence based upon the analysis of a single cell. A statistical analysis of many cells was necessary when analyzing the results. Because of these limitations, it has not been possible with prior art techniques to localize single or low copy sequences within the interphase nucleus.

The development and applications of in-situ hybridization had been largely qualitative rather than quantitative in nature; although several investigators have developed a quantitative approach using autoradiography for cells to which a probe had been hybridized methods were typically limited to testing only a very few samples at one time and were enormously time consuming and laborious procedures. Equally important, protocol parameters such as choice of fixation, the need for cell pretreatment prior to hybridization, the size of the probes utilized, the concentration of probe, and the time required for hybridization varied markedly among the different protocols published. Moreover, the then known protocols were also highly complex procedures requiring many manipulative steps, all too many of which are actually destructive to the cell by their ability to dissociate either the nucleic acid components within the cell and/or the structural morphology and overall integrity of the cell. Further, the known protocols varied extensively in their sensitivity limits, their reproducibility, and their general effectiveness.

In U.S. Pat. No. 4,888,278, issued Dec. 19, 1989, we describe a rapid in-situ hybridization method for detecting target nucelic acid sequences in morphologically intact cells. The teachings of this patent are hereby incorporated herein by reference.

SUMMARY OF THE INVENTION

The present invention is a rapid non-isotopic method for detecting a target nucleic acid sequence in a cellular sample containing nucleic acid with a nucleic acid probe, comprising:

a) fixing said nucleic acid in said cellular sample to allow the nucleic acid probe to hybridize to the target nucleic acid sequence;

b) contacting said cellular sample with the nucleic acid probe for less than about 24 hours under conditions whereby said probe hybridizes to the target nucleic acid sequence, said probe consisting essentially of a multiplicity of non-isotopically labelled nucleic acid fragments complementary to a portion of said target nucleic acid sequence, said fragments having from about 20 to about 1000 nucleotides;

c) detecting said labelled probe.

This rapid, non-isotopic in situ hybridization method provides exceptionally high hybridization efficiency, low background, and high resolution. Indeed, it provides the capability to detect a single copy of a single nucleic acid sequence within a single cell.

BRIEF DESCRIPTION OF THE DRAWINGS

FIGS. 5A, C and E show fluorescein-avidin detection of hybridized probe. FIGS. 5B, D and F used DAPI fluorescence staining for total DNA. The arrows indicate the position of label on chromosome 1. The probes used were for BamHI W (21–30 kb) (FIGS. 5A and B), BamHI A (FIGS. 5C and D) and BamHI Y/H (7 kb) (FIGS. 5E and F).

FIGS. 6A, 6C, 6D and 6E show fluorescein-avidin detection of hybridized porbes. FIGS. 6B and 6F use DAPI fluorescence straining of total DNA. Sequences were detected with BamHI W probe (FIGS. 6A and 6B; note that the smaller G1 cell has one pair of closely spaced spots whereas the larger, G2 or tetraploid cell has two pairs of spots; magnification 1600x) or BamHI K probe (FIGS. 6E and 6F; each spot represents hybridization to 5 kb of target DNA; 1600x magnification ). FIG. 6D is a randomly selected field that shows many nuclei hybridized with the W probe (magnification 700x). FIG. 6D shows nucleus hybridized simultaneously with W and A probes and shows the presence of four tightly clustered spots of two different fluorsecent intensities (magnification 2450x).

Biotinated probes were hybridized in situ and specific hybridization detected with fluorescein avidin. Total DNA was stained with either propidium iodide or DAPI.

A) Track of EBV Bam H1 W RNA within interphase nuclei from a cytogenetic preparation of Namalwa cells.

B) Same as in A, except nuclear stain was DAPI.

C) Simultaneous hybridization to viral RNA and DNA with the W probe in samples that had been denatured to allow DNA hybridization. Tiny spots of yellow fluorescence on each sister chromatid of chromosome 1 indicate the localization of the integrated EBV genome. Interphase nuclei show larger fluorescent signals, indicative of Bam W RNA (compare to A).

D) Hybridization to Bam W DNA in denatured, RNAase treated samples. Signal at interphase appears as just two closely spaced tiny fluorescent spots indicative of the two closely-integrated EBV genomes. Due to increased chromatin condensation, on metaphase chromosomes the two fluorescent spots coalesce into one signal on each of the two sister chromatids.

E & F) Hybridization to Bam W RNA in non-denatured sample. In the absence of denaturation, no hybridization to chromosomal DNA is detected, but RNA signal within the nucleus is still apparent.

E) DAPI DNA stain

F) Fluorescein-avidin detection of hybridization

G) Hybridization to Bam W RNA in non-denatured nuclei of paraformaldehyde-fixed intact Namalwa cells.

H) Hybridization to neuoncogene (erb B2) RNA in 3T3 cells transfected with a plasmid containing the neuoncogene. Foci of nuclear RNA are apparent and punctate staining throughout the cytoplasm indicates cytoplasmic mRNA.

Figure 8:
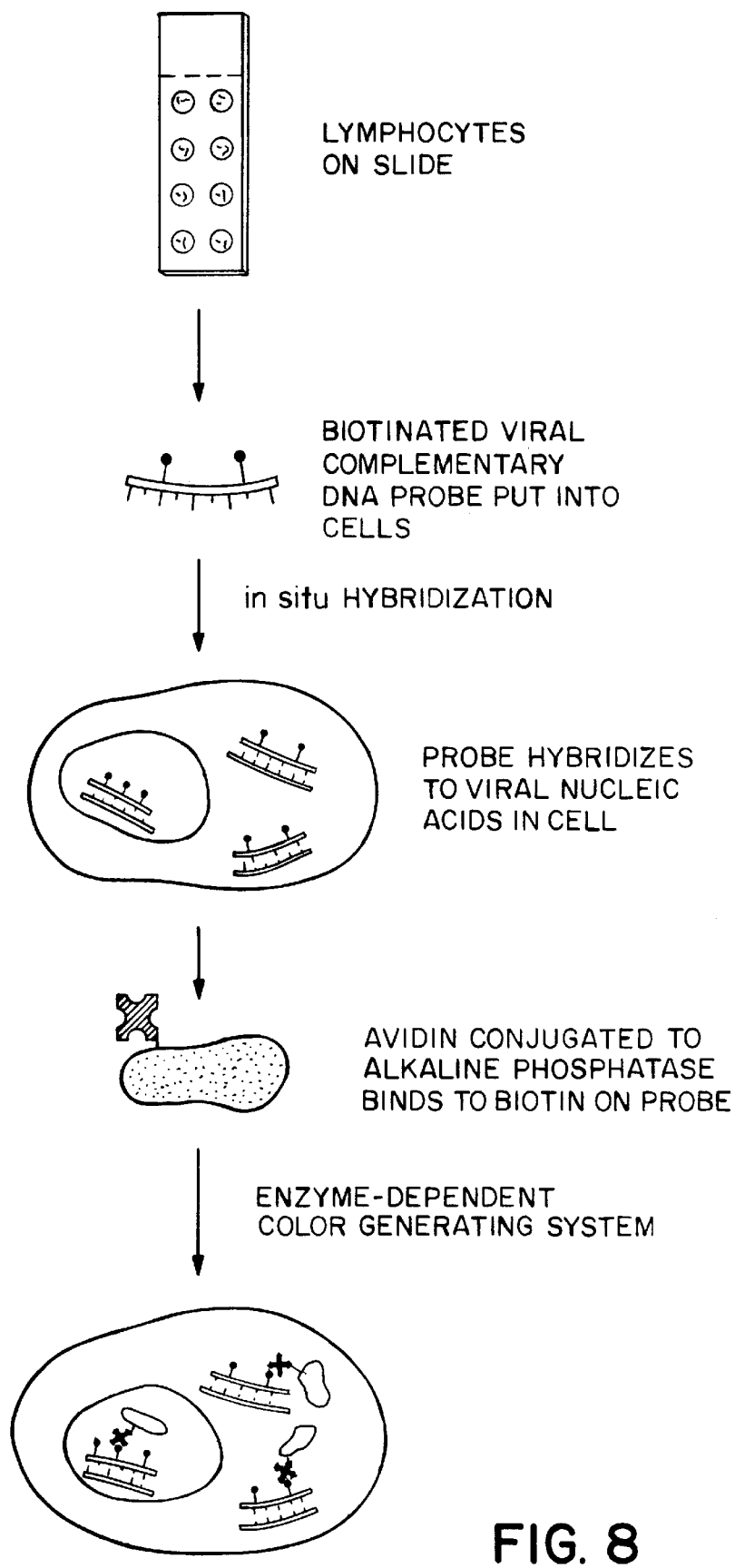

FIG. 8 is a schematic diagram of a preferred embodiment of the present methodology for specific non-isotopic detection of HIV.

Figure 1:
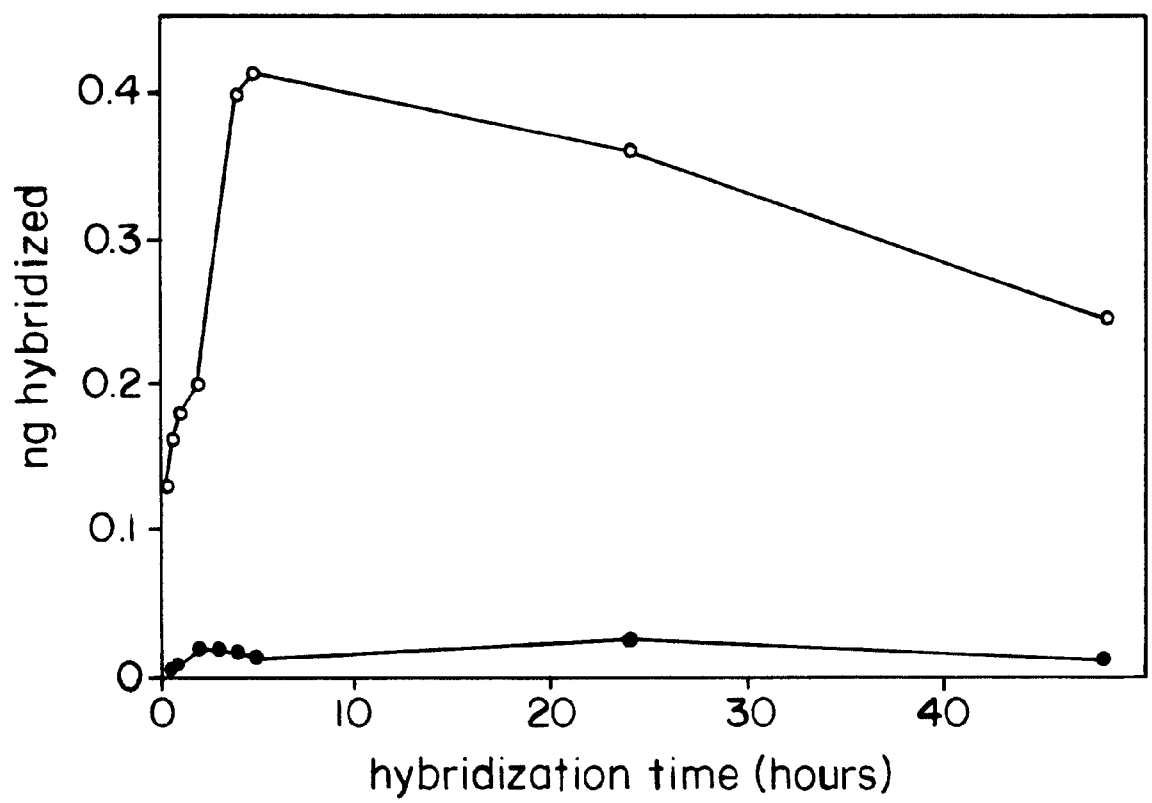
FIG. 1 is a graph illustrating the kinetics of the in situ hybridization process.
Figure 2:
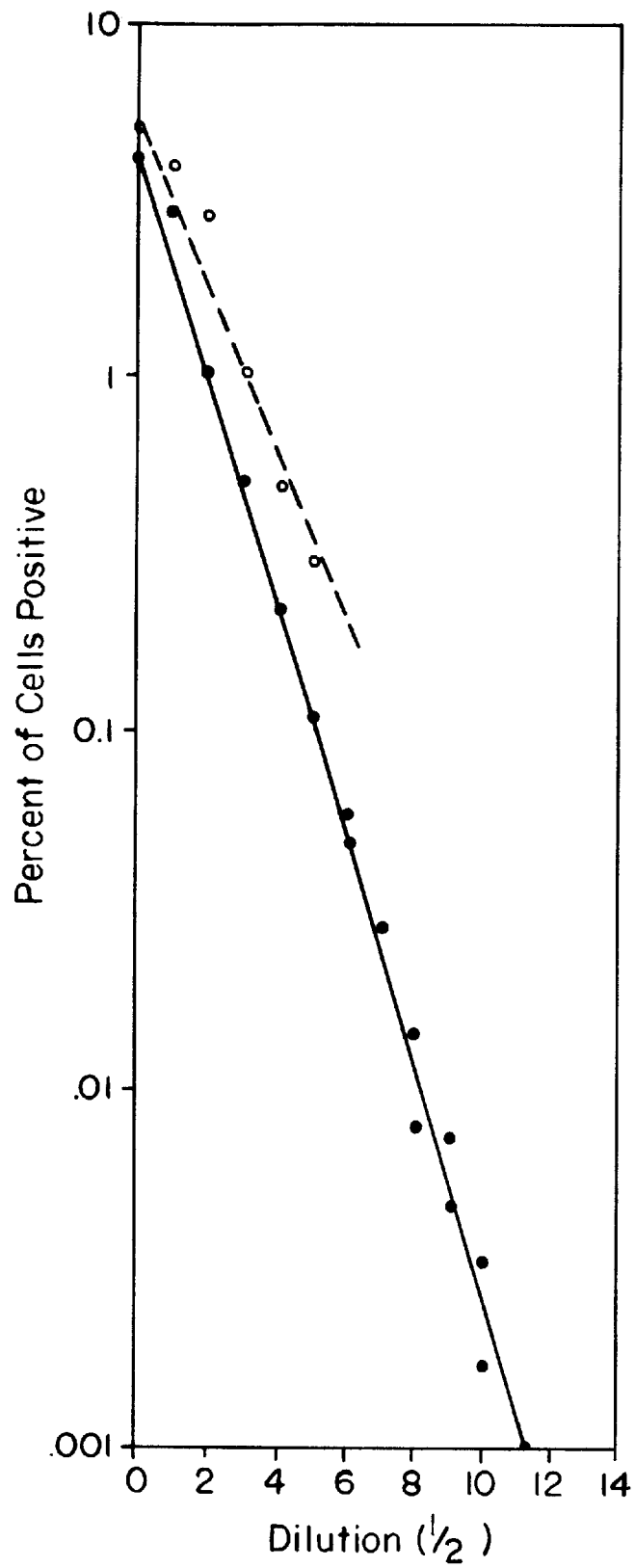
FIG. 2 is a graph illustrating the detection of serially diluted HIV infected cells.
Figure 3:
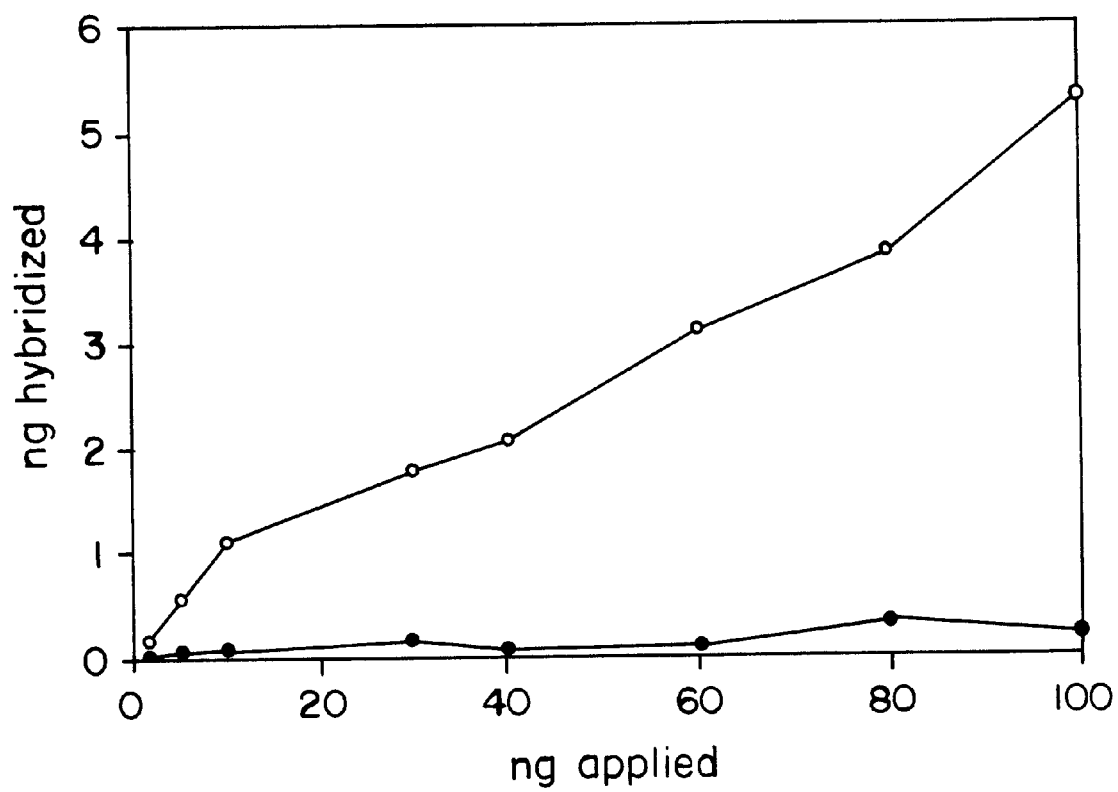
FIG. 3 is a graph illustrating the effect of high concentrations of probe with respect to background signal and in situ hybridization efficiency.
Figure 4:
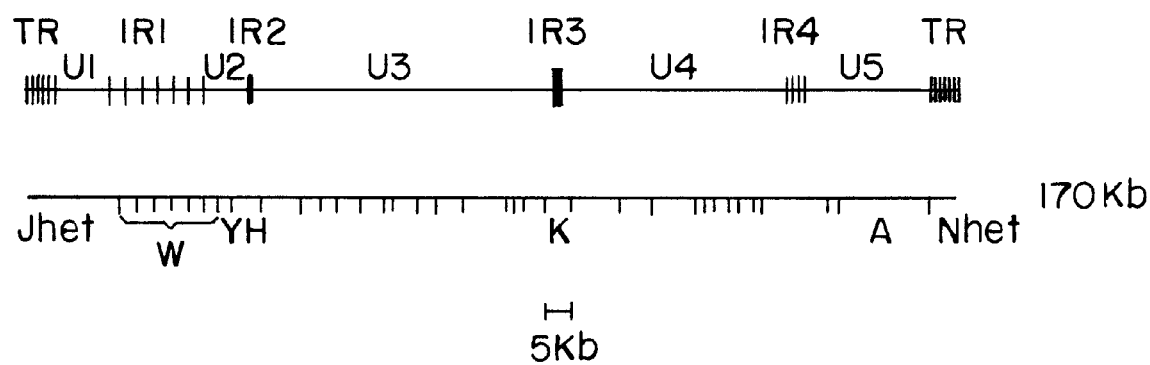
FIG. 4 is the restriction map of the Epstein-Barr virus genome indicating the Bam HI restriction fragments. This map was modified from Henderson et at., Proc. Natl. Acad. Sci. USA, 80:1987–1991 (1983). The nomenclature is in accord with that of Skare and Strominger, Proc. Natl. Acad. Sci. USA., 77:3860–3864 (1980) from whom the clones are derived. Only those fragments that were used as hybridization probes are indicated on the map.
Figure 9:
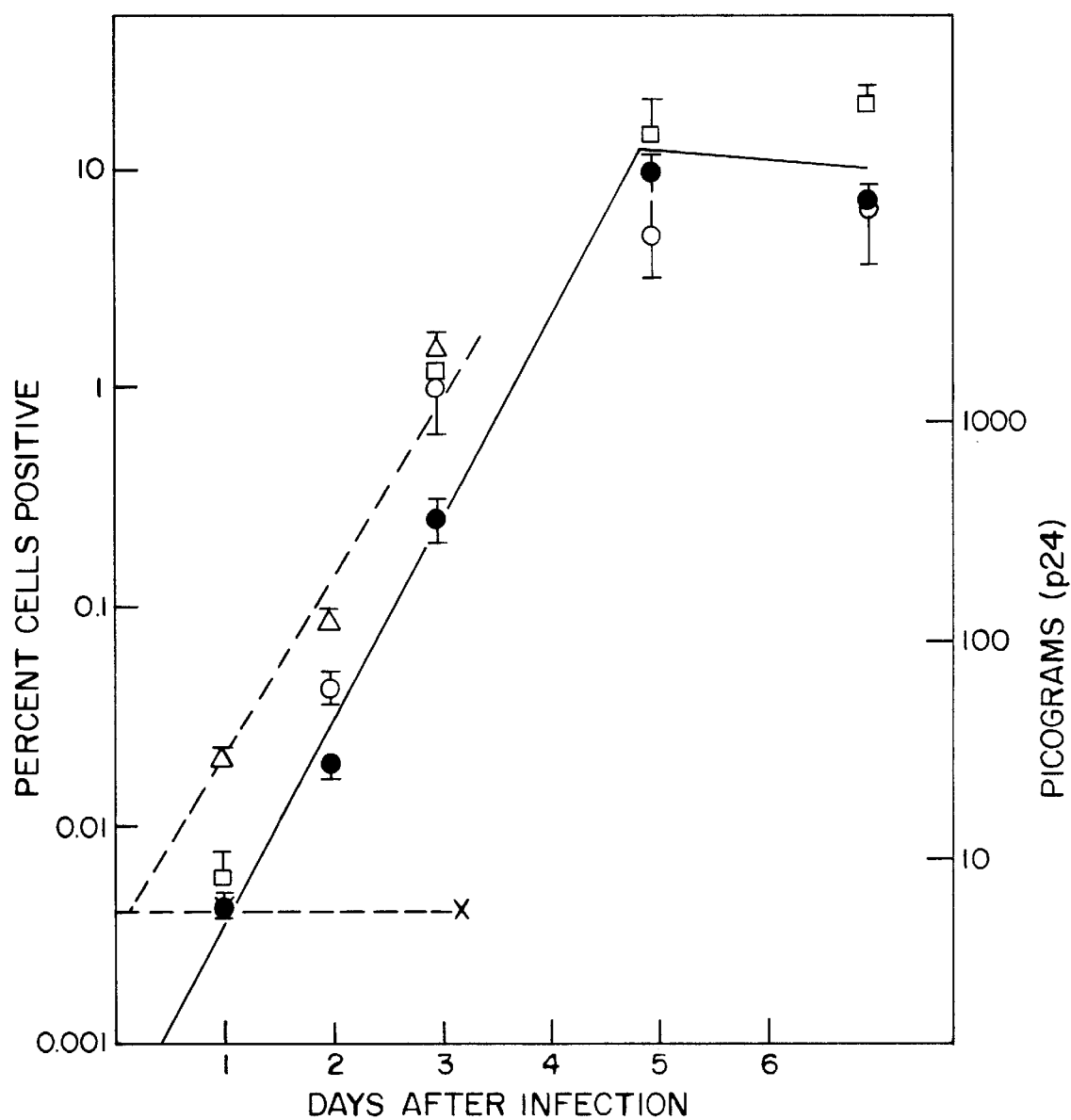

FIG. 9 illustrates the kinetics of infection of normal T lymphocytes comparison of various means of detecting in situ hybridization. Three methods of in situ hybridization were used: isotopically labelled probe ($3 \times 10^8$ cpm using $^{35}$S-dNTP); non-isotopically labelled probe (open circle) and conjugated oligonucleotides (closed circle). Normal T lymphocytes were cultured in vitro for 3 days with IL2 and PHA and then were infected with HIV at very low MOI. At daily intervals, including just after exposure to the virus (day 0), aliquots were taken for in situ hybridization as described in FIG. 1. Autoradiography was used for 3 days. In addition, p24 was measured in the supernatant of the culture using an ELISA method (Dupont). Briefly 200 ul of supernatant was used for the assay after the method in the ELISA manual and was done with a Dupont representative present. Control (uninfected cells) were detected at day 0, 1 and 3 for the ELISA assay for p24 (x - - - x) and for this in situ hybridization, the results were 0 cells positive on days 0 and day 3.

Probes obtained from MBI (Dupont SNAP probe) were used at a concentration of 1 ng per hybridization (b nM concentration). Probes were hybridized in 5xSSC, 0.5% SDS and 1% BSA at 50° C. for twenty minutes in a humidified environment. Samples were then washed at 42° C. for 5 minutes in 1xSSC at room temperature for five minutes each. The detection of the alkaline phosphatase was as above.

Figure 10:
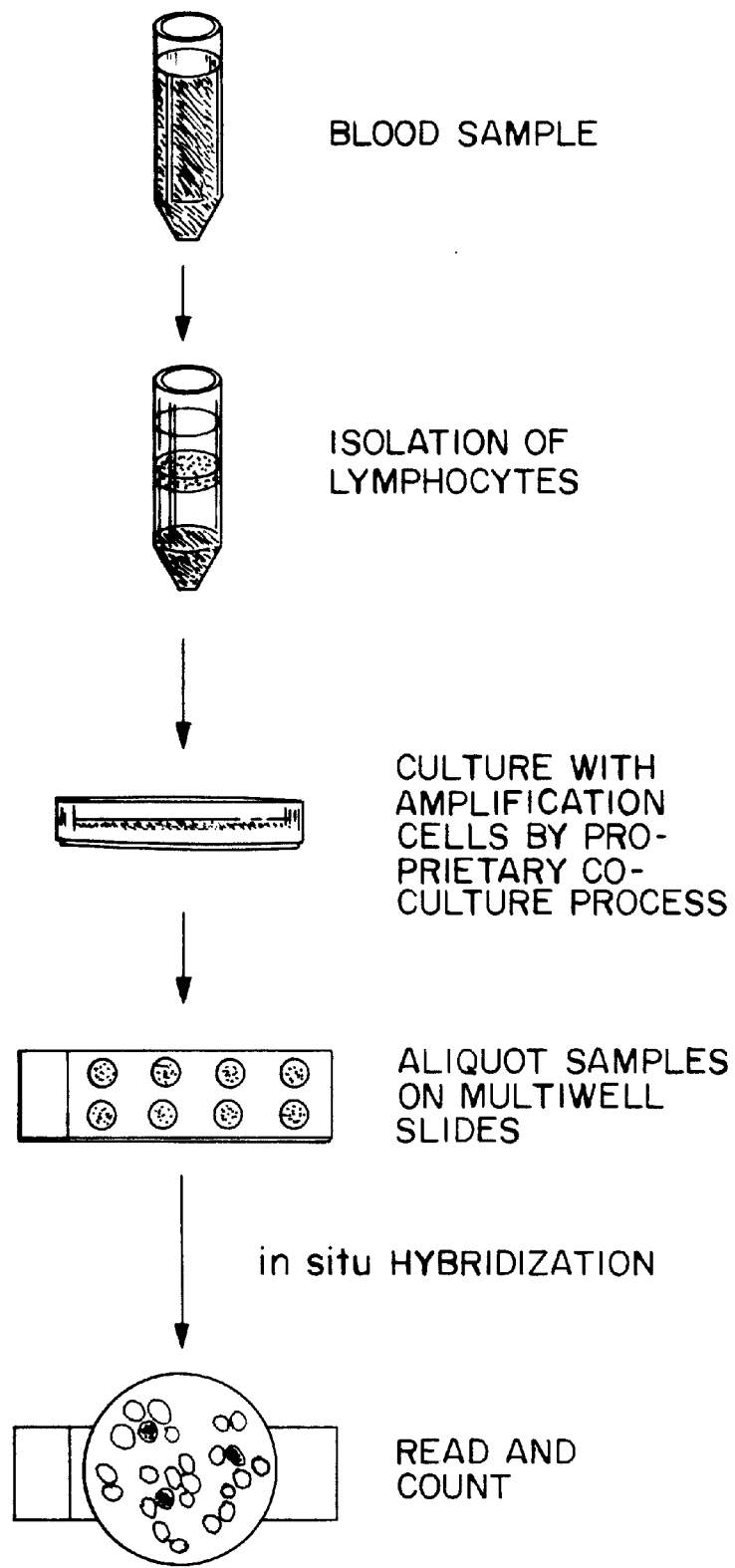
Figure 11:
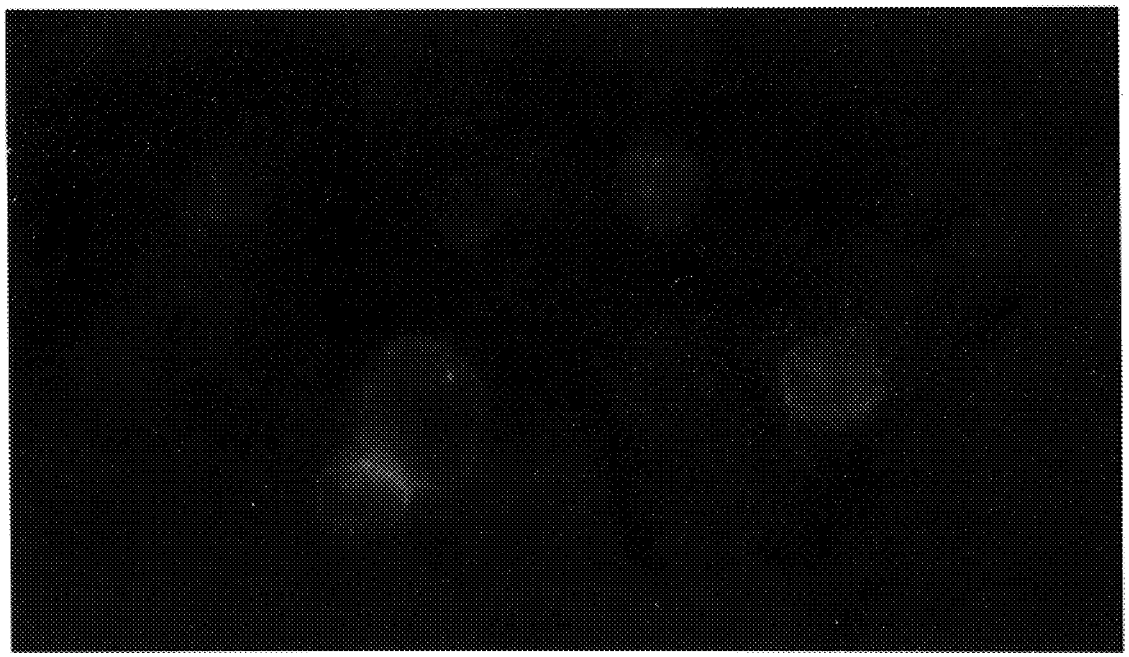

FIG. 10 is a schematic diagram of the co-culture technique useful with in-situ hybridization for effective non-isotopic detection of HIV;

FIG. 11 is a photograph illustrating the "focus of replication" for HIV within a nucleus. A focus of very intense fluorescence was observed in most positive cells indicating a highly localized concentration of HIV sequences. The nuclear DNA was stained with DAPI and HIV probe hybridization was detected with fluorescein. There were no positive cells or foci seen in uninfected cultures or in samples hybridized with Epstein-Barr virus or pBR 322 probe.

Figure 12:
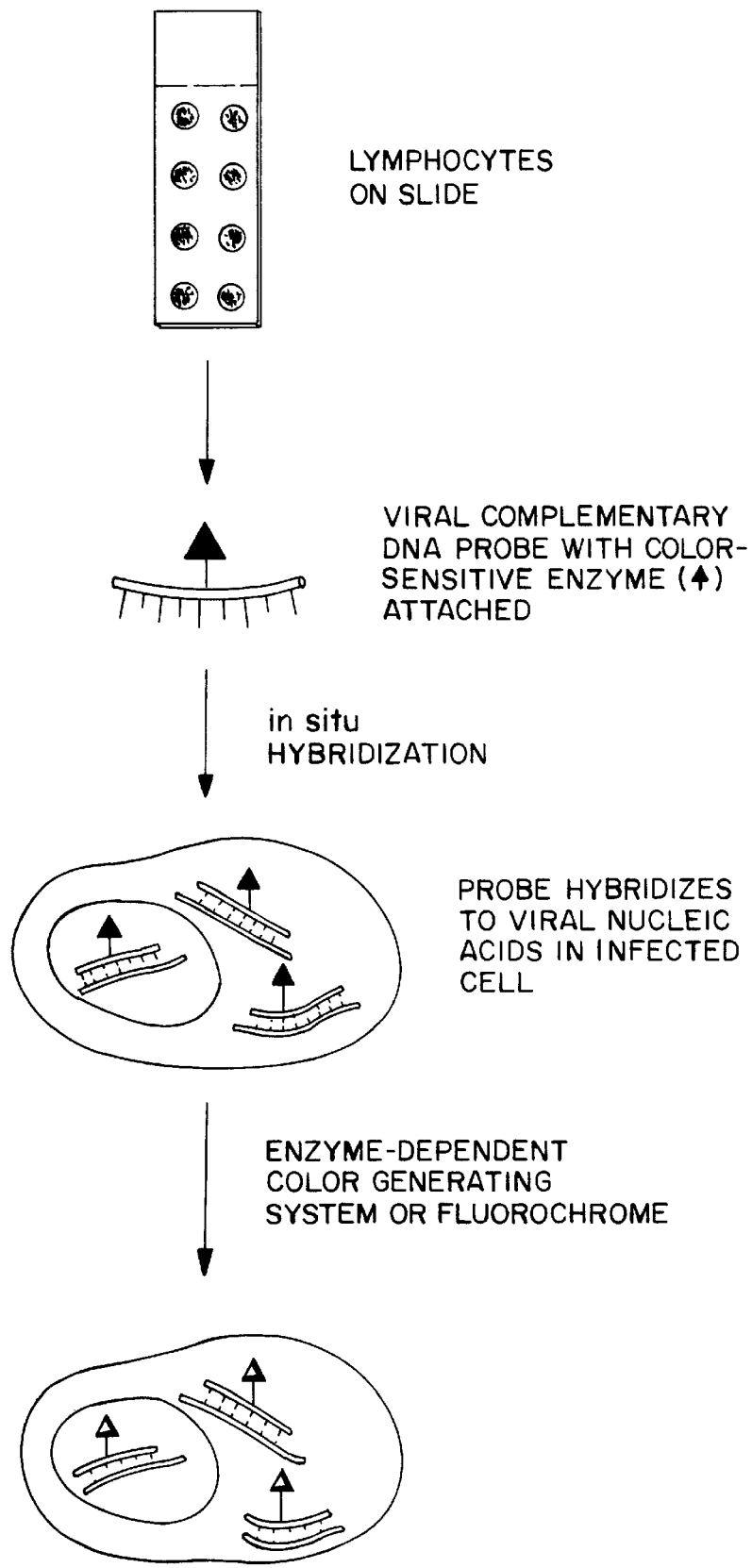

FIG. 12 is a schematic diagram of the detection of cells infected with HIV using alkaline phosphatase conjugated oligonucleotides.

Figure 13:
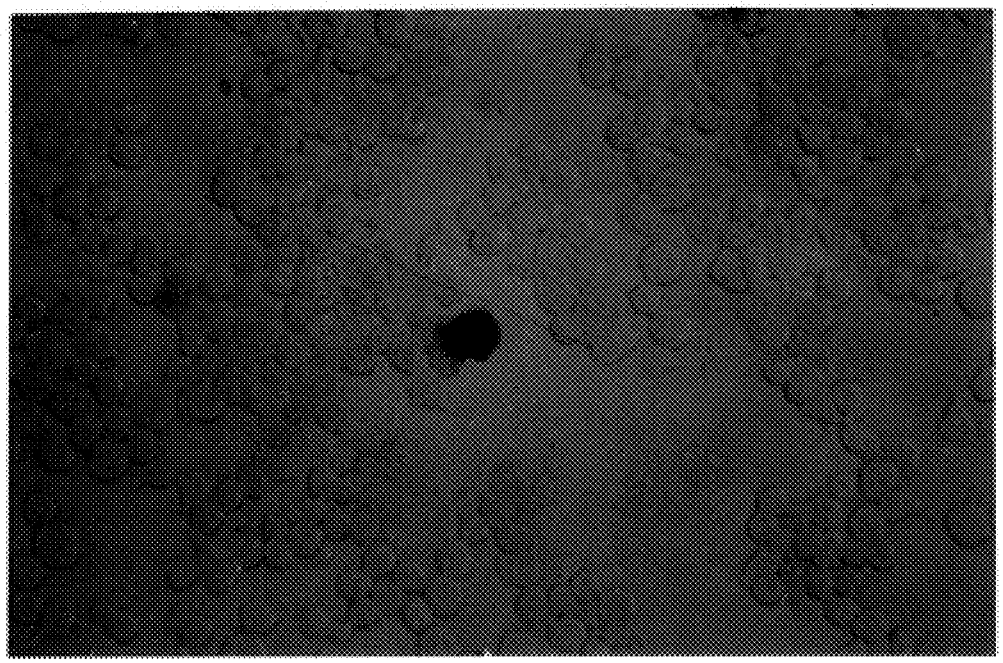

FIG. 13 is a photograph showing alkaline phosphatase detection of HIV infected cells.

FIGS. 14A–14H presents photographs of examples of human gene detection.

A) Dystrophin in W138 Nuclei. Two phage clones for 10–15 kb sequences separated by 700 kb (from JMD and J-Bir, FIG. 8) were hybridized to nuclei of intact W138 cells. Linkage between these two sequences is immediately apparent in the G1 interphase nucleus (cytoplasm is not visible). W138 cells have two X chromosomes, so two pairs of signals are observed. Note the equivalence in signal intensity and distance between paired spots for the two homologs.

B) MHC Sequences in W138 Nuclei. Same cell type and experiment as in A, except probe used hybridized to the 5' end of the alpha and beta MHC genes, separated by only 28 kb. The interphase distance between these very tightly linked genes is just within the resolution of the light microscope.

C) Dystrophin Sequences in Namalwa. The same probes as in A except hybridization was to cytogenetic preparations of the Namalwa cell line. Two nuclei show closely paired signals and the X chromosome shows signal on each chromatid. We consistently detect hybridization to only one X chromosome in this cell line, which has been reported to have one intact X and one rearranged X.

D) Cosmid Clone to Neu Oncogene. Hybridization of two overlapping cosmid clones (60 kb target) results in one bright signal for each Chr. 17 homolog. Genes on homologous chromosomes are not closely paired. Because the neu oncogene is more centrally localized at interphase than other genes we have examined, this represents the closest localization of homologs that we have observed.

E) Double Hybridization to Neu Oncogene and HMC. The large neu oncogene target (roughly 60 kb) on Chr. 17 produces a brighter signal than the cardiac MHC genes (13 kb probe) 0 Chromosome 14.

F) Propidium Iodide Staining of Same Metaphase as in E.

G and H) Banding Patterns Produced by Hybridization to Repetitive DNA. These photographs illustrate the strong repetitive hybridization obtained with G) neu oncogene cosmid probe or H) MHC probe if cold competitor genomic DNA is not added to the hybridization. FIGS. A–E all represent hybridization to which cold competitor DNA was added.

Figure 15:
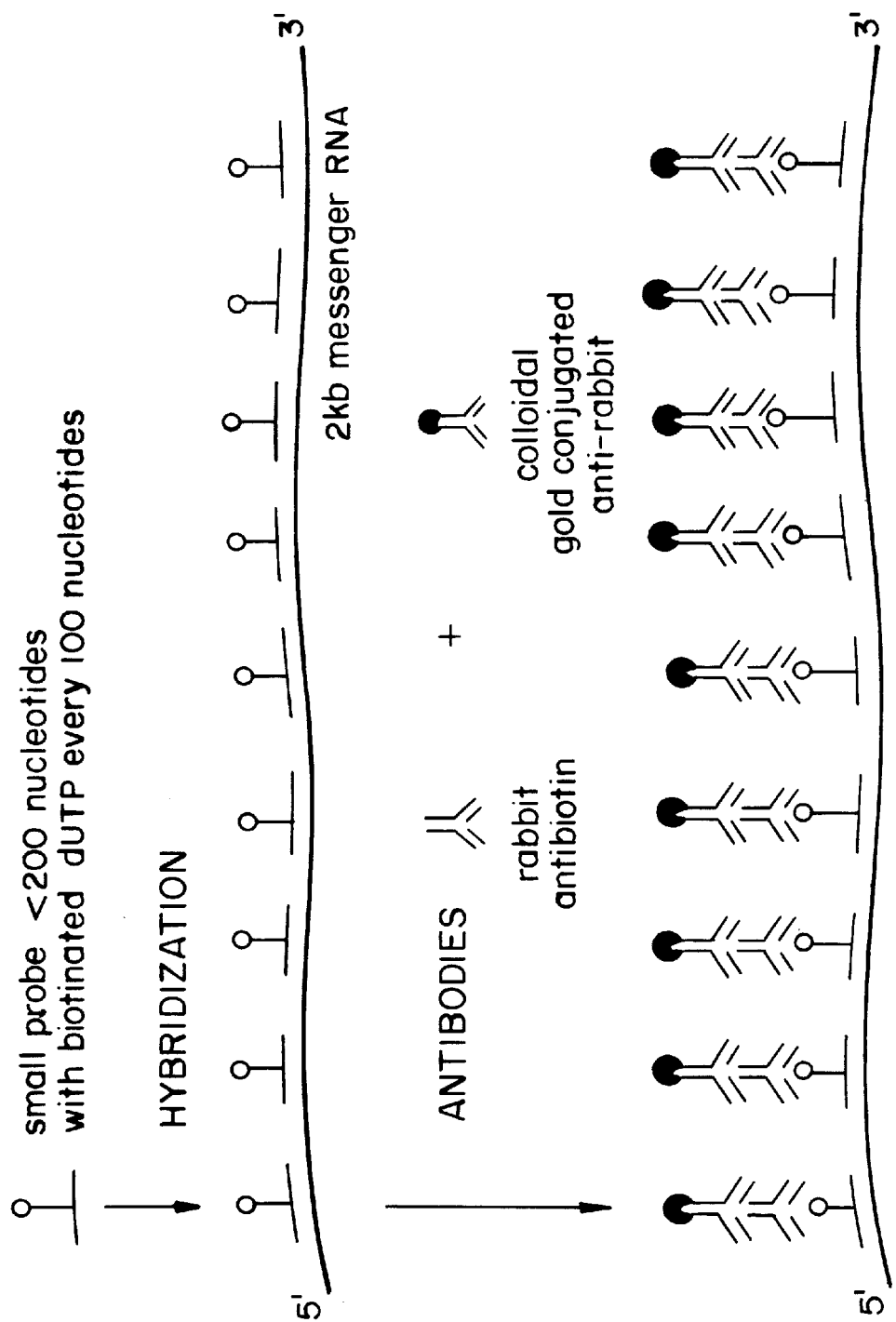

FIG. 15 is a schematic illustration showing the iterative detection of a mRNA molecule using a biotinated DNA probe cut into small fragments so that each segment hybridizes independently. When the antibody detection of the biotin groups results in a string of colloidal gold particles is detected, this distinguishes the signal from the noise generated by non-specific sticking, either of probe or of antibody. The antibody detection of the biotin is not intended to represent the actual mode by which antibodies recognize determinants but rather to explain the date which indicates that one colloidal gold particle represents the detection of one biotin.

Figure 16:
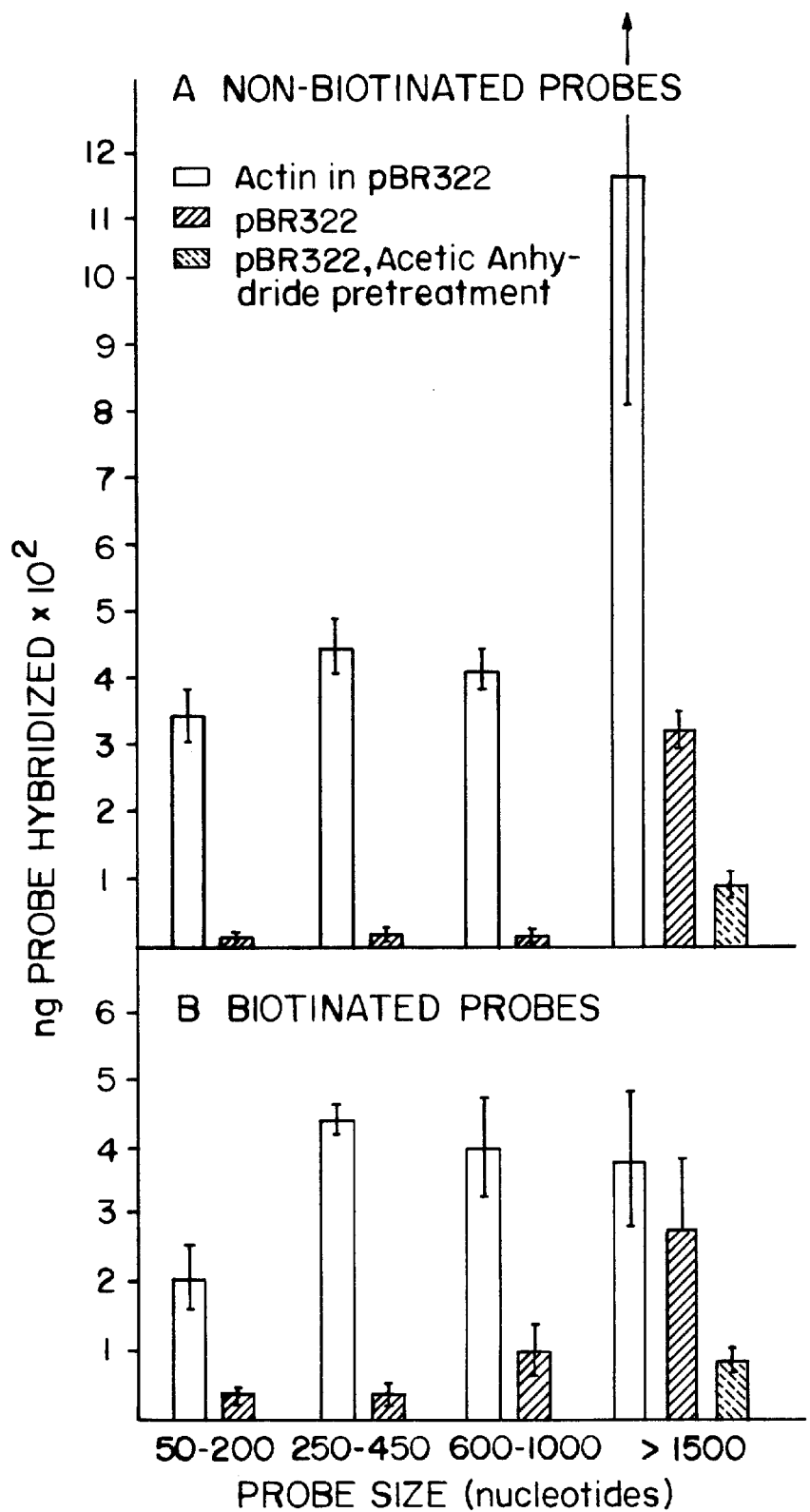

FIG. 16 is a graph illustrating the effect of probe size on hybridization and background. Results presented are from two experiments each of which utilized duplicate samples, bars indicate standard deviations. (A) probes labeled with $^{32}$P. (B) probes labeled with biotin. Probe size was varied by changing DNAase concentration in the nick-translation.

Figure 17:
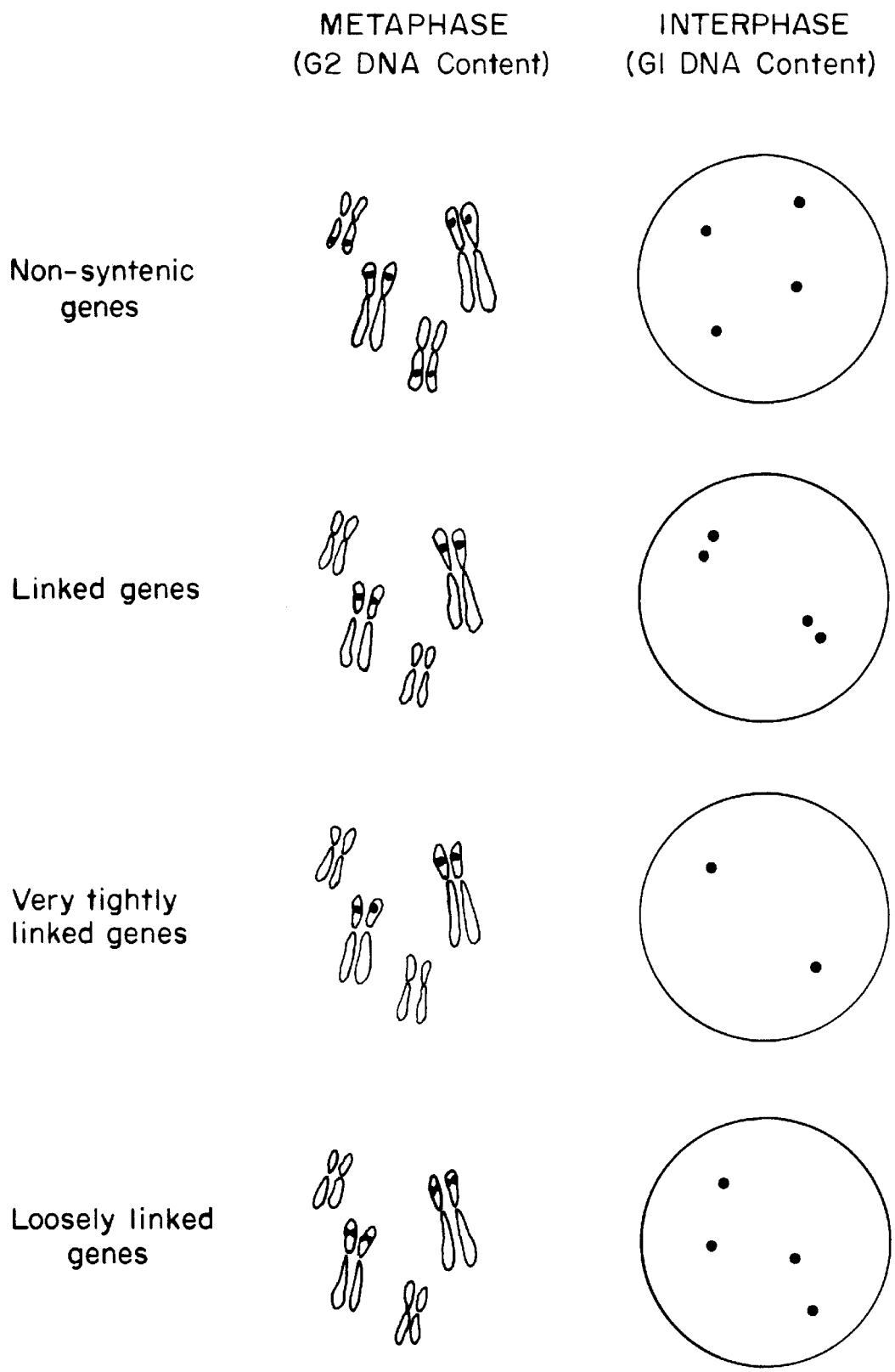

FIG. 17 is a schematic diagram illustrating interphase chromatin mapping. Hypothetical results of simultaneous hybridization with two single-copy probes, showing different linkage relationships. Note that in the loosely-linked category the two genes are resolvable as two distinct signals on each sister chromatid at metaphase.

DETAILED DESCRIPTION

The in-situ hybridization and detection methods of the present invention are used to detect DNA and/or RNA target nucleic acid sequences using nucleic acid probes within cytoplasmic nuclei, whole cells, microorganisms, tissues, etc.

Target Nucleic Acid Sequence

The target nucleic acid sequence (hereinafter TNA sequence) is defined as the nucleic acid sequence of interest in a sample which is to be detected. The TNA sequence can be a single-copy nucleic acid sequence or repetitive nucleic acid sequences in a series within the nucleus or cytoplasm of a cell. The TNA sequence can be either deoxyribose nucleic acid (DNA) or ribose nucleic acid (RNA), or both DNA and RNA concurrently.

The TNA sequence can be derived from any source of nucleic acid and it can be either endogenous or exogenous to the sample to be tested. Target DNA sequences can exist within the chromatin and chromosomes of a eukaryotic nucleus as integrated DNA strands, as extra-chromosomal DNA segments within the nucleus, and as cytoplasmic DNA sequences within procaryotic and eukaryotic cells. The DNA can be detected in either single-stranded or double stranded form. Target RNA sequences in single copy or multiple copies can be detected within either the nucleus or the cytoplasm of a cell.

Regardless of whether the TNA sequence is DNA or RNA, the method of this invention provides the capability to directly detect a single copy sequence within a single cell, i.e., without image processing or statistical analysis of multiple cells.

Sample

The sample containing the target nucleic acid sequence can be prepared cellular nuclei, morphologically intact cells (or tissues), or chromosomes, or other cellular material or components. The sample may be obtained ex vivo or maintained in vitro. The sample may be obtained from the fluids or tissues of a mammal, preferably human or plants which are suspected of being afflicted with a disease or disorder either biopsy or post-mortem. The specific target DNA or RNA sequence of interest may be endogenous to the cell sample or be exogenous nucleic acid sequences from a virus, bacteria, plasmid, or any other source of exogenous nucleic acid sequences.

Prepared cellular nuclei used as the test sample can be made in the following manner. Cells and tissues obtained ex vivo and cells maintained in culture are preferably suspended in RPMI medium containing 10% fetal calf serum and 0.1% gentamycin. Actively growing cell cultures are preferably incubated at 37° C. with 0.015 ug/ml of colcemid (demicolcine) for preferably between 2–4 hours. These cells are then harvested and incubated preferably in 0.075 M KCl at 37° C. for about twenty minutes. This can be followed by the fixation of the cells and the freezing and drying of the cells to provide prepared nuclei. It is an important teaching of this inveniton that the presentation of nuclear material is significantly improved by dry, cold or frozen storage of samples; avoidance of degradative RNAase or proteinase prior to denaturation; use of the minimal heat or alkali of treatment of DNA which provides effective denaturation of sample DNA; and hybridization for hours rather than days.

When whole morphologically intact cells are to be maintained and used as the test sample, it is preferred that actively growing cultures be used. Such cultures are preferably plated at a density of $2.0 \times 10^6$ in 100 mm plates containing glass coverslips of approximately 22 sq. mm surface area previously autoclaved in 0.5% gelatin. The culture medium is preferably Minimal Essential Medium and 10% fetal calf serum. The cells are maintained in this medium at 37° C. in a 5% $CO_2$ environment for between 2–3 days. The sample is preferably specific cell lines and cloned cell lines of various types and origins, preferably normal and abnormal cell lines derived from human sources such as the Namalwa lymphoma cell line and the W138 lymphoma cell line.

Fixation of Cellular Nuclei and Chromosomes

The purpose of fixing cellular nuclei or chromosomes is to preserve the nucleic acids in such a manner that the DNA and/or RNA is retained and preserved for in situ hybridization. Many fixatives commonly employed cause over-extensive insolubilization of the proteins within the sample matrix via crosslinking and or precipitation of the proteins which renders the sample impermeable to all but small sized probes. Thus, the preferred fixative is one which maintains and preserves the nucleic acids within a nucleus while allowing an efficient degree of probe penetration by restricting the crosslinking and/or precipitation of proteins in the sample. The preferred fixative for nuclei preparations is a mixture of methanol and acetic acid in a 3:1 volumetric ratio.

A sample of prepared nuclei or chromosomes can be fixed using three changes of fresh 3:1 methanol:acetic acid using conventional DNA cytogenetic techniques. The nuclei or cells in suspension can then be dropped onto clear glass cover slips in a humid environment to promote chromosome spreading. The coverslips can then be air dried overnight and stored at −80° C. with dessicant until required for use.

Fixation of Morphologically Intact Cells

The preferred fixative for preserving and retaining the nucleic acids within a morphologically intact cell is paraformaldehyde. Paraformaldehyde is a solid formaldehyde polymer which can be solubilized by dissolving the solid as a 4% solution in phosphate buffered saline containing 5 mM $MgCl_2$. If the paraformaldehyde is allowed to age over a period of weeks, it breaks down into several substances, at least one of which is destructive to cellular DNA and/or RNA.

Post-fixative Steps of Chromosomes

Immediately prior to hybridization, the dried chromosome preparations can be baked for approximately 3 hours at 60° C. to promote drying and hardening of nuclear material. The nucleic acids are also preserved and retained in a form which allows in-situ hybridization to occur in an efficient manner.

Slides can be stored frozen at −80° C. with dessicant. After freezing, the baking at an elevated temperature (above 40° C.) for a limited number of hours serves to maintain the morphological integrity of the individual chromosomes thereby retaining and preserving their nucleic acid constituent throughout denaturation and hybridization procedures. As regards the choice of fixatives for fixing the deoxynucleic acids, a wide variety of alternatives are available for use at varying concentrations and ratios. These preferably include the use of paraformaldehyde at concentrations ranging from 1–4% by volume.

Denaturation of the Fixed Sample

When the TNA sequence is a DNA sequence, denaturation of the DNA in the sample can be carried out using conventional techniques such as melting or alkali denaturation. See Harper et al., *PNAS USA*, 78, 4458–60 (1981), pp 175–177 for alkali denaturation and Gall et al, *PNAS USA*, 63:370–383 (1969). The denaturing of the DNA in the sample is carried out so that the DNA strands are melted with minimal destruction to the DNA.

The Hybridization Fluid Composition

The hybridization fluid composition can be a mixture of components important to both the degree and detection of in-situ hybridization. The composition not only provides components necessary for hybridization to occur, it can also provide components which reduce the background signal (caused by non-specific binding) of the non-isotopically labelled probe for purposes of subsequent detection in an accurate and precise manner.

The hybridization fluid can comprise several components. Initially, of course, it contains a non-isotopically labelled probe able to hybridize at least in part to the nucleic acid sequence of interest to be detected. It can also contain a non-specific nucleic acid competitor when hybridizing to a probe which contains significant repetitive sequences. The non-specific competitor should contain repetitive sequences homologous to the repetitive sequences of the probes. An example of such a repetitive sequence would be the alu sequence of the human genome. The fluid can also contain a soluble salt and an ionizing solvent. Each of these components will be described individually in detail.

Interrelationship Between Parameters

An important aspect of the present invention is the interrelationship between parameters (probe size, probe concentration, choice of fixative, and choice of probe label) which render an end result of a significantly improved signal to noise ratio. A signal to noise ratio is defined as a ratio of the probability of the spot being a bona fide signal of hybridization of the target nucleic acid sequence to that of the probability of the spot being representative of the background caused by non-specific binding of the labelled probe. A method wherein the background signal is difficult to distinguish from the signal representative of the target nucleic acid is not very useful. Statistical analyses would have to be performed which are very labor intensive to determine which signal was representative of the desired target nucleic acid and which represented noise due to non-specific binding. The present method allows detection of a target nucleic acid sequence within a single cell with high confidence without the laborious statistical analysis step.

The signal to noise ratio is especially important to in-situ hybridization within chromosomes where the probe hybridized to sister chromatids is distinguishable as a pair of signals. This paired signal significantly improves the signal to noise ratio over prior results. Further, since it is impossible randomly to place a set of fluorescent or chromogenic spots exactly opposite one another within a chromosome pair, this paired signal also affirms with high confidence that the spots are representative of bona fide hybridization of the target nucleic acid sequences. This observation and phenomenon was not previously possible in the art because prior techniques did not provide sufficient resolution of signal and, therefore, could not make such a detection. It will be appreciated also in this regard that the sensitivity of detection can also be even further increased via the use of video imaging processing equipment which is far more sensitive to signal than mere observation with the unaided eye or a light microscope. The use of such image processing instrumentation with its concomitant increased sensitivity in combination with analyses of sister chromatids thus significantly increases the detection capability. This permits detection of nucleic acid sequences which are only about 0.2 kb (200 bases) in size. Some of the parameters contributing to the significantly improved signal:noise ratio will be described individually in detail below.

Probes

The probe can be a DNA or RNA fragment ranging in size from about 20 to about 1,000 nucleotides, preferably ranging in size from about 100 to about 700 nucleotides. The probes used herein can be prepared using conventional techniques. They can be synthesized chemically or preferably be prepared using the method of nick-translation. Plasmid DNA can be nick-translated in the conventional manner using a reactant comprising the identifying label of choice conjugated to a nucleotide such as DATP or dUTP (Rigby et al., *J. Mol. Biol.*, 113:237–251 (1977). Nick-translations utilize endonuclease free DNA polymerase I (Boehringer Mannheim). Subsequently, each labelled plasmid is combined with DNAse in quantities varying from 1.0–300.0 ng/ml which yields a variety of labelled probe fragments of different nucleotide sizes. Thus, the probe of this invention consists essentially of a multiplicity of non-isotopically labelled nucleic acid fragments complementary to a portion of said target nucleic acid sequence, each fragment having from about 20–1,000 nucleotides.

The size of the probe molecules after labelling affects the success of the in-situ hybridization process in several interactive respects. It is a novel and non-obvious feature of this invention that these different effects were identified and their complex interrelationships characterized to define a specific range of probe sizes that could be used successfully to produce high signal-to-noise ratios. This resulted in the exceptional results presented here whereby a single gene is unequivocally detected within a single cell. This will be elaborated upon in detail below.

When using the nick-translation method for preparing probes, a variety of different sized probes are obtained by varying the amount of DNAse from 1.0 ng/ml to 300 ng/ml such that the lowest concentration yields fragments with a mass average molecular size of 2,000 nucleotides and the greatest concentration yields fragments averaging 100 nucleotides in length. The probe fragments can be isolated and selected for a particular size range using 1.5% alkaline agarose gel electrophoresis with appropriate molecular weight markers (Boehringer Mannheim Biochemical Company). This size selection step has not been taught in prior methods since it was not appreciated how important probe size can be to an in situ hybridization process. With fixed nuclei and intact whole cells, a probe fragment sizes ranging from about 20 to about 1,000 nucleotides are useful and acceptable. The size of probe will vary with respect to whether the target nucleic acid sequence is in the cytoplasm or nucleus. When using fluorescent labels directly joined to the probe nucleotides, the preferred size is in the range of about 100 to about 700 nucleotides. With biotinylated probes, the probe fragments can be smaller in size since the biotin label makes the probe stickier particularly to cytoplasmic nucleic acid (i.e., sticks non-specifically rather than hybridizing to the target nucleic acid sequence of interest).

Also, an RNA probe can be used into which the identifying label is incorporated by a DNA dependent RNA-polymerase. When these probes are used an RNA step must be introduced to eliminate background.

Under normal use conditions, it is not required that labelled fragments be of a uniformly single length. It is desirable that the DNA containing plasmid (acting as the source of nucleotides for the probe) be individually combined with varying quantities of DNAse to yield a mixture of differently sized fragments ranging from about 100 to about 1,000 nucleotides.

It has been unappreciated in the art that the fragment length of the probe (the size of one piece of nucleic acid fragment after nick-translation or synthesization of a probe by other means) is an important factor to the success and the reproducibility of hybridization to cellular target nucleic acid. There are four major effects of the probe size: the ability to penetrate within the sample such that all cellular targets are accessed, the reduction of the background levels of spurious signal such that the real signal is unequivocal. This background we have shown is adversely affected to a dramatic degree by large probe sizes. Small probe sizes can hybridize along the target sequence allowing an iterative effect whereby these smaller probes amplify. Finally, networking of probe at high concentration is facilitated by the size of the probe. It can be seen that all of these interrelate around the common parameter of probe size. Each of these factors are dealt with in further detail.

It has been recognized in the art that smaller probe sizes were desirable to penetrate well-fixed tissue such as tissues fixed with paraformaldehyde. However, we have shown that the cell morphology is in an open configuration using paraformaldehyde allowing the penetration of longer probes (up to about 1,000 nucleotides). However, we did not appreciate two major developments in later application of this technology. First, the probe, when labelled with biotin, is unable to penetrate cellular material at equivalent fragment lengths (see Figure). Second, in order to penetrate nuclei which are more viscous, not only smaller probes are desirable but also higher concentrations are desirable. Since higher concentrations increase background, the concentration necessary for efficient hybridization to detect a single sequence copy is selected in a narrow window allowing sufficiently high concentration of probe for hybridization but not creating background.

Background is an important parameter since if there were no background at all, even the weakest scarcest signal would be detected. Hence, our efforts were directed toward reduction of background to zero and success in detecting single-copy sequences requires from manipulation of this parameter. In order to reduce the background, it was necessary to find the most important contributory factor. As described above and in the more extensive section on probes fragment length, the size of the probe is a key factor. This may be because larger probes diffuse slowly through the cell and during this time become susceptible to hybridization from the other strand. When this happens, the molecule becomes double-stranded and rigid, and therefore cannot be removed from the cell by washing. Furthermore if a molecule of probe DNA sticks to a glass surface, and is large, it acts as a target either for further hybridization (see "Network") or as a signal unto itself since it is so easily detected. Hence it is important to maintain the probe fragment size, which is virtually dispersed over a broad size range, somewhere less than the 1,000 nucleotides shown to cause background and preferably less than 700 nucleotides.

Another key to the success of the detection of signal versus noise is the iterative effect of the hybridization. When a large target is detected by smaller probe fragments which cover the entire target, each individual probe fragment may be small compared to the target. However, as they line up along the target (see Figure) they amplify their effect. Since each small probe sticks non-specifically as a random event, the noise level only consists of individual probe molecules which may stick advantageously to the cells or the glass. Since they are small, and are therefore below the threshold of detection, they do not cause background. This effect is best achieved with probe sizes which are small compared to the target nucleic acid sequence and with high concentration to achieve the high hybridization efficiency necessary to get full hybridization along the target. By selecting a threshold of detection which allows the cumulative effect of iterative signals to be visualized, but for which individual probe molecules are not visible, one effectively eliminates noise while preserving signal. The interrelationship of probe size and detection is exemplified by this iterated effect as well as by the other parameters mentioned.

Especially pertinent to detection of unique chromosomal sequences is our analysis of the role of network formation in producing hybridization signals. It had been previously suggested (Wahl et al., 1982; *Proc. Natl. Acad. Sci. USA,* 79:4381–4385; Gerhard et al., 1981, *Proc. Nat. Acad. Sci. USA,* 78:3755–3759) that hybridization with nick-translated probes could be significantly enhanced by the formation of probe "networks," produced by reannealing of many probe fragments at the site of hybridization (see Lawrence and Singer, 1985 *Nucleic Acids Research,* 13: 1777–1799). An experiment to directly test if and when network formation occurs was performed and this was coupled with a systematic analysis of the effect of probe fragment size on the formation of these networks. Generally, larger fragment sizes promote networking and that networking can amplify up to 25 fold or more the signal obtained from detection of mRNA within a cell. This signal enhancement is expected to be even more powerful with hybridization to chromosomes, since there are no membranes or cytoplasmic matrix to interfere with the penetration and networking of extremely large probe fragments.

Empirical data has shown that very large probes can cause very high levels of non-specific background signal (noise) which interferes with effective single-copy detection. While probe networks may be very important for the detection of nucleotide sequences in single-copy, the high concentrations of labelled probe preferred for use can cause this spurious background noise when employing larger size probe sizes. This concomitant increase in background was previously unappreciated. This phenomenon is factually supported by the empirical data obtained when using a commercially prepared biotinated probe for the Bam HIV fragment of the EBV viral genome probe sold by Enzo Biochemical Company. Each and every experiment using the Enzo probe yielded unacceptably high background signal (noise) levels. When the Enzo probe was analyzed, it was found to be quite large (greater than 1,000 nucleotides in length). If, however, the Enzo commerical probe was then digested with sufficient DNAse to provide labelled probe fragments only about 300 nucleotides in length, the levels of background signal (noise) were substantially and markedly reduced to very acceptable levels of signal:noise ratio. The ability to solve the major obstacle and problem of high background signal (noise) by reducing the size of the labelled probe in the hybridization fluid is both unforeseen and uncomtemplated in this art. This is especially true in view of the commonality and frequency of the high background signal problem among the various conventionally known detection systems.

This solution is particularly valuable for the single-copy detection methodology which is part of the present invention. Non-isotopic detection of single-copy nucleic acid sequences relies on the probe size as one critical element of the process. It is especially important to have a clear and complete understanding that the unforeseen result and operational window exists via the interplay of not one but two factors: the probe size and the probe concentration. When a probe size between about 100–1,000 nucleotides is employed, probe networking will serve to amplify the signal and concurrently act to avoid causing increases in background noise. However, if one uses probes less than about 100 nucleotides, probe networking diminishes and may no longer be a relevant controlling parameter. Alternatively, the use of probe sizes substantially above 1,000 nucleotides will cause massive formation of probe networks around concomitant dramatic increases in background signal—since large probes above 1,000 nucleotides in size will adhere non-specifically and indiscriminantly (as shown by the empirical data). Hence, the sample will yield high levels of background signal (noise) due to the non-specific binding. Given the unusually high concentrations of probe as the other controlling parameter, it is clear that a major enhancement effect within each type of test condition and result caused by probe size is created by the concentration factor. The optimum use conditions are thus a carefully chosen interplay of ranges between the probe size and the probe concentration.

The Non-Isotopically Labelled Probe

The probe comprises nucleic acid fragments with nonisotopic identifying label such as a fluorophore, an enzyme, or one selected from the group consisting of biotin or other moieties recognized by avidin, streptavidin, or specific antibodies. The fragment nucleotide sequence should be complementary to at least a portion of the target endogenous nucleic acids normally present within the fixed nucleus or cell; or should be complementary to at least a portion of the specific exogenous nucleic acid of interest (integrated or not) which is not normally present within the cell and is typically associated with an abnormal disorder or pathological disease state. A non-isotopic label is advantageous over an isotopic label in that it is safer to handle and easier to store and some of the commonly employed isotopic label have relatively short half lifes so for best results the labels have to be used fairly promptly upon receipt.

There are several types of non-isotopic identifying labels. Some types are as follows. One type is a label which is chemically bound to the probe and serves as the means for identification and localization directly. An example of this type would be a fluorochrome moiety which upon introduction of proper wavelengths will become excited into a high energy state and emit fluorescent light.

Fluorochromes, substances which release significant amounts of fluorescent light are generally terms "fluorophores" and are divisible into two broad classes: intrinsic fluorescent substances and extrinsic fluorescent substances. Intrinsic fluorophores comprised of naturally occurring biological molecules whose demonstrated ability to absorb exciting light and emit light of longer wavelengths is directly based on their internal structure and chemical formulation. Typical examples include proteins and polypeptides containing tryptophan, tyrosine, and phenylalamine. In addition, enzymatic cofactors such as NADH, FMN, FAD, and riboflavin are highly fluorescent. Extrinsic fluorophores, for the most part, do not occur in nature and have been developed for use as dyes to label proteins, immunoglobulins, lipids, and nucleic acids. This broad group includes fluorescein, rhodamine, and their isocyanates and isothiocyanates derivatives; dansyl chloride; naphthalamine sulfonic acids such as 1-anilino-8-naphthaline sulfonic acid and 2-p-toluidinylnaphthalene-6-sulfonic acid and their derivatives; acridine orange; proflavin; ethidium bromide; quinacrine chloride; and the like. All of these are deemed suitable for use within the present invention. Fluorochromes are the preferred label of this invention. They provide the highest resolution possible with a light microscope (i.e., 0.1 u). Fluorochroming labels lead to high sensitivity since resolution is so high. The use of a fluorochrome label allows one to resolve labelling on single chromatids which serves as an affirmation that hybridization occurred unequivocably, and further allows detection precisely at site of hybridization rather than at some distance away.

A second type utilizes a chemical reagent which yields an identifiable change when combined with the proper reactants. An example of the second type would be the use of an enzyme such as alkaline phosphatase, chemically bound probe; wherein an appropriate enzyme substrate and the necessary cofactors are added to the hybridized sample which enables the enzyme to react and provide a detectable color change. The chromophoric product identifies the presence and position of the TNA sequence.

Alkaline phosphatase is an example of an enzyme which has been used conventionally in histochemistry for the labelling of tissues by deposition of a dark purple color in the region where it has been localized. A variety of different colored reaction products are commonly available using different enzyme substrates. The preferred reaction substrate of alkaline phosphatase labelled probes in this methodology is nitroblue tetrazolium combined with bromochloro indolyl phosphate.

Other enzymes may also be usefully employed as non-isotopic labels. These desirably include horseradish peroxidase and galactosidase. Each of these enzymes has its own unique chromogenic system of specific substrates, co-factors, and resulting chromophoric reaction products.

The enzyme of choice can be joined directly to the nucleotides of the probe via use of a linker arm which is typically bonded to an amino acid side group on the enzyme structure in order that the enzyme retain its activity. Analogous procedures may be used to join an enzyme to avidin or streptavidin molecules. These include: biotinating the enzyme to form a complexed molecule; or polymerizing the enzyme and conjugating the polymeric form to avidin; or conjugating the enzyme to streptavidin directly at molar ratios from 1:1–2:1. Among these alternative procedures, the last has been found most useful and convenient.

A third type of labelling is an indirect linkage mechanism of specifically binding entities—such as the biotin-avidin system. The probe is preferably joined to biotin in the conventionally known manner. After introduction of the probe into the sample under conditions which allow in-situ hybridization to occur, an avidin (or streptavidin) conjugated fluorochrome or enzyme is added. The specific binding affinity between the biotin and the avidin (or streptavidin) conjugate provides the specificity for attaching the fluorochrome or enzyme to the probe. Biotin labelled probes are preferably prepared by nick-translating actin probes and control probes using the Rigby et al. methodology and a biotinyl-dUTP reactant containing an 11-atom spacer arm between the 5 position of the pyrimidine ring and the carboxyl group of the biotin moiety (commercially available from ENZO Biochemical Company). Similarly, a specific antibody raised the biotin moiety can be successfully substituted for avidin or streptavidin in the conjugate.

It will be recognized also that other identifying labels may also be used with the described probes. These include fluorescent compositions such as energy transfer groups, conjugated proteins, or antibodies and antigens. All of these are deemed useful and within the scope of the present invention.

The penetratability of non-isotopically labelled probes into fixed chromosomes, fixed cellular nuclei, and whole cells (and tissues) and the efficiency of the in-situ hybridization is directly influenced by the size of the labelled probe fragments.

The concentration of total labelled probe that can be employed is that amount which will exceed the estimated quantity of available DNA or RNA to be detected and drive the hybridization reaction efficiently and to promote a high rate of probe nucleic acid annealing. The conventional range of probe concentration of less than about 0.2 ug/ml (representing 2.0 ng/10 ul of reaction fluid) is generally inadequate to initiate efficient in situ hybridization to low copy or single-copy sequences. Moreover, the conventional view that it is most desirable to employ the most minimal concentrations of probe is inaccurate and completely opposite to the requirements of the present invention when non-isotopically labelled probes are employed. The probe concentration usually ranges between 1.0–10.0 ug/ml routinely with the preferred concentration being about 2.5 ug/ml. The preferred concentration for single stranded RNA probes is less than DNA probes. For oligonucleotides, the preferred concentration would be between 0.1 and 0.5 ug/ml.

Non-Specific Competitor

The nature and source of the non-specific nucleic acid competitors for the probe in the hybridization fluid is another unique modification and change from conventional practices. Traditionally, investigators have employed sonicated salmon sperm DNA and *E. coli* tRNA for this purpose regardless of the type or source of the nucleic acid sequences to be hybridized. The present invention, however, prefers that the kinds and sources of non-specific competitor nucleic acids employed be of similar or analogous nucleic acid sequence as the probe to be detected within the sample. The degree of similarity will vary considerably with the source of the probe nucleotides and the nature of the nucleic acid of interest. For example, as empirically demonstrated hereinafter, it is possible to accurately detect a single-copy of Epstein-Barr virus integrated into the DNA of the Namalwa lymphoma cell line when a hybridization fluid was prepared containing from 2–50 nanograms (hereinafter "ng") of labelled probe combined with 5 ug of sonicated salmon sperm DNA and 20 ug *E. coli* tRNA in 5 ul deionized formamide. Both of these are commonly used as non-specific competitors. It will be recalled also that the theoretical basis for conventionally including non-specific competitors to the probe in a hybridization fluid is to reduce the amount of non-specific binding for the probe nucleic acid sequences by supplying the competitor nucleic acid sequences as a diluent. By diluting the original number of non-specific binding sites in the sample, the number of potential sites for non-specific sticking with the probes are markedly reduced. Conventional practices established in this art for preparing hybridization fluids have not discriminated among the various potential sources of DNA and RNA to be employed for use as non-specific nucleic acid competitors. For purposes of the detecting integrated Epstein-Barr virus, the *E. coli* tRNA is sufficiently similar in type and nature to the probe employed for detection such that an effective reduction of non-specific binding is achieved. Although the viral DNA to be detected by the labelled probe and the *E. coli* tRNA are meaningfully different, there is sufficient chemical similarity between them to achieve the dilution effect. There is, however, no competition for hybridization to the nucleic acids of interest in the sample between the probe and the non-specific competitor.

The situation is quite different when the nucleic acids of interest to be detected are eukaryotic genomic DNA or nuclear RNA, which typically contain small interspersed repetitive DNA sequences such as those found in the human gene pool. Typically, non-isotopically labelled probes are used for detection which contain nucleic acid sequences similar to those in the target. Both the target and the probe thus contain a variety of smaller repetitive nucleic acid sequences which are interspersed within the larger nucleic acid sequence of interest to be hybridized in situ and within the bulk of chromosomal or nuclear DNA which is not of interest. These repetitive sequences present throughout the human DNA typically will hybridize with the repetitive sequences present in the probe and thus obscure hybridization to the target DNA of interest. The use of conventional non-specific competitor nucleic acids (salmon sperm DNA and *E. coli* tRNA) fails to reduce non-specific hybridization to repetitive elements because the salmon sperm or *E. coli* nucleic acids are not sufficiently homologous to the human repetitive DNA to reduce hybridization to the repetitive sequences in the target cell.

The present invention solves this problem by the use of non-specific competitor nucleic acids which are derived from eukaryotic cells similar to those from which the probe nucleotides are obtained. The non-specific competitor nucleic acids will thereby contain repetitive sequences similar if not identical to those repetitive sequences in the probe and to those repetitive sequences surrounding the targeted nucleic acids of interest in the prepared sample. Non-specific competitor nucleic acids having these repetitive sequences do not function solely as diluents as in conventional practice; to the contrary, the non-specific competitor nucleotides engage in active hybridization with the repetitive sequences surrounding the target in the presence of and in actual competition with the labelled probe. In this manner, the repetitious sequences within the eukaryotic derived non-specific competitor nucleotides effectively reduce non-specific hybridization and substantially increase the specificity in-situ hybridization between the target and the labelled probe.

The most dramatic increases in in situ hybridization efficiency and sensitivity of detection have been observed in human gene mapping studies, some of which are empirically described hereinafter. It is most desirable that when probes are prepared for detecting human or human derived targets, that the non-specific competitor also be of human origin. In this way, the human non-specific competitor nucleotides function both as a diluent and as a specific suppressor of the repetitive sequences in the target. Similarly, for probes intended to detect eukaryotic nucleic acid targets generally, it is preferred that the non-specific competitor nucleic acids also be of eukaryotic origin. All that is required is that there be sufficient homology within identifiable portions or segments of the probe and the non-specific competitor such that an effective competition between the repetitious nucleic acid sequences surrounding the target and the competitor nucleotides occurs within the prepared sample.

With probes destined for use against human targets, the non-specific competitor nucleic acids can take a variety of forms. These include placental total genomic DNA, cloned Alu, kpn, or the repetitive sequences in any clone coding for human derived sequences.

Soluble Salts

The prepared hybridization fluid can also contain at least one soluble salt present at a concentration preferably not substantially less than 0.3 M. The preferred salt solution is sodium citrate buffer prepared in 4 fold concentration strength (hereinafter "4×SSC buffer") which is preferably composed of 0.6 M sodium chloride, 0.06 M sodium citrate, and 0.05% Triton X-100™ (polyethylene glycol ethyl aryl ether). Contrary to some practices for preparing hybridization fluids which employ only physiological saline (sodium chloride in water at a concentration between 0.85–1.0%), empirical evidence demonstrates that such a low concentration of soluble salt is insufficient for purposes of reducing non-specific binding of the avidin or streptavidin used to detect non-isotopic labelled probes. This is especially important if the non-isotopic label is biotin, recognizing that the subsequent reagent for detection purposes will therefore include avidin or streptavidin conjugated molecule. It is preferred that when biotinated probes are employed followed by avidin or streptavidin conjugated reagents, the salt concentration of the hybridization fluid should be at least 0.3 M when the hybridization fluid is employed. The maximum useful concentration of soluble salt may be increased to as much as 0.6 M if desired.

The Ionizing Solvent

Another component of the hybridization fluid is the use of an ionizing solvent such as formamide. This polar solvent is the standard fluid used for preparing hybridization fluids generally known in the art. Although it is expected that other polar ionizing solvents other than formamide could be employed in varying degrees of success, it is recommended that this solvent continued to be used predominantly, if not exclusively, for preparing hybridization fluids. However, because empirical data has demonstrated variation in signal:noise ratios up to 20 fold difference among the different commercially available sources of formamide, it is recommended that only a single batch of formamide be used uniformly for an entire series of in-situ hybridizations and that sufficient quantities of formamide be uniformly prepared as single lots without intermingling or exchange with other lots or sources.

A preferred hybridization fluid will therefore be prepared in the following manner. Not substantially less than 0.2 ug/ml of non-isotopically labelled probe is combined with between 5–50 ug of non-specific nucleic acid competitors for the labelled probe, the competitor nucleic acids being of a similar type and origin as the nucleic acids of the probe. This initial mixture of nucleic acids is then suspended in approximately 5.0 ul of an ionizing solvent such as 100% formamide and heated to 70–80C. for approximately 10 minutes. After heating, the nucleic acids suspended in the formamide solvent are combined with an equal volume of hybridization buffer; and preferably with a fluid mixture composed of 4×SSC (0.3 M sodium citrate) buffer, 2.0% bovine serum albumin, 20 mM vanadyl sulfate, and 20% dextran sulfate. All of these compositions are commercially available. The final concentration of the completely prepared hybridization fluid thus will comprise not less than 0.2 ug/ml labelled probe; non-specific competitor nucleotides able to compete with the probe for non-specific sticking; 50% formamide; and 2×SSC buffer (0.3 M sodium citrate) containing 1% bovine serum albumin, 10 mM vanadyl sulfate, and 10% dextran sulfate.

Conditions for In situ Hybridization

One of the major advantages of the novel in-situ hybridization method is that relatively small numbers of cells comprise a sample; and that large number of identical samples may be tested over a very short period of time. From each isolation of prepared nuclei or morphologically intact cells, large numbers of coverslips ranging from 60–100 in number with each coverslip containing up to $10^6$ nuclei or cells of uniform density are utilized so that the individual test samples within and between different experiments could be directly compared and statistically evaluated. Preferably, just prior to the hybridization step, each coverslip containing the prepared nuclei or cells is cut in half using a diamond pencil to yield two identical test samples. One half of each coverslip is then hybridized using a hybridization fluid comprising labelled probe while the other half coverslip is hybridized using a fluid comprising another non-isotopically labelled probe serving as a control (or whose nucleic acid sequences are markedly different). Alternatively, adjacent sections of tissue can be used.

For detecting DNA sequences as the nucleic acid of interest, the prepared samples on the half coverslip are first incubated for approximately 10 minutes in a mixture comprising 0.1 M triethanolamine and 0.125% acetic anhydride. The use of acetic anhydride in this manner is preferable in order to assist in reducing the background noise for non-isotopic detection, contributing to the signal:noise ratio which approaches infinity. Acetylation of proteins changes their charge to acidic, thereby reducing their binding of nucleic acids.

Subsequently for DNA hybridization, the prepared samples are then denatured by incubation at 70° C. for 2 minutes in a fluid mixture of 70% formamide and 2×SSC buffer. All preparations were then immediately dehydrated through cold 70%, 95%, and 100% ethanol for 5 minutes each and then air dried. Each half coverslip is then combined with the appropriately prepared hybridization fluid.

Each half coverslip represents one test sample which is preferably placed cell side down onto a drop containing 10.0 ul of the appropriate hybridization fluid supported by a parafilm sheet. Care should be taken that the hybridization fluid is applied immediately after its preparation while it is still relatively warm to each sample under test. Each sample is then covered loosely with another sheet of parafilm and incubated at 37 C. in a 100% humidified chamber for a period of time ranging from not less than 10 minutes and not more than 24 hours in duration.

It will be appreciated that prior in-situ hybridization techniques require a hybridization time ranging from not less than one day (sixteen hours) and as much as four days in duration. In contrast, the present invention provides results that are detectable in about 10 minutes hybridization time; offers quantitative data which is reproducable at 30 minutes duration and is complete within the first 3–4 hours. It should be noted, however, that hybridization should not exceed approximately 24 hours in the hybridization fluid. It is preferred that the incubation period be not longer than approximately three or four hours in duration; but if this is not feasible or desirable to the user, the time may be extended up to 24 hours or conversely decreased to 10 minutes without detrimental loss of either hybridization efficiency or accuracy.

Avoidance of RNAse Treatment Prior to In-Situ Hybridization for DNA Detections

A unique and distinguishing feature of the present method for the detection of specific DNA sequences of interest either in the nucleus or the cytoplasm of a cell, is the requirement of avoiding the use of RNAse with the test sample at least until after DNA denaturization and in-situ hybridization has occurred; and preferably avoiding the use of RNAse completely regardless of source or concentration under all test conditions of DNA detection. Conventional practices and procedures long used in this art have consistently employed a RNAse (such as RNAse A) to degrade and eliminate RNA in the cell prior to denaturization of the DNA in the sample—in the belief that this would substantially reduce non-specific binding and hybridization to transcribed sequences. The conventional wisdom holds that by destroying the RNA in the cytoplasm and nucleus of the cell prior to DNA denaturization, there would be no effective competitor for the subsequently introduced probe. However, in so far as is presently known, no consideration whatsoever has yet been given in the scientific literature to the potential effects of RNAse on disruption of the cellular morphology of the sample under test. Instead, conventional practice has assumed that nuclear morphology and the resolution of DNA sequences remains uneffected by the use of RNAse.

Experimental evaluation of this conventional theory has shown it to be false and without factual basis or support. Rather than increase hybridization efficiency, the effect of introducing RNAse A prior to denaturization only increases the actual loss of DNA from the sample and substantially alters the permeability of the prepared sample (cellular or nuclear) to subsequent penetration by a labelled probe. This was shown with highly pure RNAse preparations which had been heated prior to use to eliminate the possibility of any minor contamination by the more labile DNAse. Because nuclear RNA contributes to retention of morphology and DNA during denaturation and hybridization, if an RNAse must be employed in the protocol at all, it should be RNAse H which digests the RNA within DNA/RNA hybrids only; and this RNAse H should only be combined with the prepared sample only after the DNA has been fixed, denatured, and hybridized in-situ with a labelled probe rather than prior to fixation and/or denaturization of the test sample. However, for maximal sensitivity, it is desirable that RNAse be eliminated from the methodology.

Most protocols use RNAse as a treatment before in-situ hybridization is performed. This RNAse (mostly RNAse A but sometimes RNAse T1) is to destroy RNA within the sample which might interfere with hybridization to DNA, or decrease resolution by providing competing targets. However, this is not only unnecessary, but has a distinct deleterious effect on cellular (particularly nuclear) morphology, such that distortions and diminutions occur to the signal. For most cellular sequences, examined, the presence of cellular RNA does not interfer with gene detection. Only in cases where abundant nuclear RNA is present is RNAse needed and it it is to be avoided for maximal sensitivity. This was generally unappreciated in the prior art. In order to remove the RNAse signal which impedes analysis of the DNA signal, specifically in interphase chromatin, RNAse H is used after in-situ hybridization which digests only RNA which is hybridized to DNA. This allows only the RNA to be removed which has hybridized the probe, and therefore removes probe by removing its target specifically. Therefore, the disruption of morphology does not occur, and a high resolution of DNA sequences is possible, even if transcription is occuring at high rates from these sequences. This is a significant improvement and is preferred for successful interphase gene mapping of transcribed sequences.

Avoiding the use of RNAse provides unexpected and substantial benefits to the investigator since the retention of the DNA is enhanced. The elimination of RNAse allows for the detection of both DNA and RNA nucleic acid sequences concurrently within the same sample using either two different and individually labelled probes for individual hybridization of each nucleic acid; or the use of individually labelled probes for different DNA regions not transcribed into RNA. Such double-labelling probe methods are not generally feasible following the conventional practice known in the art.

Interphase Chromatin Mapping

The in situ hybridization method described herein has allowed the discovery of a novel and unexpected method for assessing the physical linkage of two or more sequences directly within chromatin of decondensed interphase nuclei. The decondensation of interphase chromatin coupled with the exceptionally high resolution of this technique makes the distance between sequences separated by only 28 kb or more of DNA resolvable at interphase. To determine the proximity of two cloned DNA sequences, the two sequences are both labelled with biotin and hybridized simultanously to interphase nuclei. Closely-spaced nucleic acid sequences (less than 3–4 megabases apart) will appear as paired genomic signals (see FIG. 18). Measurement of the average distance between these sequences at interphase will provide an estimate of the physical distance in kilobases of DNA (see Examples 1 and 6).

This type of gene mapping within interphase chromatin was not possible with prior in situ hybridization techniques since it requires exceptionally high resolution to actually observe the two distinct spots or signals representative of the closely spaced sequences. Without a high resolution technique the two spots or signals would appear blurred or as a single spot when the two target sequences are closely spaced (i.e., less than 3–4 megabases apart).

Post Hybridization Rinses

After completion of the hybridization, each sample (half coverslip) is preferably placed in a 10 ml volume Coplin staining jar (commercially available from VWR) or a petri dish and rinsed three times using three different rinses for preferably 30 minutes duration each. The rinsing solutions to be used serratim are: a first rinse comprising 2×SSC buffer (0.3 M sodium chloride and 0.03 M sodium citrate) and 50% formamide at 37° C.; and a third rinse comprising 1×SSC buffer at room temperature on a shaker. More harsh rinse solutions and more extensive rinsing periods were found to be unnecessary; and less extensive rinsing (5 minutes per rinse) was adequate. After this three rinse cycle, each sample is ready immediately for quantitiate or qualitative detection of the in-situ hybridization.

In addition, the rinsing times may be decreased to 5 minutes duration each with little loss of effectiveness. It will be recognized that such short rinsing periods are contrary to generally accepted practices; most previously known techniques require extensive rinse procedures lasting as long as several days in duration and using as much as several liters of rinse solution per sample. Insofar as is presently known, the novel methodology is the first to recognize the value of and to utilize rapid and minimal rinsing of samples based upon optimal rinse conditions.

The unique in-situ hybridization methodology described above and the experimental data provided hereinafter demonstrate the major advantages which overcome the defects and deficiencies of previously known hybridization techniques. In short, the defects of long and tedious assays, non-reproducible and non-quantitative results, and poor sensitivity have been eliminated. It should be especially noted that not only have the simplicity and speed of the hybridization been increased, but also the efficiency of the hybridization has been increased up to ten fold over prior art practices with concomittant increases in sensitivity such that a single-copy of a specific nucleic acid sequence of 2 kb or less can be quickly detected within a single cell.

Non-Isotopic Detection

The means for detecting and localizing the non-isotopically labelled probe after in-situ hybridization will vary with the nature and identity of the non-isotopic label employed for this purpose. For example, if a fluorophore is directly linked to the nucleic acid sequences of the probe, then the means for detection are only that the proper light wavelength be introduced into the sample and that the fluorescent light emissions emanating from the sample be observed. This is done directly and conveniently using a fluorescent light microscope which allows the results to be visualized directly by the investigator and to be quantitiatively assessed in a minimum of time. Similarly, should the label by an enzyme such as alkaline phosphatase, directly linked to the nucleic acid sequences comprising the probe, then the means for detection will include a useful enzyme substrate in proper concentration such as nitro-blue tetrazolium to be added to the sample and then measuring the degree of colored reaction product formed in the conventionally known manner. The direct visualization of the colored reaction product by the investigator also identifies the location of the probe within the sample and will provide a quantitative correlation for assessing the concentration of the specific nucleic acid of interest within that sample. All such methods are thus conventionally known and instrumentation is commercially available to aid the investigator in compiling quantitative data in a rapid and efficient manner.

While the signal for detecting 1–2 kb is sufficient for visualization via a conventional fluorescence microscope, the use of image enhancement techniques for detection purposes has become common. The use of a charge coupled device (originally used by astronomers to detect faint stars) has now found application for the detection of very weak biological fluorescent signals and has been used successfully with the parent methodology. Similarly, the use of a silicon intensification tube (although less sensitive than the charge coupled device) also would increase the sensitivity of detection about 10 fold.

Alternatively, if the probe nucleic acid sequences do not directly bear the fluorophore or enzyme directly, the alternative specific binding systems using biotin and avidin (or streptavidin) should be employed.

Non-Isotopic Detection Using Biotin Labelled Probes

Reagents are commercially available for the enzymatic detection of biotin labelled probes extracellularly on filters using reagents comprising avidin or streptavidin, an enzyme such as alkaline phosphatase which has been biotinylated and a chromogenic enzymatic substrate [Vectastain ABC kits, DNA detection kits from BRL Laboratories, ENZO Biochemical Company] or a conjugate of streptavidin and alkaline phosphatase ("DAKO"). However, attempts to employ these reagents in accordance with the prescribed protocols for detection of labelled probes with in situ hybridized cells (or tissues) were unsuccessful due to the consistent occurrence of false positives and spurious background. Samples which had been hybridized with a control DNA probe exhibited approximately the same extent of enzymatic reaction product as did samples which were hybridized in-situ with the experimental biotinated probe, a result found to be caused by non-specific adherence of the reagents to the cytoplasm of the cell under the test conditions employed. In particular, experiments using $^{125}$I-avidin demonstrated that this reagent was especially adherent to cell cytoplasm when applied in the solution(s) prescribed by the commercial kits (0.1 M Tris-HCl, pH 7.5; 0.1 m NaCl; 2 mM MgCl$_2$; 0.05% Triton X-100™. It was also discovered that when the biotin is incorporated into the probe, the fragment size after labelling which can be tolerated without great increases in background is more narrow that with isotopically labelled probes. Hence, probe molecules containing biotin greater than approximately 300 nucleotides stick greatly to cell cytoplasm. It is possible, however, to decrease the non-specific binding of larger sized (greater than 200 nucleotides) biotinated probes by 80–90% via a post fixation treatment of the sample using 0.25% acetic anhydride and/or a combination of 0.5% Triton X-100™ and 1.0 mM biotin in PBS. Most important, however, is the use of high salt (greater than 0.3 M NaCl and preferably 0.6 M NaCl) to reduce non-specific binding.

The novel detection method using probes permits th user to reproducibly detect biotinated probes hybridized in-situ. The improvement comprises using an aqueous salt solution of at least 0.4 M concentration as a fluid carrier for the avidin or streptavidin. Empirical tecting demonstrates that if avidin or streptavidin is applied in the preferred aqueous 4×SSC buffer (0.6 M sodium chloride, 0.06 M sodium citrate, 0.05% Triton X-100™), non-specific binding of this component to the cells is eliminated. The protocols given below are thus directly suitable for detection of biotinated probes within cells and tissues hybidized in-situ.

For detection means employing an enzyme such as alkaline phosphatase, the preferred protocol for non-isotopic detection is as follows:

1. Preheat Buffer A to 42° C. for a predetermined time. Buffer A comprises 3% w/v bovine serum albumin (BSA) in 0.1 M Tris-HCl, pH 7.5; 0.1 M NaCl; 2 mM MgCl$_2$; and 0.05% Triton X-100™.
2. Incubate each sample in an excess of preheated Buffer A for 20 minutes at 42° C.
3. Remove Buffer A by blotting each sample on filter paper.
4. Prepare a 2 ug/ml solution of streptavidin or avidin (or alternatively, a streptavidin-alkaline phosphatase conjugate) using 1.0 ml of 4×SSC buffer and allow this mixture to stand at room temperature for approximately 10 minutes.
5. Wash each sample once in 2 ml of 4×SSC buffer containing 3% BSA and then twice in 4×SSC buffer without BSA.
6. Incubate each washed sample individually with 1 ug/ml monoalkaline phosphatase or polyalkaline phosphastase prepared in Buffer B for 10 minutes are room temperature. Buffer B comprises 0.1 M Tris-HCl, pH 7.5; 0.1 M NaCl; 2.0 mM MgCl$_2$; and 0.05% Triton X-100™.
7. Wash each sample twice for five minutes with Buffer B at room temperature. [Please note that steps 6 and 7 are omitted if the streptavidin-alkaline phosphatase conjugate is used.]
8. Quickly rinse each sample with excess Buffer C. Buffer C comprises 0.1 M Tris-HCl, pH 9.5; 0.1 M NaCl; and 50 mM MgCl$_2$.
9. Combine 33 ul of nitro-blue tetrazolium (75 mg/ml in 70% dimethylformamide) with 7.5 ml of Buffer C taking care to keep this mixture protected from light; then vortex the mixture and add 25 ul of bromo-chrlorindoyl phosphate (50 mg/ml in dimethylformamide); vortex and place this prepared solution on each cell sample.
10. Incubate each sample in the dark with gentle shaking at room temperature for a period ranging from 5 minutes to 24 hours.

For detection means employing a fluorophore such as fluorescein conjugated to avidin (or streptavidin), the preferred protocol is as follows:

1. The samples are incubated in 2 ug/ml avidin (or streptavidin) conjugated to the appropriate fluorochrome in 4×SSC buffer and 1% BSA for 30 minutes at room temperature.
2. All samples are then rinsed at room temperature for 10 minutes each using 4×SSC buffer, followed by 4×SSC buffer containing 0.15% Triton X-100™, and then 4×SSC buffer alone.
3. Samples were then counterstained with the appropriate fluorophore such as the DNA fluorophore DAPI (diaminophenylindole) for 5 minutes. The fluorophore is preferably present in phosphate buffered saline in an appropriate concentration.
4. The samples are then mounted in antibleach mounting medium and directly visualized at 1,000×magnification using a microscope equipped with epifluorescence optics for fluorescein or other fluorophores. No image intensification or image processing devices are necessary. The procedure, however, is compatible with such an approach. In addition, photographic images can be taken using commercially available film and speeds.

The In-Situ Hybridization and Non-Isotopic Detection Methods in Combination

It is intended and expected that the novel in-situ hybridization method be utilized with one or more of the non-isotopic detection methods described wherein. Although each may be used separately to advantage, it is when these methodologies are performed in unison that the more desired technical advances provided by the present invention become apparent. These advances are: simplicity, speed, and a sensitivity able to detect even a single-copy of a specific nucleic acid sequence 2 kb in size.

Simplicity is provided by eliminating the number of steps and reducing the complexity of the steps conventionally required to perform the in-situ hybridization and detection; speed is provided by the use of only a few reagents for shorter times and by using commonplace instrumentation which does not require either a skilled technician or extensive handling; sensitivity is provided by the ability to detect most of the targeted RNA or DNA sequences in the sample rather than only a minor fraction of targeted nucleic acids of interest in the nucleus, or a minor fraction of nuclei in the sample; and/or cytoplasm of the cell. The best evidence of both these advances is demonstrated by the Minimal Time Fluoroscence Protocol which follows.

Summary of Minimal Time Fluorescence Protocol

The following is an outline of the technical steps in the novel method indicating a minimal time for each step, beginning with previously prepared solutions and reagents.

| MINIMAL TIME | MANIPULATION |
|---|---|
| 5 min. | 1. Fixation of prepared swollen nuclei or wholly intact appropriate fixative for 5–15 minutes. |
| 5 min. | 2. Rehydration of sample in 0.2 M Tris, .01 M glycine for 5 ininutes. |
| 5 min. | 3. Incubation in 50% formamide, 2 × SSC buffer for 5 ininutes.<br>4. While the samples are incubating, heat 5 ul of Solution A per sample to 70–80° C. for 10 minutes. Solution A contains 20 ng labelled probe DNA, 15 ug sonicated non-specific (or specific) competitor DNA, 60 ug non-specific competitor tRNA in 5 ul formamide. Then add 5 ul of Solution B. Solution B contains 4 × SSC buffer, 2% BSA, 20 mM vanadyl sulfate, 20% dextran sulfate. |
| 10 min. | 5. Hybridization at 37° C. for at least 10 minutes but preferably not more than 24 hours. Concentration can be adjusted for preset times. |
| 15 min. | 6. Rinse vigorously three tiines for 5 minutes each in 10 ml volumes of Solutions C, D, and E in succession:<br>Solution C contains: 2 × SSC buffer, 50% formamide at 37° C.;<br>Solution D contains: 1 × SSC buffer, 50% formamide at 37° C.;<br>Solution E contains: 1 × SSC buffer on a shaker at room temperature. |
| 15 min. | 7. Detection of hybridization. Biotinated probes: exposure to fluorophores conjugated to avidin (or streptavidin) in 4 × SSC buffer. |
| 5 min. | 8. Wash avidin-fluorophore.<br>9. Visualize the signal. |
| Total Minimum Time = 60 minutes | |

It will be appreciated by persons working routinely in testing laboratories and in research centers that the Minimal Time Fluorescence Protocol may be utilized for tens or hundreds of samples at one time using one or more labelled probes (each having a different nucleotide sequence) and that the entirety of the protocol utilizing multiple samples and multiple probes may be repeated cyclically many times in the course of 8 hours time. Equipment has been designed to automate these steps and reduce labor (Fischer Scientific Company). In this manner, many hundreds of test samples may be received, tested, and evaluated by relatively unskilled persons within the confines of a single work day.

It will be recognized that the most preferred methodology employs fluorophores and fluorescence detection means. Fluorescence detection is most preferred because this technique provides the greatest resolution possible at the light microscope level, far superior to autoradiography and to enzymatic non-isotopic detection techniques. Fluorescence detection has conventially been thought to lack sufficient sensitivity for the detection of relatively small (4–5 km) single-copy sequences of nucleic acids. However, investigations using the biotin-avidin systems indicate that the failure to previously detect single-copy nucleic acid sequences was not due primarily to an insensitivity of the detection system, but rather to poorly characterized hybridization and detection conditions which resulted in very low signal:noise ratios. The modifications and improvement of in-situ reagents and hybridization conditions in accordance with those presented herein have provided a signal:noise ratio which approaches infinity. The present invention also provides a 10–20 fold greater resolution than that previously possible using autoradiography and thus obviates the need for large numbers of samples for statistical analyses.

Previously unappreciated in this art was the interplay between resolution and sensitivity which is a major aspect of the present invention. Autoradiography operates and provides via a decay of radioactive label. The released emissions strike a photographic detector plate at a distance from the site of hybridization. Inherently, this mechanism causes the spread of the signal over a broad surface area and the signal becomes diffused. In comparison, non-isotopic hybridization is detected at the site of hybridization. The non-isotopic signal is confined to a small area which is essentially a point source. This makes the signal (e.g., fluorescence) detectable in a manner no other method can imitate or approach. Hence as resolution increases, there is a concomittant increase in sensitivity of detection. This increase in sensitivity, however, is deemed to be an unforeseen result and product of the unique ability to increase resolution.

EXAMPLE 1

Preparation of Nuclei and Metaphase Figures

The Namalwa cell line was maintained in suspension in RPMI medium, 10% fetal calf serum and 0.1% gentamycin. The L8 rat myoblast line was used as a control. Growing cultures were incubated at 37 C. with 0.015 ug/ml of colcemid (demicolcine) for 2–4 hours. Cells were then harvested and incubated in 0.075 M KCl at 37 C. for 17 minutes followed by fixation in three changes of fresh 3:1 methanol:acetic acid according to conventional cytogenetic techniques. Cells in suspension were dropped onto clear glass coverslips in a humid environment to promote spreading of chromosomes. Coverslips were then air dried overnight and stored at –80 C. with dessicant until further use. Prior to hybridization, chromosome preparations were baked at 60 C. for 3 hours to promote further drying and "hardening" of the nuclear material.

Probes and Nick-Translation

The restriction map of the Epstein-Barr genome is represented in FIG. 5 and clones of specific fragments in a pBR322 vector were obtained. Probes used were the W, A, Y/H, and K fragments representing approximately 30, 12, 7, and 5 kb, respectively (Skare, J. et al., *Proc. Natl. Acad. Sci. USA*, 77, 3860–3864 (1980)). Plasmid DNA was nick translated using biotinated –11-dUTP (Enzo Biochemical) using conventional techniques. Fragment size was controlled by varying the amount of DNAase in the reaction as determined empirically for each lot of DNAase. Size of probe was determined using alkaline agarose electrophoresis followed by transfer to nitrocellulose filter and visualization using streptavidin and biotinylated alkaline phosphatase. Probe preparations were used if the range of probe fragment sizes after nick translation was between 300 and 1000 nucleotides. Results of quantitative studies using total human genomic DNA as a probe demonstrated that larger biotinated probe fragments worked better for hybridization to chromosomes or nuclei than for hybridization to whole cells (Lawrence, J. B. et al., *Nucl. Acids Res.* 13, 1777–1799, (1985); Singer et al., *Biotechniques*, 4, 230–250 (1986).

Hybridization and Detection

Cytogenetic preparations were incubated for 10 minutes in 0.1 M triethanolamine and 0.25% acetic anhydride and were then denatured by incubation at 70° C. for 2 minutes in 70% formamide, 2×SSC. Preparations were immediately dehydrated through cold 70%, 95%, and 100% ethanol for 5 minutes each and then air dried. The hybridization solution was similar to that previously described for detection of mRNA (Lawrence et al.,(1985) cited supra) except that higher probe concentrations and larger probe fragment sizes were used. For each sample 2–50 ng of probe, 5 ug of sonicated salmon sperm DNA, and 20 ug *E. coli* tRNA were suspended in 5 ul deionized formamide and heated from 70° C.–80° C. for 10 minutes. An equal volume of hybridization buffer was then added, so that the final hybridization solution consisted of 2×SSC (0.3 M sodium citrate buffer), 1% BSA and 10% dextran sulfate. Immediately after mixing, the hybridization solution was placed on the samples, covered with parafilm and incubated at 37° C. in a humidified chamber overnight. Samples were rinsed for 30 minutes each in 50% formamide-2×SSC at 37° C., 2×SSC and finally 1×SSC at room temperature. To eliminate the possibility of contaminating cytoplasmic or nuclear RNA, slides were either treated prior to hybridization with 100 ug/ml RNAase A for 1 hour at 37° C. or, preferably treated after hybridization with RNAase H. RNAase H was used at 8 U/ml for 1 hour at 37° C. in a buffer consisting of 100 mM KCl, 20 mM Tris-HCl, (pH 7.5), 1.5 mM $MgCl_2$, 50 ug/ml BSA, 1 mM DTT, 0.7 mM EDTA, and 13 mM HEPES (Minshull et al., *Nuc. Acids Res.*, 14, 6433–6451, (1986).

Hybridization was detected using avidin conjugated to fluorescein. Samples were incubated in 2.0ug/ml avidin in 4×SSC, 1% BSA for 30 minutes at room temperature. Previous quantitative studies using 125I-avidin (Singer et al., (1987) *In situ Hybridization: Application to the Central Nervous System,* Valentino et al. (Eds.) Oxford Univ. Press, NY) showed that non-specific sticking of avidin was 10-fold less in 4×SSC than in PBS. Samples were then rinsed at room temperature for 10 minutes each in 4×SSC, 4×SSC with 0.1% Triton X-100™, and then 4×SSC. Samples were stained with the DNA fluorochrome, DAPI (diamino phenylindole) for 5 minutes at 0.1 ug/ml in PBS and mounted in antibleach mounting medium (Johnston et al., *J. Immunol. Meth.*, 43, 349–350 (1981)).

Microscopy

Samples were directly visualized at 100× magnification on a Zeiss ICM microscope equipped with a epifluorescence optics for DAPI (Exciter 365 nm, Reflector 390 nm, Barrier 420 nm) and for fluorescein (Exciter 485 nm, Reflector 510 nm, Barrier 515–560 nm). No image intensification or image processing devices were utilized. Black-and-white pictures were taken with Tris-X (ASA 400 film). Exposure times were generally 2.5 minutes for fluorescein and a few seconds for DAPI fluorescein. Samples were evaluated within a few weeks after detection since the fluorescent signals faded significantly over time.

Results: Sensitive Detection of EBV Sequences on Chromosomes and in Nuclei: Evidence for Two Integrated Genomes In initial experiments, samples were hybridized with the BamHI W fragment of EBV, a sequence approximately 3 kb long which is reiterated 6–10 times in the EBV genome (FIG. 5). After hybridization, the biotinated W probe was detected using fluorescein-conjugated avidin while in the same sample chromosomes and nuclei were visualized with the DNA fluorochrome, DAPI. Hybridization to Namalwa cells resulted in bright fluorescein spots in each metaphase figure and nucleus. It was immediately apparent by the labelling in identical positions of each sister chromatid on the short arm of chromosome 1 that the spots over metaphase figures represented bona fide signal (FIGS. 6A and 6B), which is consistent with the previous localization of the EBV genome to lp35 (Henderson et al., 1983) *Proc. Natl. Acad. Sci. USA,* 80: 1987–1991. Hybridization efficiency was high and background spots over chromosomes or glass were few. For instance, of 30 randomly selected metaphase figures, all exhibited labelling on the short arm of chromosome 1, and in all cases both sister chromatids were labelled. Of 65 fluorescent spots observed, only 5 were randomly dispersed over chromosomes, hence over 92% represented genuine hybridization.

Figure 7A:
FIGS. 7A–7H illustrates fluorescent detection of nuclear RNA and DNA sequences.
Figure 7B:
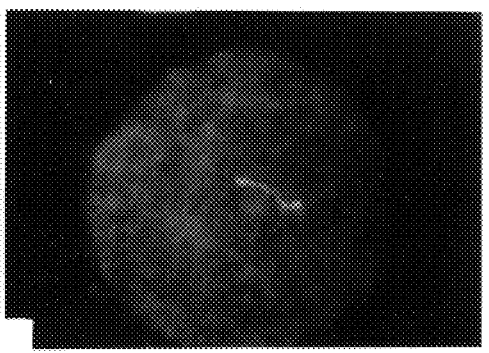

The conclusions that fluorescent spots observed in almost all interphase nuclei represented detection of EBV DNA was supported not only by the high signal-to-noise ratio on our samples, but also by the observation that the number and placement of the spots in nuclei was clearly nonrandom. Most nuclei had two spots that were closely spaced within 0.2–3.3 um of each other (FIGS. 7A–7C), whereas nuclear diameters ranged from approximately 10–24 um. Larger nuclei sometimes had two pairs of spots, as illustrated in FIGS. 7A and 7B. Since total DAPI fluorescence is directly proportional to DNA content (Coleman et al., 1981) *J. Histochem. Cytochem.* 29: 959–968, these larger nuclei appear to have a duplicated DNA content relative to diploid G1 cells, and therefore, would be expected to show twice as much signal. Further evidence that spots in interphase nuclei represented bona fide hybridization was that they were not observed in negative controls, such as hybridization with pBR322, hybridization of the EBV probe to nuclei of other cell types, or to nondenatured Namalwa nuclei, to DNAse-treated Namalwa nuclei.

Figure 6A:
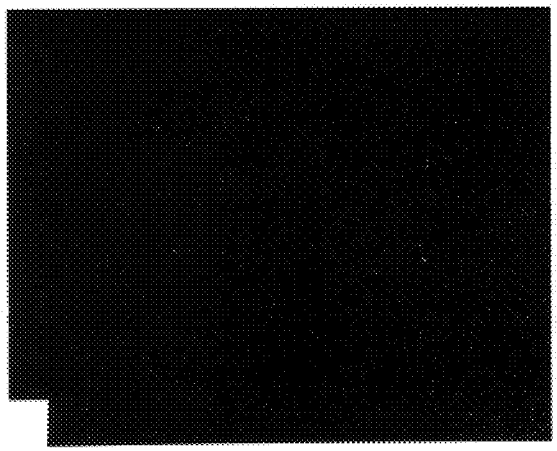
FIGS. 6A–6F are photographs of observed fluorescent spots within interphase nuclei which represent detection of Epstein-Barr virus DNA.
Figure 6B:
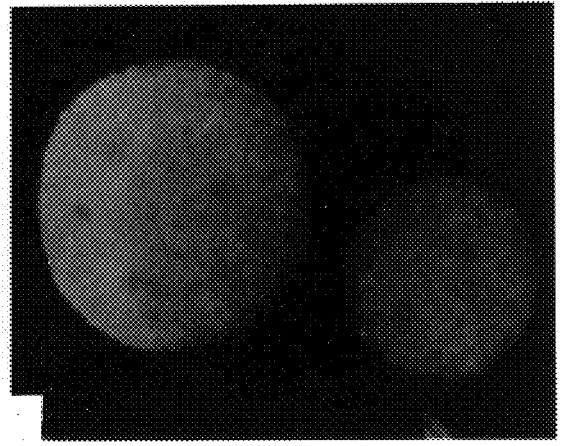
Figure 6C:
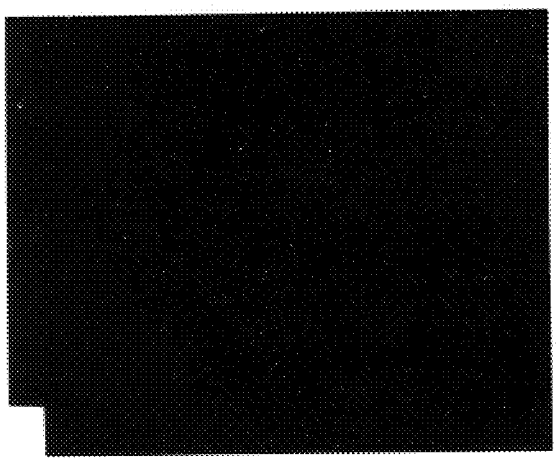
Figure 6D:
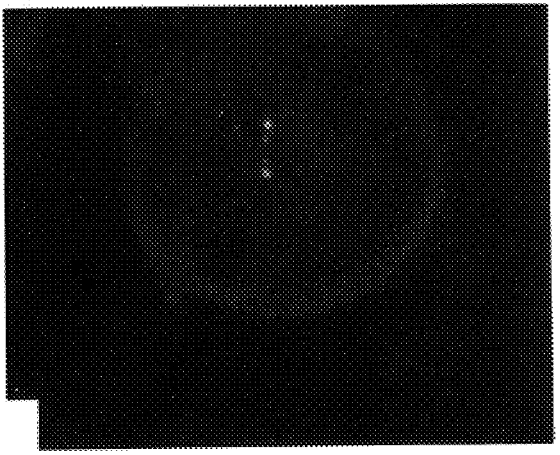

Next tested was a probe for the BamHI A fragment of EBV, which is a single sequence of 12 kb. When probe concentration of the EBV A fragment clone was increased from 0.2 ug/ml to 5.0 ug/ml, the intensity of fluorescent signal increased markedly, such that the signal with A probe was easily visualized on chromosomes as well as in nuclei (FIGS. 6C and 6D). Background was not significantly increased. As observed with probe to the W fragment, most nuclei had two closely spaced fluorescent spots. Of 20 randomly selected metaphase spreads, 18 were labelled on the short arm of chromosome 1 and, in 17 of these, both sister chromatids were labelled. In these experiments, even highly condensed, morphologically poor chromosome spreads generally exhibited hybridization.

Figure 6E:
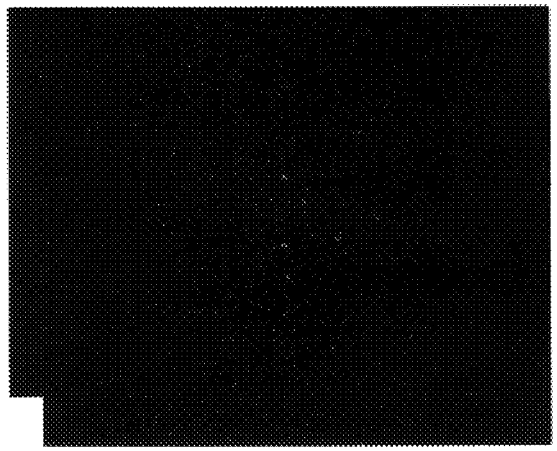
Figure 6F:
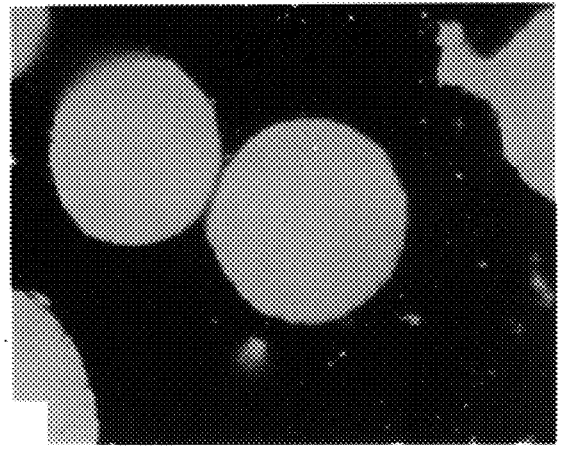

We next proceeded to still smaller probes of the EBV genome, using the Y/H fragment (7 kb) and the K fragment (5 kb) of viral DNA successively. Each of these probes generated visible signal that was localized at the appropriate site on the short arm of chromosome 1 (FIGS. 6E and 6F). Greater than 70% of metaphase spreads were labelled with either the Y/H or the K probe, and generally both sister chromatids showed signal. As with the W and A fragments, hybridization with either the K or Y/H most frequently produced a pair of closely spaced fluorescent spots within interphase nuclei (FIG. 7E). It should be noted that the K fragment signal was visible despite the fact that this fragment contains some repetitive sequences in the IR-3 region that have homology to cellular DNA (Heller et al., 1982) *Proc. Natl. Acad. Sci. USA,* 79: 5916–5920 and may cause a slightly higher fluorescence through the nucleus. Hence, these results demonstrate that this methodology is sensitive enough to detect as little as 5 kb of a single sequence.

Figure 5A:
FIGS. 5A–5F are photographs of fluorescent detection of single-copy in metaphase figures of Namalwa cells showing probe positions of each sister chromatid on the short arm of chromosome 1.
Figure 5B:
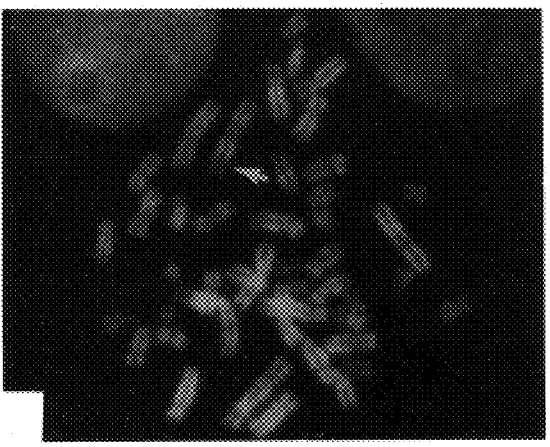
Figure 5C:
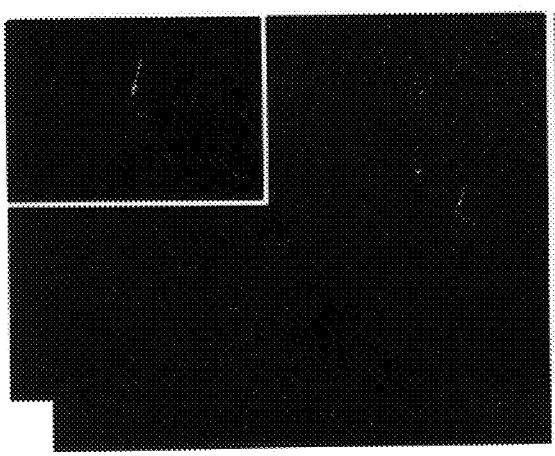
Figure 5D:
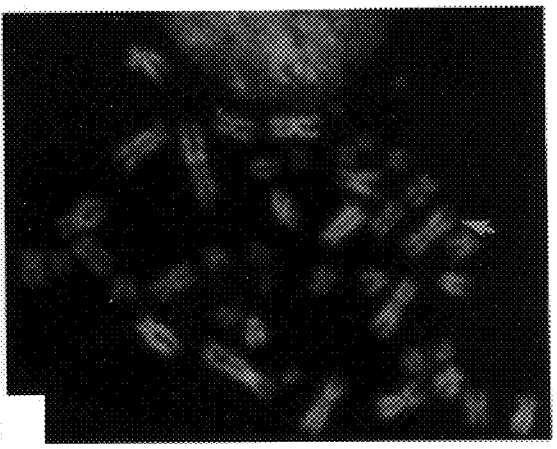
Figure 5E:
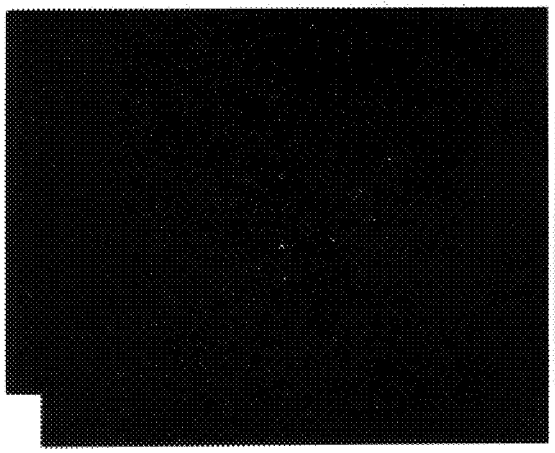
Figure 5F:
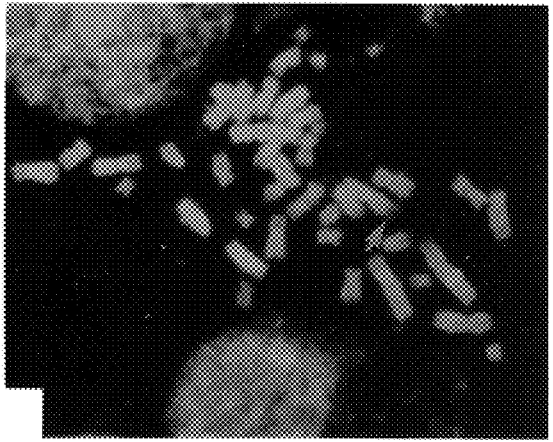

Our results and previous results using autoradiographic in-situ hybridization (Henderson et al., 1983 (*Proc. Nat'l. Acad. Sci. USA,* 80: 1987–1991) indicate that a single homolog of chromosome 1 is the only chromosome to exhibit label in Namalwa cells. Therefore, the consistent observation that, regardless of the EBV genome fragment used, closely spaced fluorescent signals are observed in most interphase nuclei strongly suggests that the two spots represent two copies of the EBV genome incorporated at this site on chromosome 1. The spots clearly had a nonrandom distribution with respect to each other in that the distance separating them exhibited a relatively narrow range of 0.2 um to slightly over 3 um. This result is consistent with two copies of EBV integrated close together on the same strand of DNA. The observation that larger nuclei, many of which may be either in G2 of the cell cycle of tetraploid, must frequently have two "pairs" of spots (FIGS. 7A and 7B) is further consistent with this interpretation. However, the most convincing evidence for two EBV genomes integrated at this site is that close examination of metaphase chromosomes, in which the DNA is more condensed and the two signals may coalesce, shows that the signal on each sister chromatid consists of a doublet (FIG. 5C insert A). High magnification (1,000×) revealed that in many or most metaphase figures the signal on each chromatid of chromosome 1 could be resolved as two very closely spaced fluorescent spots (up to 0.4 um apart.)

Analysis: Orientation and Proximity of the Two EBV Genomes

The presence of two EBV genomes would not be resolvable by autoradiographic in-situ hybridization used in previous studies (Henderson et al., 1983 (*Proc. Nat'l. Acad. Sci. USA* 80: 1987–1991). Our results indicating the presence of two viral genomes, coupled with evidence for only one set of viral-cell junction sequences, suggests that a duplication of viral and adjacent cellular sequences occurred during or after integration and has been stably maintained in this cell line.

To investigate the possibility that the two viral genomes are separated by cellular DNA, as well as to test further the resolving power of our technology, we conducted experiments to determine if hybridization to regions A and W, sequences at opposite ends of the EBV genome (FIG. 5), could be simultaneously and individually visualized within the interphase nucleus. Samples were reacted with a mixture of 5 ug/ml each of A and W probes and hybridization to the A fragment of each EBV genome could be visually resolved from hybridization to the corresponding W fragment, separated by 130 kb. This was indicated by the presence of four tightly clustered spots discernible in many interphase nuclei. Generally, two of the spots were dimmer and two were brighter, as evident in FIG. 7D. Since in any given experiment, samples hybridized with the A fragment (12 kb) consistently showed dimmer signal than samples hybridized under identical conditions with the W fragment (30 kb), we surmised that the two dimmer fluorescent spots represent A and that the brighter spots represent W. Note that the four uniformly bright spots observed in larger G2 or tetraploid nuclei hybridized with just W probe (FIG. 7A) are qualitatively different from the clustered spots of two different intensities observed in smaller (presumably G1) nuclei hybridized simultaneously with A and w. Occasionally, the configuration of these four spots appeared in an extended linear array, as illustrated in FIG. 7D. The arrangement of low and high intensity fluorescent signals in this linear array allows us to orient the two integrated EBV genomes as W-A-A-W. The presence of four distinct signals indicates a separation of the two genomes and is consistent with the duplication or insertion of cellular sequences between them. Furthermore, by comparing the W-A distances to the A—A distance, we can estimate the amount of DNA separating the two genomes. For example, in the cell in FIG. 6B, the distance between W-A (Bright-dim) was in both cases 0.9 um, whereas the distance between A—A was 1.5 um. Since it is known that W and A are approximately 130 kb apart in each EBV genome, we estimate that the two genomes are separated by roughly 220 kb of DNA.

If the orientation of the integrated viruses is indeed W-A-A-W, as the above results suggest, then the distance between the two signals generated by hybridization with the BamHI A probe alone should be, on the average, less than that generated with just the BamHI W probe. Separate hybridizations with each probe were conducted and the average distance between paired signals was determined from photographs of randomly chosen cells. Based on 125 determinations of the distance between paired signals with the A probe, the average distance (+95% confidence limits) was 0.99 (+0.093) um. In contrast, the average distance between the two fluorescent spots of each pair was 1.74 (+0.144) um for the W probe based upon 150 determinations. The difference between these two means is highly significant statistically with P less than 0.001, confirming the above results that indicate that the EBV genome is integrated as an inverted repeat in a W-A-A-W orientation. These data also provide an independent and more accurate means of assessing the distance between the two genomes based on a large statistical population. From this approach, we calculate that approximately 340 kb of DNA separates the two viral genomes. The two estimates of this distance (220 kb and 340 kb), which were derived by two different approaches, are relatively close, given the expected difficulty of approximately molecular distances based on in-situ hybridization.

Is the EBV Genome Randomly Localized in Interphase Nuclei?

The ability to detect individual DNA sequences within interphase nuclei allows us to examine the nuclear localization of these sequences. During the course of these experiments, it was consistently noted that the EBV genome, integrated into the short arm of chromosome 1, was not detected near the periphery of the nucleus but occupied a more central region. As illustrated in FIG. 8, signal was almost never observed in the area of the nucleus circumscribed by the outer 20% of the radius, even though this spheroid consititues 49% of the nuclear volume. These results indicate that the EBV integration site on chromosome 1 is nonrandomly localized within an inner sphere of the nucleus representing only 51% of the nuclear volume.

EXAMPLE 2

Fluorescence Detection of Nuclear and Cytoplasmic RNAs

Another strength of the present methodology is the ability to visualize nuclear RNAs close to the time of initial gene expression. The methods described herein provide straight forward test conditions which allow for: detection of RNA alone; detection of DNA alone; and detection of RNA and DNA concurrently. The methods described below have been reproduced with more than 90% success for periods of time greater than six months in duration.

Method

The methodology previously described within Example 4 for fluorescence detection of single-copy nuclear DNA was modified so as to allow direct visualization of specific nuclear RNA. From evaluation of a number of technical parameters, it was found that omission of denaturation, heat treatment, and RNAse treatment, coupled with frozen storage of slides and careful selection and quality control of key reagents, allowed repreducible detection of nuclear RNA with the high resolution of fluorescence microscopy. Transcripts synthesized from an integrated Epstein-Barr Virus (EBV) genome in a human lymphoma cell line were investigated. This latently infected cell line, Namalwa, contains two copies of the EBV genome closely integrated on chromosome 1 and does not contain spisomal genomes (Henderson et al., 1983 Proc. Natl. Acad. Sci. USA, 80: 1987–1991).

Biotin-labelled DNA probes representing specific fragments of the EBV genome were hybridized to interphase nuclei in cytogenetic preparations of Namalwa lymphoma cells and hybrids detected with fluorescein avidin. The probe was a plasmid containing the Bam H1 W fragment (Bam W) of the EBV genome.

The Bam W region is a 3 kb sequence, tandemly repeated 6–10 times in the EBV genome, hence representing 18–30 kb of NA (Henderson et al., 1983 *Proc. Natl. Acad. Sci. USA,* 80: 1987–1991). Bam W sequences are represented in nuclear RNA of Namalwa cells and primary transcripts up to 20 kb long containing these sequences are extensively spliced to form the 3 kb LT-1 mRNA, present in low levels in polyadenylated cytoplasmic RNA (van Santen et al., 1983, *Proc. Natl. Acad. Sci USA,* 78: 1930–1934; Dambaugh et al., 1986, in *The Epstein-Barr Virus: Recent Advances;* Epstein and Achong (Eds.), New York, John Wiley & Sons, pp. 13–45.

In-Situ Hybridization

Non-isotopic in-situ hybridization with the EBV Bam W probe under the appropriate conditions revealed a striking localization of these RNA sequences within interphase nuclei. The transcripts detected were highly restricted to a specific site in each nucleus, with accumulated transcripts forming a bright fluorescent focus which appeared as a curvilinear fluorescent structure or track of specific mRNA. No such structures were ever observed after hybridization with biotinated pBR322 probe.

Figure 7C:
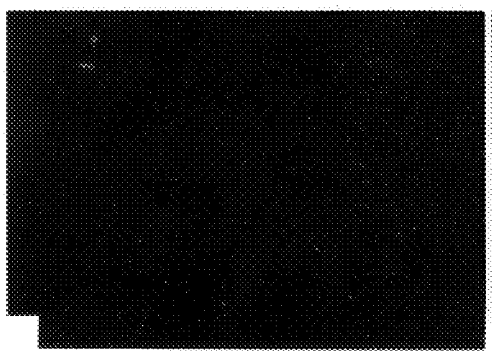
Figure 7D:
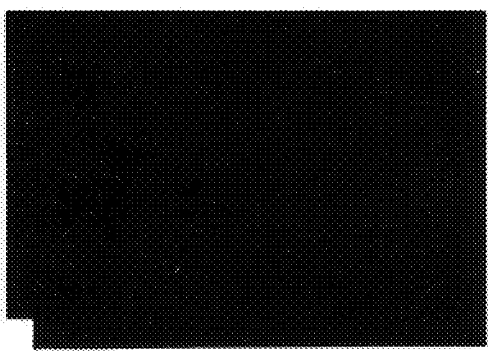
Figure 7E:
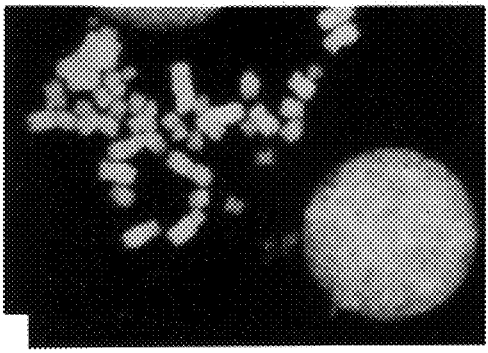
Figure 7F:
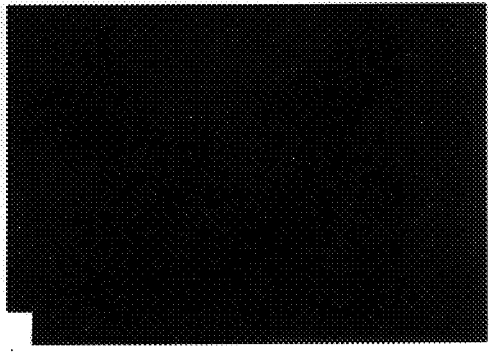
Figure 7G:
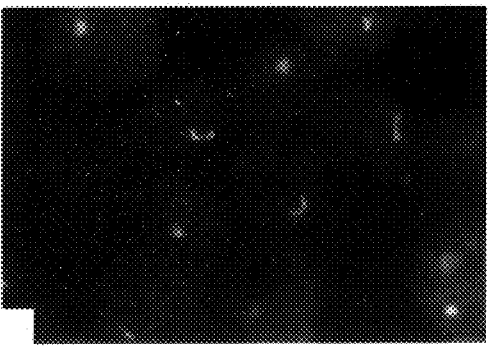
Figure 7H:
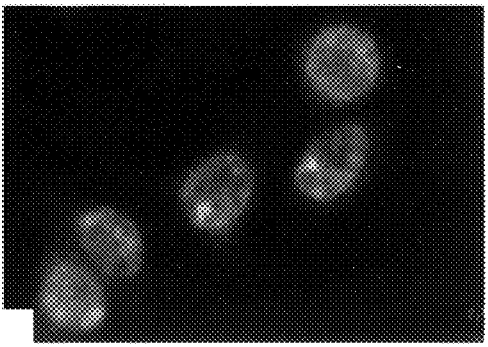

Results using several different experimental strategies definitively support the conclusion that these structures represent detection of nuclear transcripts. 1) In samples for which DNA had been denatured prior to hybridization, Bam W sequences are detected at the EBV integration site on metaphase chromosome 1, as well as in interphase nuclei (FIG. 7C). However, if denaturation of double-stranded DNA is omitted prior to hybridization, there is no detectable hybridization to metaphase chromosomes (which do not transcribe RNA), but fluorescent tracks are still observed in interphase nuclei (FIGS. 7E and 7F). 2) In non-denatured preparations all nuclear signal is removed by treatment with RNAse H after hybridzation. In denatured preparations treated with RNAse H (FIG. 7D), signal is reduced to just two closely-paired spots in interphase nuclei, representing two closely integrated viral genomes, as previously described [Lawrence et al., 1988] *Cell,* 55: 51–61. 3) Cells were treated with actinomycin D prior to fixation in order to inhibit transcription and were hybridized without prior denaturation of DNA. Fluorescent nuclear signals were diminished in size and intensity by a 1 hour incubation in actinomycin D and were essentially eliminated by a 4–5 hour incubation. 4) Finally, the degree to which different fragments of the EBV genome are transcribed in Namalwa cells has been well characterized by conventional filter and solution hybridization techniques [reviewed in Dambaugh et al., 1986], in *The Epstein-Barr Virus: Recent Advances;* Epstein and Achong (Eds.), New York, John Wiley & Sons, pp. 13–45.

In-situ hybridization was performed with probes for four different fragments of the EBV genome, two of which are known to be heavily transcribed (Bam H1 fragments W and Y/H), one of which is transcribed at lower levels (Bam H1 K), and one which is not transcribed in this line (Bam H1 A). As illustrated in FIG. 10, there was a good correlation between the in-situ assay and conventional hybridzation results. The most prominent RNA signals were observed for the W and Y/H probes, fainter signals with the K probe (not shown), and essentially no RNA signal using the A probe.

Detection of Primary Transcripts Within the Nucleus of Intact, Paraformaldehyde Fixed Cells The above experiments were performed on interphase nuclei present in standard cytogenetic preparations which had been swollen in hypotonic solution, fixed in methanol:acetic acid, and dropped on glass-slides to promote nuclear flattening and eliminate surrounding cytoplasm. To broaden the general applicability of this technique, it was desirable to adapt our techniques for detection of RNA within the nuclei of morphologically preserved intact cells. The steps in the cytogenetic protocol were individually evaluated and changed where appropriate to derive a protocol for nuclei of intact cells. We found that intact cells grown in suspension could be gently adhered to glass slides (Lab-tek), directly fixed in 5% paraformaldehyde, stored in 70% EtOH, and then hybridized and detected by the same protocols used for isolated nuclei. The quality of the hybridization obtained for nuclei of intact [Lawrence et al., 1988 *Cell* 55:51–61]. Nuclear transcripts were detected in essentially all nuclei and the operational sensitivity limit, as indicated by detection of single-copy DNA in individual nuclei, was 5 kb. Representative cells showing hybridization to nuclear RNA are shown in FIG. 9G.

Detection Of A Non-Viral Nuclear RNA Abundantly Expressed In the Cytoplasm

In the above experiments, the detection of EBV nuclear RNA may have been facilitated by the accumulation of these RNAs within the nucleus of latently infected cells. Because the mature 3 kb mRNA molecules are small and contain segments homologous to our probes and little is transported to the cytoplasm [approximately 3 molecules of LT-1 per cell; van Santen et al., 1983; Dambaugh et al., 1986], essentially no RNA is detected in the cytoplasm of intact Namalwa cells with either the Bam W, Bam K, or Bam Y/H probes. It was of interest to determine whether a nuclear signal could be detected for non-viral RNA which was expressed at high levels in the cytoplasm. Intact 3T3 cells stably transfected with a plasmid containing neu oncogene cDNA (erb B2) provided a convenient non-viral test system since these cells over-express this sequence and the mature mRNA is large enough to detect readily by fluorescence microscopy. Control samples included non-transfected 3T3 cells or transfected 3T3 cells hybridized with a non-homologous probe (HIV probe). Denaturation of double-stranded DNA prior to hybridization was omitted to ensure that signal represented RNA hybridization. As shown in FIG. 9H, both nuclear and cytoplasmic neu onocogene RNA was successfully detected in the transfected cells expressing this MRNA at high levels. The brighter nuclear signals can be visualized despite the diffuse cytoplasmic fluorescence. Most cells contained a single site of concentrated nuclear RNA, although occasional cells contained several nuclear foci and other none. Due to the more three-dimensional nature of these cells, the nuclear signal is not in focus in all cells (FIG. 9H); however, there was excellent correlation between the presence of the foci of nuclear RNA and the presence of cytoplasmic RNA. As visible in FIG. 9H, cytoplasmic RNA was apparent as a diffuse punctate staining throughout the cytoplasm, frequently with brighter fluorescence in the thicker perinuclear region. That this represented bona fide detection of neu oncogene RNA was indicated not only by the correlation between cytoplasmic and nuclear signal in non-transfected 3T3 cells or in the same cells hybridized with biotinated EBV probe (not shown). These results show that the ability to detect nuclear RNAs is not exclusive to viral infection.

EXAMPLE 3

HIV Detection Using Labelled Probes and Alkaline Phosphatase

Rationale T he development of a rapid, sensitive, and convenient non-radioisotopic in-situ hybridization assay to detect the viral genome directly would increase the likelihood of detecting all HIV infected donors prior to the transfusion of contaminated blood products. A direct method of HIV detection would also be extremely useful in those situations when antibodies are not informative; e.g., in infants of seropositive mothers where passively acquired maternal antibodies obscure the diagnosis and in those HIV infected individuals who fail to mount an appropriate antibody response or lose the ability to maintain HIV specific antibody following acute infection. Finally, a more quantitative assessment of HIV infection will be helpful in assessing natural history of infection and monitoring antiviral therapy.

This series of experiments describes the combination of enzymatic non-isotopic detection with the methodology for in-situ hybridization to detect HIV in a variety of cellular samples. This affords a rapid, yet convenient sensitive and reproducible technique. The method uses non-isotopic detection methods with the probe for the viral genome being labelled by biotinyl-dUTP. The biotinylated probe is then detected by a variety of methods: streptavidin followed by biotinylated alkaline phosphatase, or streptavidin conjugated directly to alkaline phosphatase. A schematic diagram of the preferred technique established in this work is depicted in FIG. 11. In addition, we have used alkaline phosphatase directly conjugated to an oligonucleotide probe (manufactured by Molecular Biosystems, Inc. and marketed by Dupone as "SNAP" probe).

In-Situ Hybridization

Cells were washed in PBS, and applied to multi-well serologic slides (Cel-line, 5 mm wells) at a concentration of $30 \times 10^6$/ml. Fifty ul is placed on the well and withdrawn with pipet tip leaving cells to be air dried (10 minutes), and fixed in 2% paraformaldehyde in PBS (5 minutes), and stored in 70% ethanol at 4 C.

Probe Preparation by Nick-Translation 1 ul of 400 uM biotin dUTP (BRL) 1 ul of dACG mix (dATP, dCTP, dGTP 600 uM each, PL Biochemicals), 1 ul of 10×nick-translation buffer (0.5 M Tris Cl, ph 7.2; 0.1 mM $MgSo_4$; 1 mM dithiothreitol) 500 ug/ml bovine serum albumin; BSA Pentax Frac V) 5 ul steirle glass distilled $H_2O$; 1 ul of 0.1 ug/ul HIV DNA (entire 9 kb genome), 1 ul of DNAse (final 34 ng/ml: concentration determines the probe size; large probe sizes cause background), 1 ul of DNA Pol I (Boehringer). Incubation for three hours at 15 C., then 90 ul of 50 mM EDTA and 1 ul of 10% SDS is added. Purification from free nucleotides is with a sterile G50 SEPHADEX "spin" column packed in a 1 ml disposable syringe.

Prehybridization

Slides stored in 70% alcohol are rehydrated in a ten minute PBS, 5 mM MgCl bath then ten minutes in 0.1 M Tris—0.2 M glycine, prior to formamide, 4×SSC incubation. Ten to fifty ng of probe DNA is used which can be obtained by aliquoting 10 ul of nick-translated probe into an eppendorf tube and lyophilizing it with two lambda of carrier nucleic acids (1 mg/ml of sheared salmon sperm and tRNA). Ten ul of deionized formamide is mixed with the lypholite and placed in a 90 C. heating block for ten minutes. Hybridization buffer is prepared by mixing 30 ul 20×SSC; 30 ul BSA, 60 ul dextran sulfate (50% solution, autoclaved in water) and 30 ul water. Slides are then quickly utilized after blotting away excess solution with the deposition of the heated probe mixed rapidly with an equal 10 ul of hybridization buffer onto each serological well, covered with a small strip of parafilm, placed for three hours (or overnight as is convenient) in a humidified 30 C. incubator. Slides are rinsed in 50% formamide/4×SSC for thirty minutes at 37 C, then placed in 2×SSSC for 30 minutes and finally in 1×SSC for 30 minutes (or overnight).

Detection

Streptavidin-alkaline phosphatase after the method of Singer et al., (1986) *Biotechniques*, 4:230–250 was used. A streptavidine-alkaline phosphatase conjugate (Dakopatts) was used with a dilution 1:250 into 4×SSC with 1% fatty acid free BSA and exposed to the hybridized cells for 10 minutes. After washing in 4×SSC (3 washes for 10 minutes each) the cells were put into the pH 9.5 wash previous to color development with NBT and BCIP (developed 10–30 minutes).

Sensitivity of Assay

In-situ hybridization, by providing information as to numbers infected cells, provides a means of rigorous evaluation of sensitivity of detection. While applying this approach, we first investigated sensitivity as defined by situations where positive cells are very rare (less than one in $10^4$). This was modeled by use of a mixing experiment where virus-positive cells are diluted by negative cells serially to extinction and the percent positive cells as function of dilution determined by in-situ hybridization and compared to aliquots taken for dot blot filter hybridization or the indirect immunofluorescence assay (FIG. 12). In this experiment, using the non-isotopic detection methodology quantitatively accurate information with each dilution (1:1 with uninfected cells) through 10 dilutions eventually reaching approximately a thousand fold dilution. Since the original infected cell culture contained only 1 positive cell per 14, these dilutions were accurate to one infected cell per 14,000 (FIG. 12A). The false-positive rate was determined by using an uninfected population of cells and was found sufficiently low (less than $10^{-5}$) that a single positive cell could be detected with confidence in 50,000 negative cells.

To compare these reagents with each other as well as to isotopically labelled probes, we used a model system to test sensitivity for detecting fewer copies of HIV per infected cell. In this experiment, we used a freshly infected culture of normal PHA activated T-lymphocytes. Infected cells were enumerated at daily intervals for one week comparing in-situ techniques employing the various detection systems. Representative experimental result graphically displayed in FIG. 13 demonstrate that these approaches are convenient and rapid means for identifying cells infected with HIV. Both the isotopic and non-isotopic detection of in-situ hybrids using the full genomic probe were of comparable sensitivity and the least sensitive was about a factor of twenty (i.e., twenty time more cells on a given time point). The mixture of these oligonucleotides has acceptable sensitivity but only after an overnight exposure to the chromagen; it is possible that additional oligonucleotides added to the mix would increase sensitivity proportionately.

Results

To become useful clinically, the in-situ hybridization approach must be able to detect infected cells from patients. In order to establish the efficacy of this approach, we have hybridized patient mononuclear cells co-cultured with normal human T-lymphocytes, as well as direct hybridization of patient mononuclear cells without co-culture. The co-culture technique with in-situ hybridization is schematically illustrated in FIG. 14. In order to correlate the information with an established HIV detection technique, we compared all samples with an ELISA test for the p24 viral antigen (Dupont). The results of this test on two different patient populations are shown in Table 1.

To obtain the data of Table 1, samples were isolated from seropositive individuals and cultured with normal lymphocytes stimulated with PHA and IL-2. At four intervals over the next 21 days the same culture was tested and if any one of those days was positive, the sample was considered positive. For in-situ hybridization, 1 cell per 10,000 was sufficient for a positive. For the P24 antigen capture ELISA, three sample was assayed as described by Dupont: 200 ul of supernatant was test, an O.D. greater than 0.039 was considered positive (recommended cutoff in the ELISA manual). For direct detection, patient lymphocytes were put directly on slides and processed as described previously.

TABLE 1

| PATIENT SAMPLE (number) | METHOD | ANTIGEN CAPTURE POSITIVE (%) | IN-SITU HY-BRIDIZATION POSITIVE (%) |
|---|---|---|---|
| Hemophiliacs (34) | Co-culture 21d | 9 (27%) | 18 (54%) |
| Infants (14) | Co-culture 21d | 5 (35%) | 9 (63%) |
| Clinic (45) | Directly on patient lymphocytes | — (9%) | 12 (27%) |

As identified by Table 1, one population consists of hemophiliacs which are seropositive but asymptomatic; the other, infants of seropositive mothers. In-situ hybridization detects virus positive cells in 50–54% of both groups during a three week co-culture with normal T-lymphocytes. The p24 antigen capture ELISA test detected 27–33% positive in identical samples, all these samples were also positive by in-situ hybridization. Repeated samplings gave similar results. From this summary it can be seen that in-situ hybridization is the preferred method for sensitivity, detecting almost twice as many patient samples as the antigen capture test.

Once a statistically meaningful sample (over 100 patients) had been examined by non-isotopic in-situ hybridization, it was of immediate interest to test these patients directly, without co-culture with normal lymphocytes. The same population investigated with co-culture was used for the direct testing and it was found that approximately half as many of the patients were detected positive by this method (25–27%) as were detected with co-culture. Additionally, these patients varied in their virus positive cells detected in this way from 1 cell to 10 cells per 20,000. The CD4 positive cells of these patients were also assessed, but no obvious correlation was found between CD4 lymphocytes and number of viral infected circulating mononuclear cells. FIG. 5 shows representative non-isotopic detection of HIV nucleic acids in patient samples following co-culture and by direct detection using freshly isolated mononuclear cells.

Significance of Data

While further expected increases in sensitivity and convenience will doubtless make non-isotopic in-situ hybridization a viable alternative to other means of examination of patient, there are some aspects of this approach for which an advantage exists immediately. Foremost, the single cell nature of the data allows a quantative evaluation of viral-infected cells as percent infected. This will allow a direct evaluation of the effects of therapeutic drugs by their supression of the number of infected cells. Second, the approach can be used, as shown above, to detect virus positive cells in infants of seropositive mothers, where maternal antibodies or antigens may confuse the prognosis. Third, it provides a more rapid, accurate, and convenient alternative to virus culture. Fourth, it requires no specialized equipment other than a microscope, nor does it require skilled molecular biological expertise; the time required to complete the assay is one day and could be shortened considerable (to four hours). This makes it the shortest of the viral detection assays. Coupling the in-situ hybridization assay with automated scanning devices is expected to make the procedure compatible with mass screening of normal blood donors.

In-Situ Hybridization Protocol for HIV Detection
Contents of Kit

1. Control slides: (store at 40° C.)
   Positive cells
   Negative cells
2. Formamide—in-situ grade, 100 ml. (store at 4° C.) Caution: Caustic
3. Detergent solution, 100 ml.
4. HIV probe—biotinylated, 5 vials, 200 ng each, lyophilized (store at 4° C.).
5. 20×Saline Sodium Citrate (SSC), 250 ml.
6. Detector solution, 150 ml.
7. Hybridization buffer—300 ul. (store at 4° C.)
8. 0.1 M Triethanolamine (TEA), 150 ml.
9. Acetic Anhydride—3 ml.
10. Avidin-Alkaline phosphatase reagent
11. NBT, 600 ul. (store at −20° C.)*
12. BCIP, 600 ul. (store at −20° C.)* Caution: Wear gloves when handling.
13. Triton X-100™, 100 ul.
14. Parafilm strips
15. 1% Super Bovine Serum Albumin (BSA) in 4×SSC 1 ml. (store at −20° C.)
16. Paraformaldehyde fixative solution.

*NOTE: This should be made fresh if possible. Otherwise use these.

Reagent Preparation
1. Phosphate Buffered Saline (PBS):

| | |
|---|---|
| 1 Liter - weigh 80 gm | NaCl |
| 2 gm | KCl |
| 2 gm | KH$_2$PO$_4$ |
| 21.6 gm | NaHPO$_4$.7H$_2$O |
| Bring volume up to 1 L with distilled H$_{20}$ | |
| Adjust pH to 7.2–7.4: Increase pH with Sodium | |
| | Hydroxide |
| | Decrease pH with |
| | Hydrochloric Acid |

2. 4×SSC: 1 Liter Add 200ml 20×SSC to 800 ml Distilled H$_2$O
3. "Prehybridization Solution."
   a. Add 125 ul acetic anhydride to 50 ml of 0.1M TEA
4. 2×Saline Sodium Citrate (SSC): 500 ml Add 250ml 4×SSC to 250 ml Distilled H$_2$O
5. "Prehybridization Incubation Solution:"
   a. Add 100 ml 100% formamide to 100 ml 4×SSC. Heat to 70° C. for use.
6. Ethanol (ETOH):
   a. 70%-ADD 210 ml Distilled H$_2$O to 90 ml 100% ETOH
   b. 95%-ADD 285 ml Distilled H$_2$O to 15 ml 100% ETOH
7. 1×SSC: 200 ml
   Add 10 ml 20×SSC to 190 ml Distilled H$_2$O
8. An aliquot (1 ml) of hybridization buffer (Reagent 7) should be heated to 37° C. for use in Step B4.
9. Color Reagent: Dilute 5 ul avidin/alkaline phosphatase reagent into 1 ml BSA dilulent.
   (Dilution of 1:200) This should be prepared immediately before beginning Section D.
10. Avidin/alkaline Phosphatase Wash:
    Add 200 ul of 0.1% triton X-100™ to 200 ml 4×SSC
11. Reaction Detector Solution:
    Add 132 ul to 30 ml detector solution. Mix. Add 100 ul BCIP. Mix.

Required Equipment & Materials
1. Shaker
2. Coplin Jars
3. 37° C. water bath
4. 70° C. bath
5. 90° C.
6. Moist covered chamber and rack for slides
7. 37° C. tissue culture incubator
8. Microscope
9. Pipets and Tips A. Prehybridization
1. Remove specimens (slides) from 70% ETOH storage fluid and rehydrate in 2×SSC for two minutes.
2. Treat slides (rehydrated from step 1) with detergent solution for ten minutes.
3. Wash slides twice in 2×SSC for five minutes per wash.
4. Treat slides with prehybridization solution for 10 minutes.
5. Wash slides twice in 2×SSC for 5 minutes per wash.
6. Incubate slides at 70° C. in prehybridization incubation solution for two minutes. (Incubation is coincident with probe heating at 90° C., see step B.1–2). (Save prehybridization mixture for posthybridization wash. Store at 4° C. until used).
7. Dehydrate through 70–95–100% ETOH for 2.5 minutes per dehydration.
Slides are now prepared for hybridization B. Hybridization
1. Reconstitute lyophilized HIV probe by adding 50 ul of 100% formamide to each vial.
2. Place HIV probe in heating block at 90° C. for 10 minutes (coincident with step A6).
3. Add 50 ul of 37° C. hybridization buffer (Prepared reagent #8) to each vial of HIV probe. (This is a 1:1 volume/volume ratio)
4. *Immediately add 10 ul of probe to each well. Seal with parafilm strips and put onto a rack in a moist covered chamber. Place chamber in a 37° C. tissue culture incubator to hybridize for a minimun of four hours, overnight is preferable.
*NOTE: Do not allow wells to become dry.

C. Posthybridization*
1. Incubate slides at 37° C. in prehybridization mixture saved from step A6 for 30 minutes.
2. Incubate slides at 37° C. in 2×SSC for 30 minutes.
3. Wash slides in 1×SSC for 30 minutes on shaker.
*NOTE: Heat buffer saved from Step A6 prior to beginning this section.

D. Avidin/Alkaline Phosphatase Reaction
1. Incubate slides, at room temperature, in 4×SSC for 10 minutes.
2. *Place 20 ul of reagent on each sample well (amount should be ample), cover with parafilm strips and allow to react at room temperature, for 30 minutes.
3. Wash slides at room temperature, in 4×SSC, for 10 minutes, on shaker.
4. Wash slides at room temperature in Avidin/Alkaline Phosphatase wash for 10 minutes.
5. Wash slides at room temperature in 4×SSC for 10 minutes.
*NOTE: Do not allow to dry totally. Tissue/cells should be damp.

E. NBT/BCIP Staining (Wear gloves)
1. Warm reaction detector solution (Prepared reagent 11) to 37° C. P1 2. Pour solution into a coplin jar. Place slides from step D5 in the jar and incubate at 37° C. for 40 minutes to an hour.*
3. Rinse slides twice in PBS, then rinse once in distilled water.
4. Allow slide to air dry.
5. Mount slides with distilled water and cover glass for scoring under microscope. Store dry.
*Slides should be monitored for color development to avoid overdevelopment of background. Check after 15–20 minutes. Dry bottom of positive control slide, view as a wet mount. In addition, check one sample slide in the same manner. Return to jar if color development is incomplete.
(NOTE: Slides may be incubated in another suitable slide container and covered with an appropriate volume of detector solution.)

EXAMPLE 4

Detection of HIV Nucleic Acids Within Infected Cells Using Fluorescence as the Means for Detection The same descriptive detail and rationale applies to the detection of HIV in patient derived samples using fluorescence as the basis of detection as was elucidated in Example 3 previously using enzymatic means for detection. There are, however, a number of advantages to using fluorescence as the detection means. Of these, the major one is sensitivity which results from the resolution of fluorescence directly at the actual site of nucleic acid hybridization. With HIV infected cells, this degree of resolution becomes essential because the HIV has been found to replicate in a very small sized region within the nucleus of the cell, a pin-point area termed "a focus of replication." As seen in FIG. 15, this focus of replication of fluorescence pin-point is the nuclear area in which the viral RNA is being produced and which eventually will result in new virions budding from the cell.

The first events after actual HIV infection, however, are the establishment of the viral RNA within the human host cell; and then the production of new DNA through the viral enzyme, reverse transcriptase. After its formation, the viral DNA translocates into the nucleus of the host cell and inserts itself into the genetic material of the human host cell, typically a lymphocyte. This reverse progression of viral RNA to viral DNA, followed by insertion of viral DNA into the genome of the host cell gives this class of viruses its name, Retrovirus. After the viral DNA is integrated into the nuclear sites of the host cell, a rapid production of new viral RNA occurs. It is at this point in the sequence of cellular events that the high sensitivity of the present methodology can detect the presence of actual HIV infection. No conventionally known assay method of technique is capable of detecting an HIV infection at this stage. Only the present invention is able to accurately detect the presence of HIV at this event so close to the moment of actual infection of the host cell by the HIV.

As will be described hereinafter, empirical data shows the observed pin-point of fluorescence to be new viral RNA because: (a) the fluorescence pin-point is present without use of denaturing conditions, hence the localized nucleic acid is single stranded; (b) the fluorescence pin-point disappears in the presence of actinomycin, a transcription inhibitor; and (c) the fluorescence pin-point is lost after reaction with ribonuclease. In addition, the fluorescence pin-point identifies an initial event in the infectious process because the fluorescence appears within the kinetics of a times, intentional infection of human cells first at only 12 hours after actual infection, when viral RNA is just beginning to be synthesized; because the fluorescence pin-point can be observed before cytoplasmic viral RNA is apparent (i.e., before RNA production truly gets underway); and because the fluorescence pin-point is never seen in uninfected cells or within cells tesed using probes representative of a different virus.

The highly sensitive single-copy detection capability provided by the present invention independently also allows for the detection of HIV when it first enters into the proximity of the endogenous DNA of the host cell. This unique capability allows the user to effectively screen patients for latent virus, non-integrated viral DNA within the nucleus of the cell; and equally important, alternatively allows for detection of fully integrated, activated virus able to produce new viral RNA for new virions. The ability to identify and distinguish among these alternative stages and circumstances is clinically important since most individuals infected with HIV go through a long latent time period of about 5–7 years before the virus activates. Accordingly, it is critically important for an effective therapeutic regimen that the physician know whether the HIV is activated and when this event occurred. It is expected that this period of viral latency will be the ideal time to administer pharmacologically active compositions against HIV. The manipulative steps described hereinafter are thus capable of substantially adding to the present state of knowledge and control of this disease.

Preferred Method for Detecting HIV Nucleic Acids Within Infected Cells
In-Situ Hybridization Cells were washed in PBS, and applied to multi-well serologic slides (Cel-line, 5 mm wells) at a concentration of $30 \times 10^6$/ml. Fifty ul is placed on the well and withdrawn with pipet tip leaving cells to be air dried (10 minuted), and fixed in 2% paraformaldehyde in PBS (5 minutes), and stored in 70% ethanol at 4 C.

Probe Presentation by Nick-Translation 1 ul of 400 uM biotin dUTP (BRL) 1 ul of dACG mix (dATP, dCTP, dGTP 600 uM each, PL Biochemicals), 1 ul of 10×nick-translation buffer (0.5 M Tris Cl, pH 7.2; 0.1 mM $MgSO_4$; 1 mM dithiothreitol) 500 ug/ml bovine serum albumin; BSA Pentax Frac V) 5 ul sterile glass distilled $H_2O$; 1 ul of 0.1 ug/ul HIV DNA (entire 9 kb genome), 1 ul of DNAse (final 34 ng/ml: concentration determined the probe size; larger probe sized cause background), 1 ul of DNA Pol I (Boehringer). Incubation for three hours at 15 C., then 90 ul of 50 mM EDTA and 1 ul of 10% SDS is added. Purification from free nucleotides is with a sterile G50 sephadex "spin" column packed in a 1 ml disposable syringe.

Pre-Hybridization

Slides stored in 70% alcohol are rehydrated in a ten minute PBS, 5 mM MgCl bath then ten minutes in 0.1 M Tris—0.2 M glycine, prior to formamide, 4+SSC incubation. Ten to fifty ng of probe DNA is used which can be obtained by aliquoting 10 ul of nick-translated probe into an eppendorf tube and lyophilizing it with two lambda of carrier nucleic acids (2 mg/ml of sheared salmon sperm and tRNA). Ten ul of deionized formamide is mixed with the lypholite and placed in a 90 C. heating block for ten minutes. Hybridization buffer is prepared by mixing 30 ul 20×SSC; 30 ul BSA, 60 ul dextran sulfate (50% solution, autoclaved in water) and 30 ul water. The slides were then heated at 70 C. in 70% formamide for two minutes for purposes in detecting DNA within the lymphocytes. For purposes of detecting RNA within the cells, this last step is omitted.

Slides are then quickly utilized after blotting away excess solution with the deposition of the heated probe mixed rapidly with an equal 10 ul of hybridization buffer onto each serological well, covered with a small strip of parafilm, placed for three hours (or overnight as is convenient) in a humidified 30 C. incubator. Slides are rinsed in 50% formamide/4×SSC for thirty minutes at 37 C., then placed in 2×SSC for 30 minutes and finally in 1×SSC for 30 minutes (or overnight).

After rinsing, the slides are washed briefly with 4×SSC buffer and then exposed to avidin-fluorescein (2.0 ug/ml) in 4×SSC buffer containing 1% bovine serum albumin for 20 minutes. Afterwards the slides are then mounted in DABCO and viewed with epifluorescence optics.

EXAMPLE 5

Detection of Cellular or Viral Nucleic Acid Sequences Using Probes Conjugated Directly to a Non-Isotopic Detector If desired, the detection of single-copy nucleic acids can be performed using nucleic acids conjugated directly to a fluorochrome or an enzyme as a hybridization probe. The nucleic acids comprising the probe may be long in length (such as recombinant molecules grown in bacteria) or comparably short sized entities (such as synthesized oligonucleotides). With long length probes, the fluorochrome (or enzyme) is directly linked into the nucleic acid strand by conventionally known nick-translation after a nucleotide analogue containing a linker arm is first enzymatically introduced. The fluorochrome is then chemically conjugated to the linker arm using known techniques. In the alternative, oligonucleotides can be synthesized with a linker arm inserted chemically into the sequence, or nucleotides can be added to either the 5' of 3 end of the nucleic acid sequence using known reactions and reagents. Each of these alternatives has been empirically evaluated for use in the improved in-situ hybridization methodology previously described herein. The preferred approach has shown that the synthesis of oligonucleotides having from 20–50 bases is most desirable when a fluorochrome or enzyme detector molecule is to be joined chemically to the probe.

Empirical evidence also demonstrates that direct conjugation of a non-isotopic detector molecule to the nucleic acids of a non-synthetic (i.e., recombinant nucleic acids grown in bacteria) DNA probe is also possible; as is direct conjugation of a detector molecule to an RNA probe synthesized enzymatically from a DNA template.

1. A preferred method for detection of oligonucleotides or other nucleic acid sequences directly conjugated to alkaline phosphatase:

Probes obtained from Molecular Biologicals, Inc. (DuPont SNAP probe) are used at a concentration of 1.0 ng per hybridization (6 nM concentration). These probes are hybridized in a mixture of 5×SSC, 0.5% SDS, and 1% BSA at 50 C. for 20 minutes in a humidified environment. Each sample is then washed at 42 C. for 5 minutes in 1×SSC buffer and then with 1×SSC buffer at room temperature for five minutes. The detection of alkaline phosphatase is then performed as previously described within Experimental Series E.

2. A method for single-copy detection of nucleic acid sequences in the human genome using oligonucleotides or other nucleic acids directly conjugated to fluorochromes. oligonucleotides (or other similarly long probes) are substituted with 5 amino(12)-2'-dUTP using conventional techniques. The chosen fluorochrome is then added in pH 9 bicarbonate buffer containing rhodamine (tetramethyl isothiocyanate) which reacts with the aliphatic amino group to form a covalent bond.

The system used to test this prepared oligonucleotide probe is a sequence in the human genome termed the "VNTR" or variable nonsense tandem repeats. This VNTR is a forty nucleotide repeat sequence present in tandem in the genome several thousand fold at the end of specifically identifiable chromosomes. The particular repeat of interest being used is a member of a family of repeats, each of which has preferred locations throughout the genome. This localization is important because other families such as Alu are dispersed irregularly through the genome. The confined nature of the VNTR forty nucleotide repeat and its aggregate large size (about 500 kilobases) makes it appropriate for detection using an oligonucleotide probe directly conjugated to a fluorochrome.

The empirical results show the presence of the prepared oligonucleotide probe bearing a fluorochrome as an area of fluorescence on specific chromosomes in the sample. The VNTR sequences are clearly seen with a fluorescence microscope as localized fluorescent bands along the ends of the individual chromosome. This empirical observation and result demonstrated the methodology as being suitable for the use of a double-labelled oligonucleotide probe for detection of specific genomic sequences within interphase chromosomes and nuclei. This capability would be especially useful in distinguishing chromosomal sites near disease genes such as in clarifying chromosomes in the absence of chromosomal banding patterns.

Conjugation of Oligonucleotides

Conjugation of fluorochromes to 5-amino(12)-2'kUTP occurs after addition of the nucleotide to the oligonucleotide using 3'-deoxy-terminal transferase. The amino-linked oligonucleotide is admixed with tetramethyl rhodamine in 0.1 M sodium bicarbonate buffer (pH 9.0) in dimethylformamide. The mixture components are allowed to react overnight at room temperature. The reaction products are then separated by passage twice through a G50 Sephadex column using 20 nM triethyl ammonium carbonate as the eluent. Purified oligonucleotide probe was recovered and concentrated by conventional lyphilization.

In-Situ Hybridization

The conditions for in-situ hybridization are preferably comparable to those described previously for the detection of EBV and nick-tranlated probes within Experimental Series B. However, in this system there are two distinct differences: first, the hybridization fluid mixture preferably does not contain salmon sperm; instead, an oligonucleotide of similar base composition and length is used as a non-specific competitor inhibitor. Second, the time for hybridization is desirably not more than two hours and can be as little as 10 minutes in duration. The rinses of the samples are the same as previously described. The detection step, however, requires only the introduction of light energy at the appropriate wavelength to the hybridized sample. Detection is immediate and is made visually by the unaided eye or preferably using fluorescence optics.

EXAMPLE 6

Progress in Human Gene Detection

Although considerable progress using the present invention has been made for human gene detection, only summary statements of the experiments and the empirical results were obtained.

1. Use of Probes Containing Repetitive DNA

We have recently worked out conditions for use of large genomic probes containing repetitive DNA to localize single-copy cellular genes. This was a high-priority undertaking, since the ability to use the wealth of preexisting genomic clones as hybridization probes would significantly facilitate gene mapping and increase the general applicability of this approach. It found that the presence of repetitive DNA in the probe need not be an obstacle, and can even be an asset. Hybridization to repetitive DNA produces a diffuse staining throughout the nucleus and a pattern of dark and light bands on the chromosomes (FIGS. 17G & H). The repetitive hybridization can be eliminated or "dimmed" to the desired extent, by including the appropriate amount of sonicated unlabelled human placental DNA to the hybridization reaction (FIG. 17, E & F). We have determined a preferred concentration of cold competitor DNA to add the hybridization buffer (1.5 mg/10 ml) for reducing repetitive hybridization without reducing single-copy signal. We have also found that the fragment size of the unlabelled competitive DNA is important and must be reduced by DNAase or sonication to between 100–300 nucleotides. This procedure has worked well for several 10 kb genomic clones and 35 kb cosmid clones containing much repetitive sequence. In some cases we prefer to allow some repetitive hybridization since this provides a very convenient source of banding patterns potentially useful for chromosome identification.

2. Detection of Sequences Within the Muscular Dystrophy Locus

Figure 14A:

We have obtained a large number of genomic and cDNA clones for different regions of the 2,000 kb DMD Duchenne/Becker Muscular Dystrophy locus (dystrophin, Koenig et al., Cell, 50: 509; Hoffman et al., 1987, Cell, 51: 919–928. Simultaneous hybridization using two 10–15 kb genomic probes known to be only 700 kb apart was easily visualized as paired fluorescent signals at interphase. FIGS. 14A & C illustrates results of hybridizations with these two probes in intact W1389 cells or lymphoma nuclei. Hybridization with just one probe produced only one signal in each nucleus (not shown), further validating that the presence of the paired spots represent resolution of two DNA sequences on a continuous DNA strand. These experiments with the dystrophin probes provide important confirmation that the powerful degree of interphase resolution indicated by our EBV studies is generally applicable to cellular endogenous genes. As also indicated by our EBV studies, we could frequently resolve these two dystrophin sequences, separated by 700 kb, on metaphase chromosomes as well. The intent of these initial experiments was to ascertain that this system would work. We have not yet thoroughly quantitiated the interphase distance between the paired signals, however, preliminary analysis of ten nuclei (Namalwa cells) indicated a distance of approximately 1.1–1.5 microns. This is consistent with the average 1.7 microns which we calculated corresponded to roughly 600 kb separating the Bam V fragments of two EBV genomes. The necessary pieces are now in place and working for us to undertake the proposed specific aims using the dystrophin locus as a model system.

Figure 14B:
Figure 14C:
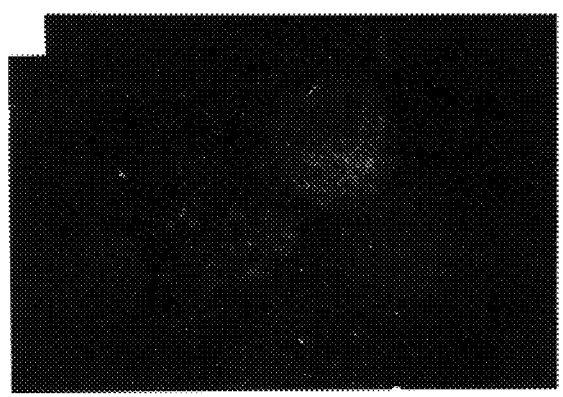
Figure 14D:
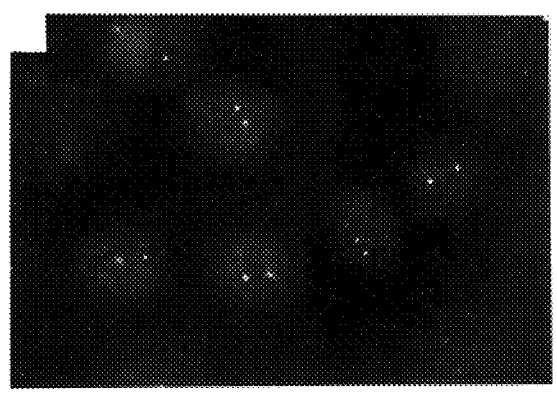
Figure 14E:
Figure 14F:
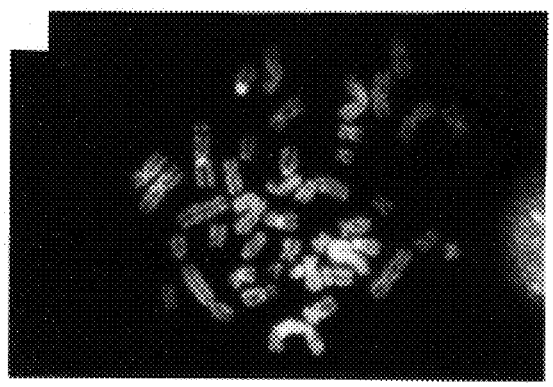
Figure 14G:
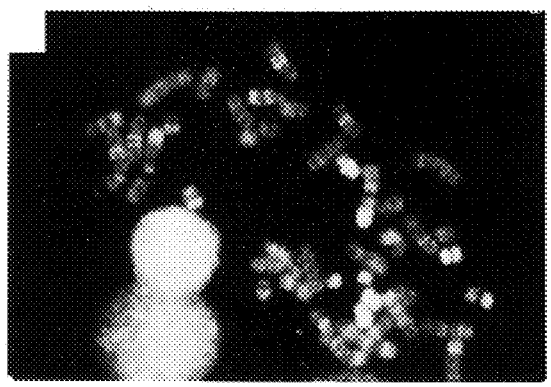
Figure 14H:
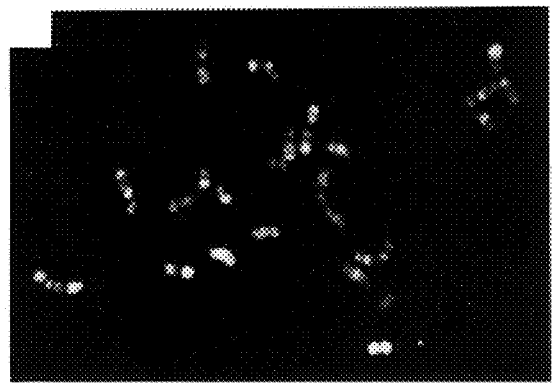

3. Double Hybridization with "Large" Neu Oncogene and "Small" Myosin Heavy Chain Sequence To assess our ability to work with cosmid clones, two overlapping cosmids to sequences encompassing the neu oncogene (erb B2) were obtained. The use of these cosmids also would illustrate the feasibility of providing double-lable through the targeting of a large and small sized sequence. Two overlapping cosmids for approximately 50–60 kb of DNA were hybridized simultaneously with the cardian MHC probe described above (13×2 genes=26 kb). FIGS. 14E and 14F show representative results of this hybridization. The stronger signals are apparent on FIG. 14E, as expected, where the neu oncogene has been mapped. One can readily distinguish this from the dimmer signals for MHC on two D group chromosomes (presumptive 14). This experiment confirms that fluorescence intensity is proportional to target size; and that different size targets provided a means of "double-label." While this technique for double-label is the most straightforward and convenient, there are a host of other possibilities. For example, simultaneous hybridization with one probe labelled by direct conjugation with rhodamine (as described in Experimental Series F) while the other probe is labelled with biotin and detected with fluorescein-avidin (as described in Experimental Series B and C).

4. Hybridization to Nuclei of Intact Cells and Myofibers

It is deemed important to reproduce single-copy DNA and RNA detection in well preserved nuclei within morphologically intact cells. This has already been performed successfully using intact cells fixed in 4% paraformaldehyde for ten minutes (no hypotonic solution). FIGS. 14A and 14B illustrate the present invention's ability to detect single-copy genes in nuclei of intact, normal human fibroblasts.

Our next goal was to extend these hybridization methods for the detection of genes and/or RNA within larger, more dense morphological structures as exemplified by myofibers. In approaching this problem, it was necessary to overcome obstacles inherent in the thick, dense morphology of these structures which results in very high background signal (noise) and poor probe penetrability. To solve these seemingly intractable limitations, a hybridization to total genomic DNA in chicken myofibers was employed. In initial experiments, there was only high background signal (noise) in the cytoplasm and essentially no signal in the nucleus. Follow up experiments, however, yielded greatly improved results as demonstrated by Figures and respectively, by employing a detergent extraction using 0.5% Triton X-100™ and 0.5% sapenin in PBS for 10 minutes both before and after fixation of the intact cells. This provides a cytoplasmic background signal (noise) which is acceptably low and a very strong nuclear hybridization signal for accurate and reproducible detection.

5. Detection of Cytogenetic Abnormalities

We believe that the improvements and advantages of the present methodology which provides direct visualization of individual genes within single cells also now makes possible a "molecular cytogenetic" approach for the detection and definition of chromosomal aberrations. This potential has been demonstrated in a series of experiments in which probes to normal human genes are hybridized to chromosomes of a cultured lymphoma cell line (such as Namalwa cells). The presence of translocations and duplications were empirically shown to be apparent by fluorescence detection of single genes. For example, a translocation of human chromosome 5 was readily detected and visually observed after in-situ hybridization of the prepared probe with a single-copy gene on the chromosome. A duplication of part of chromosome 1 was also clearly apparent from both metaphase and interphase nuclei after in-situ hybridization with the Blast-1 gene on chromosome 1. Based on this empirical showing, it is now deemed possible to employ the improved methodology for purposes of identifying all such cytogenetic aberrations and alterations routinely.

IV. Applications, Capabilities and Advantages

General Overview

The empirical data provided herein demonstrates a high resolution fluorescent technique for localizing single-copy genes by non-isotopic in situ hybridization. These methods provide a rapid and convenient means for mapping genes on metaphase chromosomes with 20 fold higher resolution than current autoradiographic techniques. Most importantly, however, fluorescent detection of genes in less condensed interphase chromatin (where gene sequences are separated 10 times farther apart and the chromatin is much less coiled than in the chromosomes) allows resolution of DNA sequences separated by less than 130 kb (roughly 0.13 centimorgans). Results with the MHC probe indicate that the alpha and beta cardiac MHC sequences on Chromosome 14, separated by only 28 kb, can be separately resolved. This work has demonstrated the feasibility of an approach termed "interphase chromatin mapping" whereby the physical proximity and order of DNA sequences from the same chromosomal region can be directly and rapidly assessed.

Having demonstrated the power of interphase mapping to resolve integrated viral and cellular sequences establishes the potential of this technique to identify closely linked cellular sequences and determine the order and approximate distance between them. It is extremely valuable to be able to physically map genes linked to known markers, without the long and expensive process of genetic recombination analysis. This allows a rapid approach to isolating important disease genes. Since current approaches now have a resolution limit of one megabase (one million nucleotides), the method described herein offers significantly improved resolution. Given the enormous effort currently expended on gene mapping strategies, this simple, direct approach has great potential to provide an alternative or complement to more complex, laborious and expensive methods for high-resolution localization of specific human genes. Most importantly, the technique is compatible with microscopy, the method by which cytogenetists evaluate human genetic disorders; and is a tool which would be a valuable addition to the arsenal of cytogenetic tools.

The implications of this technology for sensitive detection in just a single cell are far-reaching. All of this work relies upon localization of DNA or RNA sequences within nuclei or chromosomes, using sensitive, high-resolution in-situ hybridization technology of the present invention. Because the methodology is based upon rapid, non-isotopic detection, data can be accumulated rapidly relative to other techniques and are more compatible with commercial or clinical laboratories.

Several different aspects of this methodology have potential relevance to the analysis of other complex genomes and the investigation of genetic disease. These will take form as the following applications:

1) the demonstration and utilization of fluorescence detection of non-isotopic in-situ hybridization for precise regional localization of specific human genes on well-banded metaphase chromosomes. In order to couple high-resolution gene detection with high-resultion banding several G-banding and fluorescence banding strategies have been evaluated and optimized including bands produced by hybridization to repetitive sequences;

2. the use of interphase chromatin mapping for the detection of physical linkage between closely-spaced endogeneous sequences, using genomic clones to cellular sequences;

3. the use of the potential of interphase chromatin mapping to determine the order of tightly linked DNA sequences;

4. the application of interphase gene mapping for determining the proximity and order of markers near specific disease genes;

5. the determination of the localization of specific genes within the general topography of the interphase nucleus, in order to assess whether given genes occupy fixed positions and whether gene localization changes in relation to gene function;

6. the use of non-isotopic in-situ hybridization for clinical applications, as a tool for diagnosis of specific genetic disorders or for clinical cytogenetic research into etiology of genetic disease; and 7. the utilization of in-situ hybridization to investigate specific gene expression at the level of nuclear RNA, in order to: a. detect genetic defects which result in aberrant processing of specific RNAs; b. screen for expressed DNA sequences in a given cell type; and c. contribute to our understanding of nuclear structure and its relation to RNA processing and transport.

Capability and Significance

One major significance and capability of the present invention is its potential to make a fundamental contribution to human gene mapping by establishing a straight forward visual approach to determining DNA sequence linkage directly within interphase chromatin. This linkage analysis method is not simply a variation or improvement on current strategies for physical mapping of genes; it represents an innovative and qualitatively distinct approach. Over the past decade a great deal of time and effort has been invested in the development of appropriate family pedigrees, information RFLP's, and computerized statistical approaches to determine genetic recombination frequencies as a measure of gene linkage (Botstein et al., 1980) *Am. J. Hum. Genet.,* 32: 314. Under optimal conditions, this approach can detect linkage down to a resolution of 1,000–2,000 kb (roughly 1 centimorgan). This approach has been and continues to be invaluable as a means of identifying DNA markers close to a disease gene. However, it is labor intensive, limited in resolution, and, due to non-homogeneous recombination rates across the chrmosome, not an accurate measure of physical distance. In more recent years, methods have been developed to assess physical linkage over smaller distances, most notably by pulsed-field gel electrophoresis whereby the continuity of DNA sequences separated by several hundred kb can be detected (Schwartz and Cantor, 1984) *Cell,* 37: 67. While this has also proven to be a highly valuable technique, its applications are restricted by the upper limit of resolution and the presence of genomic areas lacking the appropriate distribution of required restriction enzyme sites. Hence, there is a need for additional physical mapping methods which are rapid and would more comfortably bridge the gap between genetic recombination and pulse-field gel electrophoresis. Even when several DNA markers have been shown to be tightly clustered by genetic or physical mapping methods, it is often difficult to determine definitively the order of the DNA sequences and their orientation on the chromosome. Hence, additional methods to facilitate ordering of sequences are needed.

The novel "interphase chromatin mapping" method provided by the present invention derives from the important observation that when the chromatin fiber folds it apparently does not condense the distance between closely spaced genes nearly to the extent that it reduces the overall length of the chromosome. This observation was made possible by development of a fluorescent detection technique for single-copy genes which provides the highest resolution possible at the light microscope level, and has a consistently high hybridization efficiency and negligible background. The implication of this observation is that, for many purposes, it may not be necessary to remove DNA from the nucleus, chop it into pieces, and subject it to a technically and analytically laborious analysis in order to determine how the pieces were arranged in the cell. The results document the feasibility of hybridizing the DNA sequences directly within the nucleus and visually evaluating their linkage. This approach makes it possible to ascertain the degree of physical linkage between any two cloned DNA sequences ranging from non-syntenic to 100 kb (0.1 centimorgan) or less. These experiments can also yield the chromosomal location (s) of the two sequences and their order on a given chromosome. Because loosely linked genes are resolvable on metaphase chromosomes and more tightly-linked genes are resolvable at interphase, linkage may be evaluated as a continuum encompassing both the distances approachable by genetic recombination analysis (thousands of kb) and the distances readily encompassed by pulsed-field gel electrophoresis (100's of kb). This method allows the rapid approximation of physical distance between any cloned DNA sequences in a much more cost-effective and less labor intensive manner than current techniques.

Another advantage of the unique in-situ approach is that, at the same time one evaluates gene linkage in interphase nuclei, one can acquire information regarding the higher-level nuclear and chromosomal organization of these same sequences. Efforts to describe and understand the organization of complex genomes should ultimately include investigations into the three dimensional organization of these genes in their functional state at interphase.

Another aspect of this unique methodology is for investigations of genetic disease and the ability to detect primary nuclear transcripts from expressed genes. High-resolution visualization of specific viral RNAs has revealed the highly localized, often curvilinear distribution of "tracks" of nuclear RNAs. This nuclear RNA detection can provide a valuable tool for investigating genetic disease or for screening cloned genomic DNA sequences to find a defect at one of several steps from gene to active protein. The hnRNAs for most expressed genes undergo a series of complex processing steps after which they must be effectively transported to the cytoplasm as mature mRNA. Using Duchenne's Muscular Distrophy (DMD) as a model system, a significant fraction of genetic defects in this gene (other than the 50% known to be deletions) may result from defects in the enormous degree of processing that the dystrophin transcripts must undergo. The novel non-isotopic in-situ hybridization procedure described provides a tool for detection of defects in RNA processing which may result in accumulated nuclear RNA.

An area of potential long-term impact is the use of high-resolution in-situ hybridization techniques for "molecular cytogenetics." The advantage of fluorescence detection for "straight forward" chromosomal assignment of genes as compared to somatic cell hybrids or autoradiographic in-situ are clear (for example, chromosomal localization of two different genes simultaneously, within one cell). The advantage is not only higher resolution, but also that signal to noise ratio is significantly improved. Since the labelled chromosome is apparent from one metaphase, it is not necessary to identify and analyze the distribution of label over all the chromosomes in large numbers of metaphases. While this has basic research value for chromosome gene mapping, the speed, convenience, and quality of this chromosomal detection renders it amenable to clinical applications. In the future, clinical cytogenetics may no longer be restricted to detection of relatively gross chromosomal abnormalities. A finer resolution molecular analysis of sequences at intervals along the chromosome may be possible. The molecular cytogenic technique is capable of detecting misplaced DNA anywhere within the genome, a powerful potential for future clinical diagnosis and research. Potential applications could be either for diagnosis of specific genetic disease through amniocentesis or carrier detection, or for clinical cytogenetic research into the etiology of genetic disease. The Duchenne's Muscular Dystrophy gene provides a good example since it is now known that over half of DMD patients carry a deletion (most of which are large, up to thousands of kb). Chromosomes exhibiting deletions of several kb or more should be detectable in both carriers and amniotic fluid cells. The in-situ approach could prove an important complement or alternative to the Southern blot technique which requires larger cell samples and is more labor intensive. The technique described herein can analyze either interphase or metaphase cells and is performed in 1–2 days on routine cytogenetic preparations. In the 50% of Duchenne's cases in which a deletion is not detectable on blots, other rearrangements, such as insertions, inversions, or translocations may be deciphered by a high-resolution molecular cytogenetic approach. Application of this technique need not be restricted to defects in individual genes. An important potential application of interphase mapping is the detection of aneuploidy such as trisomy 21, 13, or 18; or sex chromosome anomalies such as XO, XXX, and YY. In situations where the defect is an access of normal genetic material rather than aberrant genetic material, in-situ hybridization will enable such gene dosage defects to be detected very simply as three visual signals rather than two, for example the trisomics. In-situ hybridization will, therefore, become an extremely powerful method for detecting such gene dosage diseases. This is extraordinarily difficult using Southern Blot techniques.

When in-situ hybridization could provide the needed diagnosis for a given genetic disease, it believe it could become the preferred method because:

1. The technique is more rapid than filter hybridization;
2. only a small number of cells is required, and these need not be cycling there may be no need to culture amniotic fluid cells, which takes several weeks during a critical time in pregnancy;
3. the methods are non-isotopic and, therefore, more amenable to clinical use; and
4. the cost may be significantly less.

Currently, the routine screening for general Karyotypic abnormalities in amniotic fluid cells or in cells of babies with a variety of birth defects is restricted to a relatively crude analysis of banding patterns on metaphase chromosomes. With the identification of more and more DNA markers which span each chromosome and the development of rapid and efficient in-situ hybridization methods, we envision the "molecular cytogenetics" of the future to couple routine cytogenetics with DNA probe methodologies to provide a more powerful tool for assessing karyotypic deviations. While the development of such an approach is clearly at a very early stage, it has a variety of potential applications. For example, a routine amniocentesis reveals a translocation between two autosomal chromosomes and banding analysis cannot resolve the critical question of whether the translocation is "balanced." Hybridization of several probes known to reside in this chromosomal regions ("catalogues" of probes to each chromosome are being developed) could provide much higher resolution information as to whether a deletion (or duplication) has occurred. In the case of birth defects with unknown cause, research efforts could undertake more extensive analysis with probes which span the genome in order to screen for deleted or misplaced sequences.

A method which allows rapid screening of DNA sequences to determine which are transcribed could be quite valuable. Methods to block nuclear RNA transport can be used to enhance detectability of low abundance RNAs. For example, cordycepin blocks polyadenylation and transport of nuclear RNA such that a focal concentration of nuclear RNA may accumulate. To a great extent the ability to sensitively detect a low abundance sequence depends upon the way in which it is distributed within the cell. The highest focal concentration of transcripts probably occurs at the site of nuclear transcription and processing, thus, this method could increase sensitivity of detection for low abundance sequences.

In addition, nuclear RNA detection will prove to be a useful tool for identifying and investigating genetic defects which result in aberrant RNA processing or transport. Again using DMD as an example, the primary transcript from this gene undergoes extensive processing of enormous (35 kb) introns, and the final mRNA, although low abundance, is large enough (14 kb) to visualize a single molecule. Mutations involving consensus sites for splice junctions or other sequences critical for processing this enormous transcript could prevent transport of the unprocessed RNA from the nucleus. We have observed that in cells latently infected with EBV, there is a large and easily detectable accumulation of primary transcripts within the nucleus, even though corresponding mRNA or protein products are essentially undetectable. Hence, accumulations of nuclear RNA occur and are detectable in-situ for the first time by our approach.

A capability of major importance is the ability to rapidly and sensitively detect viral genomes in an expressed or unexpressed state. Thus, the method of this invention can identify integrated viral DNA within host cell DNA and distinguish it from identical DNA episomes which have not been integrated into the host gene sequence. The method can also distinguish between nuclear or cytoplasmic RNA.

The present methodology provides a rapid means of detecting both productive and latent viral infections in as little as one cell. As demonstrated by the data for HIV detection, the method is sensitive in two distinct ways: one or a few positive cells can be detected among hundreds of thousands of negative cells; and a very weak positive cell which is only just beginning to express viral sequences (nuclear foci) can be detected and distinguished readily from fully productive cells. The presence or absence of a nuclear focus of viral RNA can also be used as an indication of viral productivity or gene expression. This is deemed useful in the testing of anti-viral agents. As shown by the empirical data regarding EBV detection, this methodology can detect as little as one viral genome (or fraction of a genome). Hence, in any disease state in which a latent viral infection is implicated, this procedure can serve as an important diagnostic tool. Such a tool has great investigative and diagnositc potential—as for example in the detection of human papilloma virus in a pre-disease state of cervical carcinoma, or in a variety of clinical conditions in which lentiviruses are implicated. Human papilloma virus exists in a variety of subtly different genomic forms. Types 16, 18, 31, and 33 have been shown to be associated with a high risk of development of cervical cancer. In-situ hybridization will enable these types to be differentiated from other genomic forms of the virus.

Another important capability of this invention is the detection of gene amplification or deletion causing aberrant gene expression—as occurs during oncogenesis. In this instance, the amplification of oncogenes has been described for the myc oncogene in several cancers and for the neu oncogene in mammary breast carcinoma. The ability to detect these amplified oncogenes, potentially at a time prior to any clinical disease state, can prove critical for the accurate and early diagnosis of serveral types of cancer. Because other known methods would quantitate oncogenes of their transcripts averaged over many cells—only a few of which may be positive—it would be more difficult or impossible to detect a few aberrant cells. The methods for in-situ hybridization described herein can provide for greater sensitivity than existing methods and when coupled with cellular morphological information, provides definitive diagnosis of disease or predisease states. The degree of amplification of an oncogene may prove to have prognostic value and meaningfully aid in therapeutic decision making. The visual method of detecting hybridization signal will enable gene amplification to be seen very clearly as signals. This provides the potential to quantify the degree of amplification at the oncogene level.

While amplification of oncogenes has documented importance, the deletion of specific genes is equally important. For example, in familial polyposis coli, there is an inherited predisposition to develop intestinal polyps which is associated with a heterozygous deletion of a region of human Chromosome 5. It has been recently shown that when the polyps become malignant, this condition is associated with a homozygous deletion of Chromosome 5. The in-situ hybridization procedure described provides the unique capability of assessing a deletion for a specific gene in a single cell; and is able to distinguish between a heterozygous deletion (only one homologue affected) and a homozygous deletion (both homologues being affected) which is a prelude to colon cancer. The development of hymozygous deletions has also been implicated in other inherited diseases predisposing to cancer such as retinoblastoma.

V. Kits Utilizing In Situ Hybridization and Non-Isoptopic Detection Methods

It will recognized by practitioners ordinarily skilled within this art that the in situ hybridization protocol described earlier herein is compatible with all previously known methods of non-isotopic detection. The in situ hybridization methodology is streamlined so that fewer manipulations are necessary and that these steps may be performed in a much shorter period of time than has been previously possible. It is expected that the reagents will be provided in kit form to practice the protocol which has been optimized for simplicity and for compatibility with a wide variety of detection methods. It is also expected that such prepared kits, containing specifically prepared reagents and probes, will be most applicable in clinical/diagnostic laboratory where the ability to detect the presence (or absence) of specific nucleic acids would serve to positively or negatively identify cancerous or tumor cells, virally infected cells, and other pathological stated characterized by the presence of specific genes.

How the kit could be used for diagnostic purposes is illustrated by the following example. The diagnosis of whether or not cells taken from a subject are cancerous depends on a pathological evaluation which, in turn, depends on identifying criteria involving cellular morphological parameters, staining characteristics, and the presence (or absence) of certain enzymes and/or surface antigens. Current methods of diagnosis are thus not entirely accurate and are imprecise as to the future prognosis of the cell or tissues. However, the major drawback to diagnostic procedures presently in use is their inability to detect the cancerous nature of the cell or tissues until a tumor has developed on a multicellular level or in gross. Recently, it has been demonstrated (U.S. Pat. No. 4,535,058) that the oncogenic potential (the uncontrolled growth) of cells and tissues is the result of a mutated gene known as an "oncogene". The DNA from this gene has been isolated and sequenced to show that it is, in fact, a true mutation of the normal gene, the proto-oncogene. This oncogene has been shown to be present and active in several kinds of of human tumors including lung, bladder, brain, and the like. The in situ hybridization of oncogenes as probes specific for a cancerous cell will allow an identification of the mutation in the cells or tissues of a person and a positive diagnosis long before it could be detected pathologically; moreover, in situ hybridization would indicate the exact type and nature of oncogene mutation being expressed, there being many known oncogenes. The results of in situ hybridization would have prognostic value in that it would permit prediction of the growth potential of these now identified cells once the oncogene expressed within the test sample is correlated with known carcinogenic potential. In addition, after the laboratory diagnosis is made, the efficacy of certain regimens of chemotherapy or radiation treatments can be assessed by determining the extent of repression of the identified oncogene(s) after therapy by again utilizing kits for in situ hybridization of treated cells. Test kits for in situ hybridization should preferably be compatible with a hospital pathology laboratory in practice, in equipment, and in the skills demanded from the user. Such kits, being simple, accurate, and rapid, are then expected to become an integral part of the routine testing procedures used by the laboratory. Each such kit would then be formulated to identify and detect a particular condition. Some examples are the detection of genital herpes in cells from cervical smears or AIDS virus from peripheral blood cells. The present invention has empirically detected the presence of AIDS (HIV) virus in infected human lymphocytes and empirically detected the presence of human muscular dystrophy DNA in human cells taken from afflicted patients.

Kit Contents

Preferred Reagents for In Situ Hybridization

Solution A: formamide (deionized); dextran sulfate (10%); human DNA or salmon sperm DNA (100 ug/ml); human tRNA (100 ug/ml); and vanadyl sulfate (10 uM).

Solution B: 4×SSC buffer (0.6 M sodium chloride and 0.06 M sodium citrate, pH 7.2).

Solution C: 4% paraformaldehyde in phosphate buffered saline containing 10 mM magnesium chloride.

Probes: (dry preparations in present quantities within microcentrifuge tubes);

Probe A: positive control DNA with a biotin label;

Probe B: a test probe comprising a biotin label and at least one nucleotide sequence substantially similar to at least a portion of the specific nucleic acid of interest suspected of being present in the sample; and Probe C: negative control DNA with a biotin label. For biotinylated probes, up to five sets of standard reagents may be used. It is also desirable to include positive control slides specific for a gene or DNA of interest at a known quantity in the cell type to be tested. A negative control slide to test and evaluate background signal is also useful.

Set I

Solution 1: avidin (2 ug/ml) or streptavidin (2 ug/ml) in 4×SSC buffer;

Solution 2: biotinylated fluorescein (1 ug/ml).

Set II

Solution 1: avidin (2 ug/ml) or streptavidin (2 ug/ml) in 4×SSC buffer;

Solution 2: biotinylated polyalkaline phosphatase (1 ug/ml);

Solution 3: bromochloroindolyl phosphate (50 ug/ml) in dimethylformamide;

Solution 4: nitroblue tetrazolium (75 mg.ml in 70% dimethylformamide).

Set III

A single solution: streptavidin-alkaline phosphase conjugate.

Set IV

A single solution: probe conjugated directly to a fluorochrome.

Set V

A single solution: probe conjugated directly to alkaline phosphatase.

Each kit will contain a set of instructions which employ these reagents as part of the novel in-situ hybridization method and at least one detection method.

It is expressly understood also that other methods for detecting nucelic acids presently known and used in this art such as antibodies and antigens may be prepared as reagents and utilized in kit form with the present invention.

The present invention is not to be limited in form nor restricted in scope except by the claims appended hereto.

Equivalents

Those skilled in the art will recognize or be able to ascertain using no more than routine experimentation, many equivalents to the specific embodiments of the invention described herein. Such equivalents are intended to be covered by the following appended claims.

We claim:

1. A method for detecting a target nucleic acid within cellular material by in-situ hybridization with an iterative effect whereby hybridized probe fragments line up along a strand of the target nucleic acid, thereby amplifying the signal from the target, comprising the steps of:

(a) fixing the cellular material with a fixative that retains and preserves the target nucleic acid and allows probe penetration of the cellular material;

(b) contacting the cellular material with a hybridization fluid comprising a non-homopolymeric probe consisting essentially of a multiplicity of non-radioactively labelled, heterogeneous nucleic acid fragments collectively complementary to a multiplicity of portions along said target nucleic acid, each fragment having from about 20 to 1,000 nucleotides, under conditions such that the probe hybridizes specifically to the target nucleic acid if present, said nucleic acid fragments selected or chemically synthesized so as to exclude substantially all nucleic acid fragments longer than 1,000 nucleotides; and (c) detecting the probe hybridized to said target nucleic acid if present.

2. The method according to claim 1, wherein each fragment has from about 100 to about 700 nucleotides.

3. The method according to claim 1, wherein the cellular material is interphase chromatin.

4. The method according to claim 1, wherein the cellular material is a metaphase chromosome.

5. The method according to claim 1, wherein the cellular material is a nucleus.

6. The method according to claim 1, wherein the cellular material is a morphologically preserved, intact cell.

7. The method according to claim 1, wherein the target nucleic acid is a deoxyribonucleic acid.

8. The method according to claim 1, wherein the target nucleic acid is a ribonucleic acid.

9. The method according to claim 1, wherein the non-radioactive label is a fluorophore.

10. The method according to claim 1, wherein the non-radioactive label is selected from the group consisting of biotin, avidin and streptavidin.

11. The method according to claim 1, wherein the non-radioactively labelled fragments are present in the hybridization fluid at a concentration of not less than 0.2 $\mu$g/ml.

12. The method according to claim 1, wherein the method further comprises a post-hybridization rinsing step consisting of three separate rinses, each having a duration of between 5 and 30 minutes.

13. The method according to claim 3, wherein the fixative is a mixture of methanol and acetic acid in a 3:1 volumetric ratio.

14. The method according to claim 4, wherein the fixative is a mixture of methanol and acetic acid in a 3:1 volumetric ratio.

15. The method according to claim 5, wherein the fixative is a mixture of methanol and acetic acid in a 3:1 volumetric ratio.

16. The method according to claim 6, wherein the fixative is paraformaldehyde.

17. The method according to claim 1, wherein the non-isotopic label is an enzyme.

18. The method according to claim 17, wherein the enzyme is alkaline phosphatase.

19. The method according to claim 1, wherein said fragments have sizes that are small compared to the target nucleic acid and are present in high concentration, thereby enhancing the signal-to-noise ratio in said method for detecting a target nucleic acid.

20. The method of claim 1, wherein said portion of said target nucleic acid is at least 2,000 nucleotides.

21. The method of claim 1, wherein said nucleic acid fragments are DNA fragments.

22. The method of claim 1, wherein said nucleic acid fragments are RNA fragments.

23. The method according to claim 1, wherein the hybridization fluid further comprises:
   (a) a non-specific nucleic acid competitor, said non-specific competitor being of similar origin as the nucleic acid probe, said origin being selected from the group consisting of prokaryotic and eukaryotic origins;
   (b) a soluble salt; and
   (c) an ionizing solvent.

24. The method according to claim 23, wherein the soluble salt is sodium chloride at a concentration between 0.3 M and 0.6 M.

25. The method according to claim 23, wherein the ionizing solvent is formamide at a concentration of 50% (v/v).

26. The method according to claim 23, wherein the hybridization fluid further comprises vanadyl sulfate at a concentration of 10 mM.

27. The method according to claim 23, wherein the hybridization fluid further comprises dextran sulfate at a concentration of 10% (w/v).

28. The method according to any one of claims 1–20 and 23–27, wherein the method has a sensitivity sufficient to detect a single copy of a target nucleic acid.

* * * * *